US009468637B2

(12) United States Patent
Fienberg et al.

(10) Patent No.: US 9,468,637 B2
(45) Date of Patent: Oct. 18, 2016

(54) ORGANIC COMPOUNDS

(75) Inventors: Allen A. Fienberg, New York, NY (US); Lawrence P. Wennogle, New York, NY (US); Sharon Mates, New York, NY (US)

(73) Assignee: INTRA-CELLULAR THERAPIES, INC., New York, NY (US)

(*) Notice: Subject to any disclaimer, the term of this patent is extended or adjusted under 35 U.S.C. 154(b) by 311 days.

(21) Appl. No.: 13/319,807

(22) PCT Filed: May 13, 2010

(86) PCT No.: PCT/US2010/001444
§ 371 (c)(1),
(2), (4) Date: Nov. 10, 2011

(87) PCT Pub. No.: WO2010/132127
PCT Pub. Date: Nov. 18, 2010

(65) Prior Publication Data
US 2012/0053190 A1    Mar. 1, 2012

Related U.S. Application Data

(60) Provisional application No. 61/178,035, filed on May 13, 2009.

(51) Int. Cl.
| A01N 43/90 | (2006.01) |
| A61K 31/519 | (2006.01) |
| C07D 471/04 | (2006.01) |
| C07D 471/22 | (2006.01) |
| A01N 43/66 | (2006.01) |
| A61K 31/53 | (2006.01) |
| A61K 31/495 | (2006.01) |

(52) U.S. Cl.
CPC ............ *A61K 31/495* (2013.01); *A61K 31/519* (2013.01)

(58) Field of Classification Search
CPC ................... A61K 31/519; A61K 31/495
USPC ..................... 514/257, 246, 262.1
See application file for complete search history.

(56) References Cited

U.S. PATENT DOCUMENTS

| 4,666,908 A | 5/1987 | Hamilton |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshlan et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 8,273,750 B2 | 9/2012 | Li et al. |
| 8,273,751 B2 * | 9/2012 | Li .................. 514/257 |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 * | 9/2014 | Li .................. 514/257 |
| 9,000,001 B2 | 4/2015 | Li |
| 9,073,936 B2 | 7/2015 | Li et al. |
| 2003/0069246 A1 | 4/2003 | Darrow et al. |
| 2003/0162782 A1 | 8/2003 | Grossman et al. |
| 2003/0211040 A1 | 11/2003 | Greengard et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2008/0096870 A1 * | 4/2008 | Martynyuk et al. .......... 514/220 |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Fienberg et al. |
| 2010/0173878 A1 | 7/2010 | Li et al. |

(Continued)

FOREIGN PATENT DOCUMENTS

| DE | 19931206 | 1/2001 |
| EP | 0063381 | 10/1982 |

(Continued)

OTHER PUBLICATIONS

PDE1—(http://en.wikipedia.org/wiki/PDE1), 2014.*
Medina (Frontiers in Science, 2011, p. 1-5).*
Cristina (Lucrari STIINTIFICE Medicina Veterinara XLIII, 2, 2010).*
Ghosh et al. ( Int J of PharmTech Research, 1, 4, 1148-60, Oct.-Dec. 2009).*
Siuciak (CNS Drugs, 2008, p. 983-993).*
(http://sbir.gov/ sbirsearch/detail/201838)—Accessed Mar. 26, 2014.*
Vatter, et al., J. of Neurochemistry, 93,321-329 (2005).*
Upfal (Drug Guide, 2007, p. 321-324).*

(Continued)

*Primary Examiner* — Uma Ramachandran
(74) *Attorney, Agent, or Firm* — Hoxie & Associates LLC

(57) ABSTRACT

The present invention relates to a new use of phosphodiesterase 1 (PDE1) inhibitors for the treatment of psychosis, schizophrenia, schizoaffective disorder, schizophreniform disorder, psychotic disorder, delusional disorder, mania, or bipolar disorder.

5 Claims, No Drawings

(56) References Cited

U.S. PATENT DOCUMENTS

| | | |
|---|---|---|
| 2010/0273753 A1 | 10/2010 | Li et al. |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0094966 A1 | 4/2012 | Li et al. |
| 2012/0136013 A1 | 5/2012 | Li et al. |
| 2012/0201754 A1 | 8/2012 | Li et al. |
| 2012/0238589 A1 | 9/2012 | Li et al. |
| 2013/0018063 A1 | 1/2013 | Li et al. |
| 2013/0085123 A1 | 4/2013 | Li et al. |
| 2013/0239234 A1 | 9/2013 | Greengard et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2015/0197528 A1 | 7/2015 | Li et al. |

FOREIGN PATENT DOCUMENTS

| | | | |
|---|---|---|---|
| EP | 0201188 | | 12/1986 |
| EP | 0911333 | | 4/2002 |
| JP | 53031694 | | 3/1978 |
| KR | 10-1991-0006866 | | 9/1991 |
| WO | WO 91/19717 | | 12/1991 |
| WO | WO 94/19351 | | 9/1994 |
| WO | WO 98/46606 | | 10/1998 |
| WO | WO 98/52568 | | 11/1998 |
| WO | WO 03/002567 | | 1/2003 |
| WO | WO 03/020702 | | 3/2003 |
| WO | WO 03/020724 | | 3/2003 |
| WO | WO 03/042216 | | 5/2003 |
| WO | WO 03093499 | * | 11/2003 |
| WO | WO 2006/133261 | | 12/2006 |
| WO | WO 2007/025103 | | 3/2007 |
| WO | WO 2007/143568 | | 12/2007 |
| WO | WO 2007/143705 | | 12/2007 |
| WO | WO 2009/073210 A1 | | 6/2009 |
| WO | WO 2009/075784 A1 | | 6/2009 |
| WO | WO 2011/043816 | | 4/2011 |
| WO | WO 2011/153129 | | 12/2011 |
| WO | WO 2011/153135 | | 12/2011 |
| WO | WO 2011/153136 | | 12/2011 |
| WO | WO 2011/153138 | | 12/2011 |
| WO | WO 2013/192556 | | 12/2013 |
| WO | WO 2014/151409 | | 9/2014 |

OTHER PUBLICATIONS

Burger (Progress in Drug Research, vol. 37, 1991, p. 287-328).*
Ehrman et al., "Phosphodiesterase 1B differentially modulates the effects of methamphetamine on locomotor activity and spatial learning through DARPP32—dependent pathways: evidence from PDE1B-DARPP32 double-knockout mice", Genes Brain Behav. Oct. 2006; 5(7):540-551.
Noguchi et al. "A Facile Preparation of 7-(substituted amino)-6H-pyrrolo[3,4-d]-pyrimidine Derivatives." Bulletin Chem. Soc. of Japan, 62(9), 3043-5; (1989).
U.S. Appl. No. 14/125,017, filed Mar. 2014, Li, et al.
U.S. Appl. No. 14/252,511, filed Apr. 2014, Li, et al.
U.S. Appl. No. 14/169,352, filed Jan. 2014, Li, et al.
"Anxiety," [retrieved on May 14, 2008]. Retrieved online via Internet, URL: http://www.nim.nih.gov/medlineplus/anxiety.html.
"Autism," [retrieved on May 14, 2008]. Retrieved online via Internet, URL: http://www.nim.nih.gov/medlineplus/autism.html.
U.S. Appl. No. 12/746,236, Final Rejection Mar. 27, 2012.
U.S. Appl. No. 12/746,236, Non-Final Office Action Nov. 29, 2011.
Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chem. (1997) 40(14):2196-2210.
Al-Afaleq, E., et al., "Heterocyclic o-Aminonitriles: Preparation of Pyrazolo[3,4-d]-pyrimidines with Modification of the substituents at the 1-position", Molecules, 6, pp. 621-638, (2001).
Banker, Gilbert S. et al., Modern Pharmaceutics, Marcel Dekker, New York, 1996.
Bastia et al., Effect of $A_1$ and $A_{2A}$ Adenosine Receptor Ligands in Mouse Acute Models of Pain, Neuroscience letters (2002) 328:241-244.
Bender et al., "Cyclic Nucleotide Phosphodiesterases: Molecular Regulation to Clinical Use" PharmcoL Rev., 2006, 58, pp. 488-520.
Burnouf et al., "Synthesis, Structure-Activity Relationships, and Pharmacological Profile of 9-Amino-4-0xo-1-Phenyl-3,4,5,6, 7-Tetrahydrol[I,4]Diazepino[6, 7, 1-hi]Indoles: Discovery of Potent, Selective Phosphodiesterase Type 4 Inhibitors," (2000), J. Med. Chem., 43:4850-4867.
Chebib et al., 1-Phenylpyrazolo[3,4-d]pyrimidines; Structure-Activity Relationships for C6 Substituents at $A_1$ and $A_{2A}$ Adenosine Receptors Bioorganic & Medicinal Chemistry (2000) 8:2581-2590.
Chermat et al. Journal Pharmacology (1986) 17: 348-350.
Dewald et al., Synthesis and Potential Antipsychotic Activity of 1 H-Imidazo[1.2-c]pyrazolo[3,4-e]pyrimidines', J. Med. Chem. 1988, 31, pp. 454-461.
Fienberg et al., "DARPP-32: Regulator of the Efficacy of Dopaminergic Neurotransmission", Science, (1998) 281, pp. 838-842.
Gelbin, et al., "Ketene-S, N-acetals as synthons for heterocycles new synthesis of pyrimidinones", Journal Fuer Praktische Chemie, vol. 329, No. 5, pp. 753-766, (1987).
Goodman & Gilman, The Pharmacological Basis of Therapeutics, McGraw-Hill Interamericana. 2007, p. 892.
Greengard et al., "Beyond the Dopamine Receptor: the DARPP-321Protein Phosphatase-1 Cascade", Neuron, 1999,23, pp. 435,447.
Han et al., "The Calcium/Calmodulin-dependent Phosphodiesterase PDE1C Downregulates Glucose-induced Insulin Secretion", J. Bio, Chem., 1999,274(32), pp. 22337-22344.
Jiang, et al., Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol, J. Org. Chem., 70, 2824-2827 (2004).
Lundqvist et al., Exploitation of Structural and Regulatory Diversity in Glutamate Racemases, Nature (2007) 447:817-822.
Mani et al., Science (2000) 287: 1053.
Murray et al., "Expression and activity of cAMP phosphodiesterase isoforms in pulmonary artery smooth muscle cells from patients with pulmonary hypertension: role for PDE1", Am. J. Physiol. Lunr:l Cell Mol. Physiol. 2007, 292, pp. L294-L303.
Murray et al., "LY503430, a Novel _-Amlno-3-hydroxy-5-methylisoxazole-4-proplonlc Acid Receptor Potentiator with Functional, Neuroprotective and Neurotrophic Effects in Rodent Models of Parkinson's Disease" JPEJ 2003) 306:752-762.
Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission", J. Pharmacol. Sci. vol. 114, pp. 6-16, (2010).
Park, et al., "Traumatic Brain Injury: Can the consequences be stopped?" CMAJ, 178(9), 1163-1170, (2008).
Polli et al., "Expression of a Calmodulin-Dependent Phosphodiesterase Isoform (PDE1 B1) Correlates With Brain Regions Having Extensive Dopaminergic Innervation," (1994), The Journal of Neuroscience, 14:1251-1261.
Porsolt et al. Nature (1977) 266:730-732.
Poulsen et al.Hlgh-Pressure Synthesis of Enantiomerlcally Pure C-6 Substituted Pyrazolo[3,4-d]pyrimidines Biorganic & Medicinal Chemistry letter (2001) 11:191-193.
Reed et al., "Phosphodiesterase 1 B Knock-Out Mice Exhibit Exaggerated Locomotor Hyperactivity and DARPP-32

(56) References Cited

OTHER PUBLICATIONS

Phosphorylation in Response to Dopamine Agonists and Display Impaired Spatial Learning", The Journal of Neuroscience, 2002, 22(12), pp. 5188-5197.
Rybalkin et al., "Cyclic GMP Phosphodiesterases and Regulation of Smooth Muscle Function", Circ. Res. 2003,93, pp. 280-291.
Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium", Cancer Research, 2004, 64, pp. 2568-2571.
Turko et al., Inhibition of Cyclic GMP-Binding Cyclic GMP-Specific Phosphodiesterase (Type 5) by Sildenafil and Related Compounds Molecular Pharmacology (1990) 56:124-130.
UNGERSTEDT Acta Physiology Second Suppl. (1971) 367:1-48.
UNGERSTEDT et al. Brain Research (1970) 24: 485-493.
Wolff, Manfred E., Burger's Medicinal Chemistry and Drug Discovery, Fifth Ed., vol. 1: Principles and Practice, John Wiley & Sons, 1995, 975.
Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).
Shook, et al. "Design and Characterization of Optimized Adenosine $A_{2A}/A_1$ Receptor Antagonists for the Treatment of Parkinson's Disease", *J. Med. Chem.*, pp. 1-47 (2012).
Aswar, "Anti-Cataleptic Activity of Various Extracts of *Ocimum sanctum* ", *International Journal of Pharma. Research and Development*, vol. 2, Issue 6, pp. 1-7 (2010).
Boyd et al., "Dopamine receptor signaling and current and future antipsychotic drugs", *Handb Exp Pharmacol*. 2012; (212):53-86. doi: 10.1007/978-3-642-25761-2_3.
Deshmukh et al., "Amelioration of intracerebroventricular streptozotocin induced cognitive dysfunction and oxidative stress by vinpocetine-a PDE1 inhibitor" *European Journal of Pharmacology* (2009), 620(1-3), 49-56.
Filgueiras et al., "Phosphodiesterase type 1 inhibition improves learning in rats exposed to alcohol during the third trimester equivalent of human gestation" *Neuroscience Letters* (2010), 473(3), 202-207.
Schmidt, "Phosphodiesterase inhibitors as potential cognition enhancing agents" *Current Topics in Medicinal Chemistry* (2010), 10(2), 222-230.
Ehrman et al., "Phosphodiesterase 1B differentially modulates the effects of methamphetamine on locomotor activity and spatial learning through DARPP32-dependent pathways: evidence from PDE1B-DARPP32 double-knockout mice", *Genes Brain Behav*. Oct. 2006;5(7):540-51.
Klaissle, "Physical activity and environmental enrichment regulate the generation of neural precursors in the adult mouse substantia nigra in a dopamine-dependent manner" *BMC Neurosci*. 2012)31;13:132. doi: 10.1186/1471-2202-13-132.
Kleppisch, "Phosphodiesterases in the central nervous system" *Handb Exp Pharmacol*. 2009;(191):71-92. doi: 10.1007/978-3-540-68964-5_5.
Chalimoniuk "Upregulation of guanylyl cyclase expression and activity in striatum of MPTP-induced parkinsonism in mice" *Biochem Biophys Res Commun*. Nov. 5, 2004;324(1):118-26.
Kakkar, et al. "Calmodulin-dependent cyclic nucleotide phosphodiesterase (PDE1)" *Cell Mol Life Sci*. Jul. 1999;55(8-9):1164-86.
Kakkar, et al. "Amantadine: an antiparkinsonian agent inhibits bovine brain 60 kDa calmodulin-dependent cyclic nucleotide phosphodiesterase isozyme", *Brain Res*. Feb. 28, 1997;749(2):290-4.
Hulley et al., "Cyclic AMP promotes the survival of dopaminergic neurons in vitro and protects them from the toxic effects of MPP+" *J Neural Transm Suppl*. (1995); 46:217-28.
Laddha et al., "A new therapeutic approach in Parkinson's disease: Some novel quinazoline derivatives as dual selective phosphodiesterase 1 inhibitors and anti-inflammatory agents" *Bioorganic & Medicinal Chemistry* (2009), 17(19), 6796-6802.
Kakkar, et al., "Inhibition of Bovine Brain Calmodulin-Dependent Cyclic Nucleotide Phosphodiesterase Isozymes by Deprenyl", *Life Sciences*, vol. 59, No. 21, pp. 337-341 (1996).
Sharma, et al., "Regulation of Calmodulin-Stimulated Cyclic Nucleotide Phosphodiesterase (PDE1): Review", *International Journal of Molecular Medicine*, 18: 95-105 (2006).
Blokland, "PDE Inhibition and Cognition Enhancement", vol. 22 No. 4, pp. 349-354 (2012) (Abstract Only).
Chen et al., Effects of Bimatoprost 0.03% on Ocular Hemodynamics in Normal Tension Glaucoma; Journal of Ocular Pharmacology and Therpaeutics, vol. 22, No. 3, 2006.
Noguchi et al; "A Facile Preparation of 7-(substituted amino-)-6H-pyrrolo[3,4-d]-pyrimidine Derivatives"; Bulletin Chem. Soc. of Japan, 62(9), 3043-5; (1989).
Ennaceur et al., "A New One-Trial Test for Neurobiological Studies of Memory in Rats. 1:Behavioral Data", *Behavioural Brain Research* (1998) 31:47-59.
Prickaerts et al., "Possible Role of Nitric Oxide-Cyclic GMP Pathway in Object Recognition Memory: Effects of 7-Nitroindazole and Zaprinast", *European Journal of Pharmacology*, (1997) 337:125-136.
Halene et al., "Antipsychotic-Like Properties of Phosphodiesterase 4 Inhibitors: Evaluation of 4-(3-Butoxy-4-methoxybenzyl)-2-imidazolidinone (RO-20-1724) with Auditory Event-Related Potentials and Prepulse Inhibition of Startle", J. Pharmacol. Exp. Ther., (2008) vol. 326, No. 1, pp. 230-239.
Pardo, C., et al., "Synthesis of 1-(p-Nitrobenzyl)azoles and 1-(p-Nitrobenzyl)benzazoles" (2000), OPPI Briefs, vol. 32, No. 4, pp. 385-390.
Medina. "Therapeutic Utility of Phosphodiesterase Type 1 Inhibitors in Neurological Conditions", Front. Neurosci. 5: 21, 6 pages, (2011).
Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).

\* cited by examiner

US 9,468,637 B2

ORGANIC COMPOUNDS

This application is a United States Application under 35 USC §371 claiming benefit of PCTUS/2010/001444 filed May 13, 2010, which claims priority from U.S. Provisional Application No. 61/178,035, filed May 13, 2009, the contents of each of which are incorporated by reference in their entirety.

TECHNICAL FIELD

The present invention relates to a new use for compounds that inhibit phosphodiesterase 1 (PDE1), e.g., that inhibit PDE1-mediated suppression of the dopamine D1 receptor intracellular pathway, specifically for the treatment of psychosis, e.g., in schizophrenia, schizoaffective disorder, schizophreniform disorder, psychotic disorder, delusional disorder, mania, or bipolar disorder.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases downregulate intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB).

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. For example, inhibition of PDE1B may potentiate the effect of a dopamine D1 agonist by protecting cGMP and cAMP from degradation, and similarly inhibit dopamine D2 receptor signaling pathways, by inhibiting PDE1 activity. PDE1 inhibitors are therefore potentially useful in diseases characterized by reduced dopamine D1 receptor signaling activity. See generally, WO 03/020702.

EP 0201188 and EP 0911333, the contents of which are incorporated herein by reference, disclose certain 1,3,5,-substituted, 6,7-dihydro-1H-pyrazolo[4,3-d]pyrimidin-7-one compounds, claimed to be useful for treatment of cardiovascular disease, erectile dysfunction, and other disorders. These compounds are not, however, taught or suggested to be useful for the treatment of schizophrenia. PCT/US2006/33179, the contents of which are incorporated herein by reference, discloses the use of 1,3,5,-substituted, 6,7-dihydro-1H-pyrazolo[4,3-d]pyrimidin-7-one compounds for treatment of diseases involving disorders of the dopamine D1 receptor intracellular pathway, but does not specifically disclose the use of such compounds in the treatment schizophrenia. PCT/US2006/022066, the contents of which are incorporated herein by reference, discloses PDE1 inhibitors which are 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, but does not specifically disclose their use for the treatment of schizophrenia. WO 03/042216, U.S. Pat. No. 5,939,419, EP 0 538 332, U.S. Pat. No. 5,393,755, U.S. Pat. No. 6,969,719 B2, Xia et al., J. Med. Chem. (1997), 40, 4372-4377 and Ahn et al., J. Med. Chem. (1997), 40, 2196-2210, the contents of all of which are incorporated herein by reference, disclose PDE1 cGMP phosphodiesterase inhibitors which are substituted pyrazolo[3,4-d]pyrimidine, pyrimido[2,1-b]purin-4-one and imidazo[2,1-b]purin-4-one analogues useful for the treatment of hypertensive, cardiovascular, sexual dysfunction and other cGMP-PDEV related disorders, but do not specifically disclose their use for the treatment of schizophrenia.

Increased dopamine activity in the mesolimbic pathway of the brain is consistently found in schizophrenic individuals. The mainstay of treatment is antipsychotic medication; this type of drug is believed to work primarily by suppressing dopamine activity. This is supported by the fact that many dopaminergic medications for Parkinson's disease, for example dopamine agonists such as bromocriptine or dopamine precursors such as levodopa, may cause hallucinations. Although PDE1 inhibitors have been suggested to help improve the cognitive impairment of schizophrenia, it has not been suggested that they would be useful as antipsychotics. On the contrary, as PDE1 inhibitors enhance dopamine D1 signaling, and antipsychotic drugs are believed to work by suppressing dopamine activity, it might well be thought that PDE1 inhibitors could exacerbate the problem.

SUMMARY OF THE INVENTION

It has now surprisingly been discovered that PDE1 inhibitors are useful to treat psychosis, for example conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder.

Without intending to be bound by theory, it is believed that typical and atypical antipsychotic drugs such as clozapine primarily have their antagonistic activity at the dopamine D2 receptor. PDE1 inhibitors, however primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

PDE1 inhibitors useful in the present invention are described more fully below. They include for example (i) optionally substituted 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form, e.g., as described in WO/2006/133261 the contents of which application are incorporated herein by reference, and (ii) 2-(optionally hetero)arylmethyl-3-(optionally hetero)arylamino-[2H]-pyrazolo[3,4-d]pyrimidine-4,6(5H,7H)-diones, in free, salt or prodrug form, wherein the (optionally)hetero aryl moiety at the 2-position is preferably benzyl or pryidyl methyl para-substituted relative to the point of attachment with aryl or heteroaryl, e.g., substituted with phenyl, pyridyl or thiadiazolyl, and the 1- or 2-position substituent is preferably substituted benzyl or pyridylmethyl, e.g. para-substituted relative to the point of attachment, e.g., with aryl, e.g., phenyl, or heteroaryl, e.g., pyridyl or thiadiazolyl, e.g., as disclosed in WO/2007/143705, the contents of which application are incorporated herein by reference.

(iii) 1,3,5,-substituted, 6,7-dihydro-1H-pyrazolo[4,3-d]pyrimidin-7-one compounds as disclosed in EP 0201188 and EP 0911333, the contents of which are incorporated herein by reference.

(iv) 1- or 2-substituted (6aR*,9aS*)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one compounds, preferably 1- or 2-substituted (6aR,9aS)-3-(phenylamino)-5-6a,7,8,9,9a-hexahydro-5-methyl-cyclopent[4,5]imidazo[1,2-a]pyrazolo[4,3-e]pyrimidin-4(1H or 2H)-ones, more preferably at the 2-position is a benzyl group substituted with an aryl (e.g., phenyl), heteroaryl (e.g., pyrid-2-yl), or $C_{3-7}$cycloalkyl optionally containing at least one atom selected from a group consisting of N or O, which aryl, heteroaryl and $C_{3-7}$cycloalkyl moiety are optionally substituted with halo, e.g., benzyl substituted with aryl, heteroaryl, for example benzyl substituted with 6-fluoropyrid-2-yl, in free or salt form as disclosed in WO/2009/075784, the contents of which are incorporated herein by reference.

(v) 1- or 2- or 7-(substituted)-3-(optionally hetero)arylamino-[1H, 2H]-pyrazolo[3,4-d]pyrimidine-4,6(5H, 7H)-diones, preferably at the 2-position is a benzyl group substituted with aryl (e.g., phenyl), heteroaryl (e.g., pyrid-2-yl, 1,2,4-triazolyl) or heteroC$_{3-6}$cycloalkyl (e.g., pyrrolidin-1-yl) optionally substituted with $C_{1-6}$alkyl (e.g., methyl), for example, benzyl optionally substituted with pyrrolidin-1-yl, pyrrolidin-2-yl, 1-methylpyrrolidin-2-yl, piperidin-2-yl, 1-methylpiperidin-2-yl, 1-ethylpiperidin-2-yl, in free or salt form as disclosed in WO/2009/073210, the contents of which are incorporated herein by reference.

The invention thus provides a new method of treatment for psychosis, e.g., schizophrenia, comprising administering an effective amount of a phosphodiesterase-1 (PDE1) inhibitor to a patient in need thereof. PDE1 inhibitors include, for example, 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, substituted at the 1 or 2 position with $C_{2-9}$ alkyl or $C_{3-9}$ cycloalkyl, or optionally substituted heteroarylalkyl or substituted arylalkyl, in free, salt or prodrug form (hereinafter a PDE 1 Inhibitor, e.g., as described below) or a 1,3,5-substituted 6,7-dihydro-1H-pyrazolo[4,3-d]pyrimidin-7-one, in free, salt or prodrug form (also included in PDE1 Inhibitors, e.g., as described below).

In another embodiment, PDE1 inhibitors include 1- or 2-substituted (6aR*,9aS*)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one compounds as disclosed below, for example (6aR,9aS)-5,6a,7,8,9,9a-hexahydro-5-methyl-3-(phenylamino)-2-(4-(6-fluoropyridin-2-yl)phenyl)methyl)-cyclopent[4,5]imidazo[1,2-a]pyrazolo[4,3-e]pyrimidin-4(2H)-one, in free or salt form.

In still another embodiment, PDE1 inhibitors include 1- or 2- or 7-(substituted)-3-(optionally hetero)arylamino-[1H, 2H]-pyrazolo[3,4-d]pyrimidine-4,6(5H, 7H)-diones as disclosed below, for example 7-isopropyl-5-methyl-3-(phenylamino)-2-(4-(pyridin-2-yl)benzyl)-2H-pyrazolo[3,4-d]pyrimidine-4,6(5H,7H)-dione or 7-Isobutyl-5-methyl-3-(phenylamino)-2-(4-(piperidin-2-yl)benzyl)-2H-pyrazolo[3,4-d]pyrimidine-4,6(5H,7H)-dione, in free or salt form.

PDE1 inhibitors also include, for example, substituted imidazo[2,1-b]purin-4-one, e.g., (6aR,9aS)-2-(biphenyl-4-ylmethyl)-5,6a,7,8,9,9a-hexahydro-5-methyl-3(phenylmethyl)-cyclopent-[4,5]imidazo-[2,1-b]purin-4(3H)-one, (6aR,9aS)-5,6a,7,8,9,9a-hexahydro-5-methyl-2,3-bis(phenylmethyl)cyclopent-[4,5]imidazo-[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one, or 5'-methyl-2'-(biphenylylmethyl)-3'-(phenylmethyl)spiro[cyclopentane-1,7'(8'H)-[3H]imidazo[2,1-b]purin]-4'(5'H)-one as described in Ahn et al., *J. Med. Chem.* (1997), 40, 2196-2210 (hereinafter a PDE 1 Inhibitor, e.g., as described below).

These compounds are found to selectively inhibit phosphodiesterase 1 (PDE1) activity, especially PDE1B activity, and to be useful in the treatment and prophylaxis of schizophrenia. These compounds are found to selectively inhibit phosphodiesterase 1 (PDE1) activity, especially PDE1B activity, and to be useful in the treatment and prophylaxis of schizophrenia.

DETAILED DESCRIPTION OF THE INVENTION

Compounds for Use in the Methods of the Invention

Preferably, the PDE 1 Inhibitors for use in the methods of treatment described herein are a 7,8-dihydro-[1H or 2H]-imidazo[1,2-a]pyrazolo[4,3-e]pyrimidin-4(5H)-ones or 7,8,9-trihydro-[1H or 2H]-pyrimido[1,2-a]pyrazolo[4,3-e]pyrimidin-4(5H)-ones, of formula I

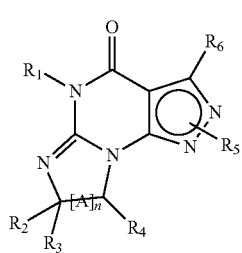

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl
or
$R_5$ is attached to one of the nitrogen atoms on the pyrazolo portion of Formula I
and is a moiety of Formula Q

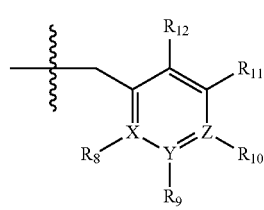

Formula Q wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1;
(vi) when n=1, A is —($R_{13}R_{14}$)—
wherein $R_{13}$ and $R_{14}$, are, independently, H or $C_{1-4}$ alkyl, aryl, heteroaryl,
(optionally hetero)arylalkoxy or (optionally hetero)arylalkyl;

in free, salt or prodrug form, including its enantiomers, diasterisomers and racemates.

The invention further provides the use of PDE 1 Inhibitors of Formula I as follows:

1.1 Formula I wherein $R_1$ is methyl and n=0;

1.2 Formula I or 1.1 wherein $R_4$ is H or $C_{1-4}$ alkyl and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;

1.3 Formula I or 1.1 wherein $R_4$ is H and at least one of $R_2$ and $R_3$ is arylalkoxy;

1.4 Formula I wherein $R_1$ is methyl, $R_2$, $R_3$, and $R_4$ are H, n=1, and $R_{13}$ and $R_{14}$ are, independently, H or $C_{1-4}$ alkyl (e.g., methyl or isopropyl);

1.5 Formula I or 1.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;

1.6 Formula I, 1.1 or 1.5 wherein $R_5$ is a substituted heteroarylmethyl, e.g., para-substituted with haloalkyl;

1.7 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is phenyl;

1.8 Formula I, 1.1, 1.2, 1.3, 1.4 or 1.5 wherein $R_5$ is a moiety of Formula Q wherein $R_8$, $R_9$, $R_{11}$, and $R_{12}$ are H and $R_{10}$ is pyridyl or thiadiazolyl;

1.9 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H or halogen, and $R_{10}$ is haloalkyl;

1.10 Formula I, 1.1, 1.2, 1.3, 1.4 or 1.5 wherein $R_5$ is a moiety of Formula Q wherein $R_8$, $R_9$, $R_{11}$, and $R_{12}$ are, independently, H, and $R_{10}$ is alkyl sulfonyl;

1.11 any of the preceding formulae wherein $R_5$ is attached to the 2-position nitrogen on the pyrazolo ring;

1.12 any of the preceding formulae wherein $R_6$ is benzyl;

1.13 any of the preceding formulae wherein $R_6$ is phenylamino or phenylalkylamino (e.g., benzylamino);

1.14 any of the preceding formulae wherein $R_6$ is phenylamino;

1.15 any of the preceding formulae wherein X, Y, and Z are all C, 1.16 any of the preceding formulae wherein X, Y, and Z are all C and $R_{10}$ is phenyl or 2-pyridyl; and/or 1.17 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;

in free or salt form.

For example, the PDE 1 Inhibitors include 7,8-dihydro-[1H or 2H]-imidazo[1,2-a]pyrazolo[4,3-e]pyrimidin-4(5H)-ones of Formula Ia

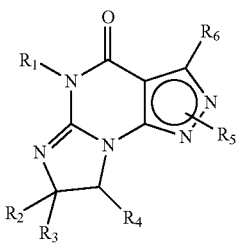

Formula Ia wherein
(i) $R_1$ is H or $C_{1-4}$ alkyl [e.g., methyl];
(ii) $R_4$ is H and $R_2$ and $R_3$ are, independently, H or $C_{1-4}$ alkyl [e.g., $R_2$ and $R_3$ are both methyl, or $R_2$ is H and $R_3$ is isopropyl], aryl, or arylalkyl;
or $R_2$ is H and $R_3$ and $R_4$ together form a di-, tri- or tetramethylene bridge [pref. wherein the $R_3$ and $R_4$ have the cis configuration, e.g., where the carbons carrying $R_3$ and $R_4$ have the R and S configurations respectively];
(iii) $R_5$ is attached to one of the nitrogen atoms on the pyrazolo portion of formula Ia and is a substituted benzyl of formula Qa

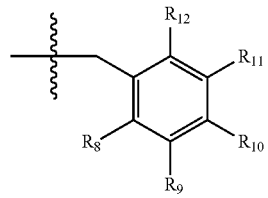

Formula Qa wherein $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), arylcarbonyl (e.g., benzoyl), alkyl sulfonyl or heteroarylcarbonyl; and
(iv) $R_6$ is H, alkyl, aryl, heteroaryl, arylalkyl [e.g., benzyl], arylamino [e.g., phenylamino], heteroarylamino, arylalkylamino, N,N-dialkylamino, N,N-diarylamino, or N-aryl-N-(arylalkyl)amino [e.g. N-phenyl-N-(1,1'-biphen-4-ylmethyl)amino];
in free, salt or prodrug form.

The invention further provides the use of PDE 1 Inhibitors of Formula Ia as follows:
2.1: Formula Ia wherein $R_1$ is methyl;
2.2: Formula Ia or 2.1 wherein $R_4$ is H and at least one of $R_2$ and $R_3$ is lower alkyl, such that when the carbon carrying $R_3$ is chiral, it has the R configuration, e.g., wherein both $R_2$ and $R_3$ are methyl, or wherein one is hydrogen and the other isopropyl;
2.3: Formula Ia or 2.1 wherein $R_2$ is H and $R_3$ and $R_4$ together form a tri- or tetramethylene bridge, having the cis configuration, preferably wherein the carbons carrying $R_3$ and $R_4$ have the R and S configurations respectively;
2.4: Formula Ia, 2.1, 2.2 or 2.3 wherein $R_5$ is a moiety of formula Qa wherein $R_8$, $R_9$, $R_{11}$, and $R_{12}$ are H and $R_{10}$ is phenyl;
2.5: Formula Ia, 2.1, 2.2, or 2.3 wherein $R_5$ is a moiety of formula Qa wherein $R_8$, $R_9$, $R_{11}$, and $R_{12}$ are H and $R_{10}$ is pyridyl or thiadiazolyl;
2.6: Formula Ia, 2.1, 2.2, 2.3, 2.4, or 2.5 wherein $R_5$ is attached to the 2-position nitrogen on the pyrazolo ring;
2.7: Formula Ia, 2.1, 2.2, 2.3, 2.4, 2.5 or 2.6 wherein $R_6$ is benzyl;
2.8: Formula Ia, 2.1, 2.2, 2.3, 2.4, 2.5 or 2.6 wherein $R_6$ is phenylamino or phenylalkylamino (e.g., benzylamino); and/or
2.9: Formula Ia, 2.1, 2.2, 2.3, 2.4, 2.5, 2.6, 2.7, or 2.8 wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1;
in free or salt form.

In an another embodiment, the PDE 1 Inhibitors are compounds of Formula I wherein
(i) $R_1$ is methyl;
(ii) $R_2$, $R_3$ and $R_4$ are H;
(iii) n=1 and $R_a$ and $R_b$ are, independently, H or methyl;
(iv) $R_5$ is a moiety of Formula Q wherein $R_8$, $R_9$, $R_{11}$ and $R_{12}$ are H and $R_{10}$ is phenyl, pyridyl (for example pyrid-2-yl), or thiadiazolyl (e.g., 1,2,3-thiadiazol-4-yl);
(v) $R_6$ is benzyl, phenylamino or benzylamino;
in free or salt form.

In another embodiment, the PDE 1 Inhibitors are compounds of Formula I wherein
(i) $R_1$ is methyl;
(ii) n=0;
(iii) $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
(iv) $R_5$ is a substituted heteroarylmethyl, e.g., para-substituted with haloalkyl; or
$R_5$ is a moiety of Formula Q wherein $R_8$, $R_9$, $R_{11}$ and $R_{12}$ are H or halogen and $R_{10}$ is haloalkyl, phenyl, pyridyl (for example pyrid-2-yl), or thiadiazolyl (e.g., 1,2,3-thiadiazol-4-yl); and
(v) $R_6$ is benzyl, phenylamino or benzylamino;
in free or salt form.

In another embodiment, the PDE 1 Inhibitors are compounds of Formula Ia wherein
(i) $R_1$ is methyl;
(ii) $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];
(iii) $R_5$ is a moiety of Formula Qa wherein $R_8$, $R_9$, $R_{11}$, and $R_{12}$ are H and $R_{10}$ is haloalkyl, phenyl, pyridyl (for example pyrid-2-yl), or thiadiazolyl (e.g., 1,2,3-thiadiazol-4-yl); and
(iv) $R_6$ is benzyl, phenylamino or benzylamino;
in free or salt form.

In another embodiment, the PDE 1 Inhibitors are compounds of Formula Ia selected from the following:

Compound 1

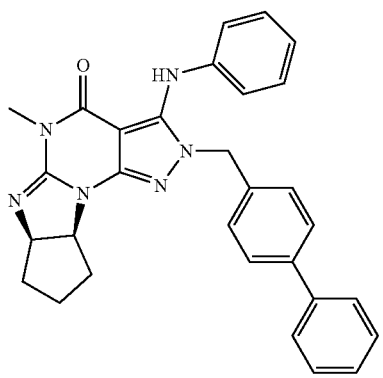

Compound 2

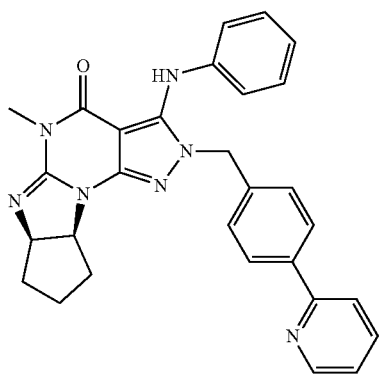

For example, PDE 1 Inhibitors include compounds according to Formulae II, III and IV.

Formula II

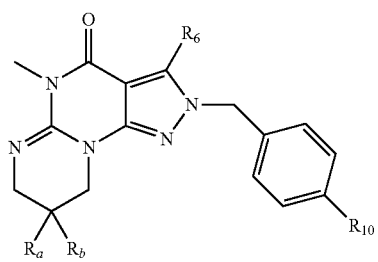

wherein
- $R_a$ and $R_b$ are, independently, H or $C_{1-4}$ alkyl;
- $R_6$ is phenylamino or benzylamino;
- $R_{10}$ is phenyl, pyridyl (for example pyrid-2-yl), or thiadiazolyl (e.g., 1,2,3-thiadiazol-4-yl);
- in free or salt form.

Formula III

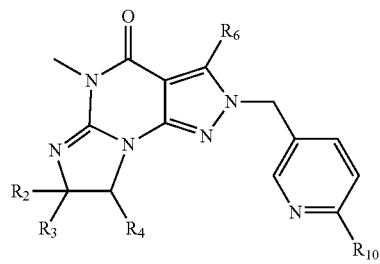

wherein
- $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
- $R_6$ is phenylamino or benzylamino;
- $R_{10}$ is haloalkyl, phenyl, pyridyl (for example pyrid-2-yl), or thiadiazolyl (e.g., 1,2,3-thiadiazol-4-yl);
- in free or salt form.

Formula IV

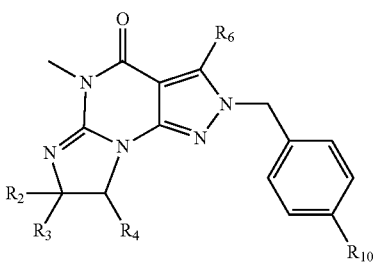

wherein
- $R_2$ is H and $R_3$ and $R_4$ together form a tri- or tetra-methylene bridge [pref. with the carbons carrying $R_3$ and $R_4$ having the R and S configuration respectively]; or at least one of $R_2$ and $R_3$ is methyl, isopropyl or arylalkoxy and $R_4$ is H; or $R_2$ and $R_3$ are H and $R_4$ is a $C_{1-4}$ alkyl;
- $R_6$ is phenylamino or benzylamino;
- $R_{10}$ is phenyl, pyridyl (for example pyrid-2-yl), or thiadiazolyl (e.g., 1,2,3-thiadiazol-4-yl);
- in free or salt form.

PDE 1 Inhibitors used in the method disclosed herein also include compounds according to Formula V:

Formula V wherein
- R$_2$ is H and R$_3$ and R$_4$ together form a tri- or tetramethylene bridge [pref. with the carbons carrying R$_3$ and R$_4$ having the R and S configuration respectively]; or R$_2$ and R$_3$ are each methyl and R$_4$ is H; or R$_2$ and R$_4$ are H and R$_3$ is isopropyl [pref. the carbon carrying R$_3$ having the R configuration];
- R$_6$ is phenylamino or benzylamino;
- R$_{10}$ is phenyl, pyridyl, or thiadiazolyl;
in free or salt form.

In still another embodiment, the PDE 1 Inhibitors for use in the methods of treatment described herein are 1- or 2-substituted (6aR*,9aS*)-3-(phenylamino)-5-6a,7,8,9,9a-hexahydro-5-methyl-cyclopent[4,5]imidazo[1,2-a]pyrazolo[4,3-e]pyrimidin-4(1H or 2H)-one of Formula XII:

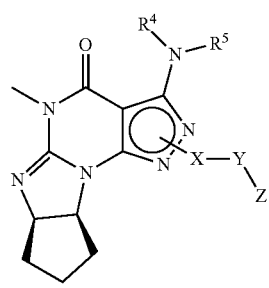

Formula XII wherein
- (i) X is C$_{1-6}$alkylene (e.g., methylene, ethylene or prop-2-yn-1-ylene);
- (ii) Y is a single bond, alkynylene (e.g., —C≡C—), arylene (e.g., phenylene) or heteroarylene (e.g., pyridylene);
- (iii) Z is H, aryl (e.g., phenyl), heteroaryl (e.g., pyridyl, e.g., pyrid-2-yl), halo (e.g., F, Br, Cl), haloC$_{1-6}$alkyl (e.g., trifluoromethyl), —C(O)—R$^1$, —N(R$^2$)(R$^3$), or C$_{3-7}$cycloalkyl optionally containing at least one atom selected from a group consisting of N or O (e.g., cyclopentyl, cyclohexyl, tetrahydro-2H-pyran-4-yl, or morpholinyl);
- (iv) R$^1$ is C$_{1-6}$alkyl, haloC$_{1-6}$alkyl, —OH or —OC$_{1-6}$alkyl (e.g., —OCH$_3$);
- (v) R$^2$ and R$^3$ are independently H or C$_{1-6}$alkyl;
- (vi) R$^4$ and R$^5$ are independently H, C$_{1-6}$alky or aryl (e.g., phenyl) optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl);
- (vii) wherein X, Y and Z are independently and optionally substituted with one or more halo (e.g., F, Cl or Br), C$_{1-6}$alkyl (e.g., methyl), haloC$_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-6}$alkyl (e.g., 5-trifluoromethylpyrid-2-yl) or C$_{1-6}$alkyl (e.g., 5-methylpyrid-2-yl), or Z is aryl, e.g., phenyl, substituted with one or more halo (e.g., 4-fluorophenyl), in free, salt or prodrug form, provided that when X is an unsubstituted methylene, Y is phenylene or heteroarylene, and Z is aryl, heteroaryl, haloalkyl or cycloalkyl, then Z is substituted with at least one halo (e.g., fluoro, chloro, bromo) or alkyl (e.g., methyl, ethyl) group.

In yet another embodiment, the PDE 1 Inhibitor of Formula XII for use in the methods of treatment described herein is selected from any of the following:

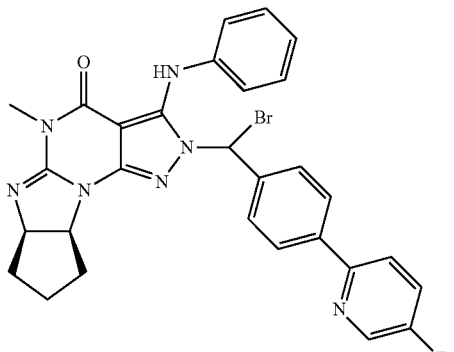

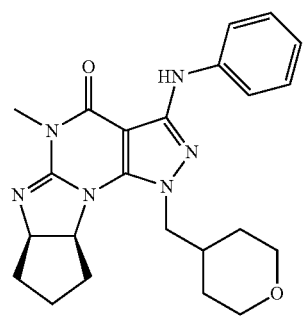

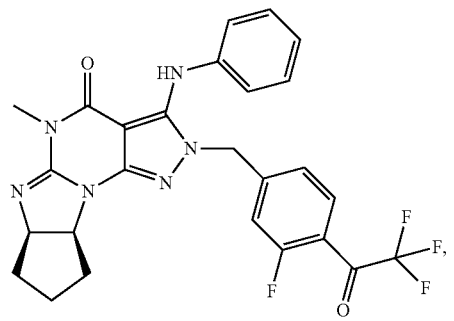

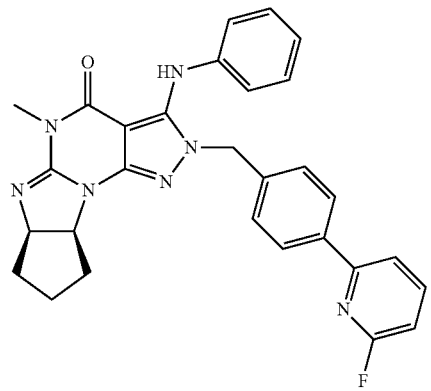

-continued
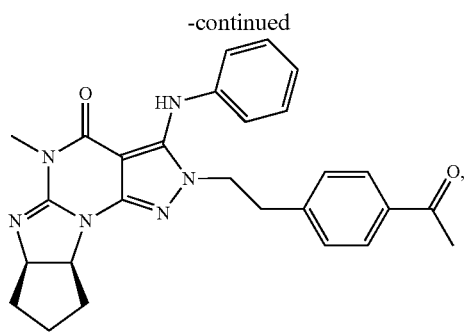
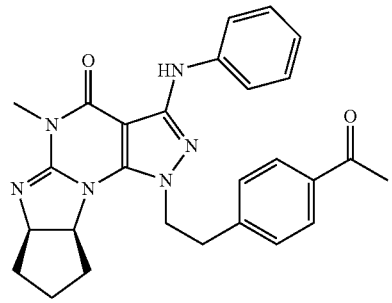
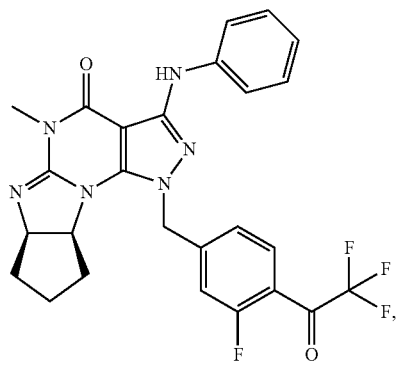
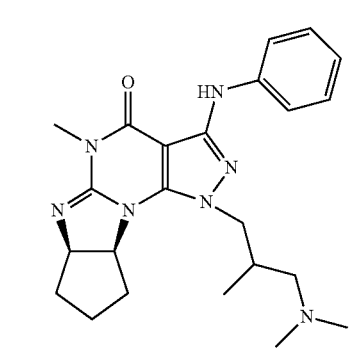
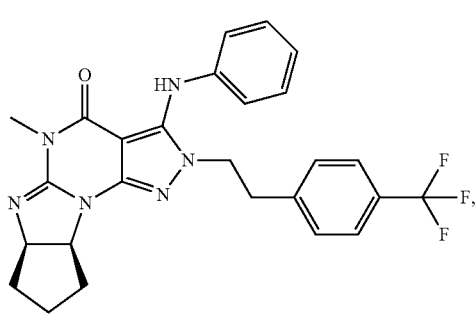
-continued
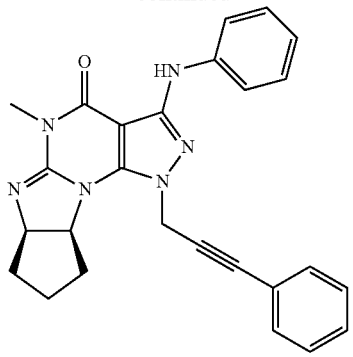
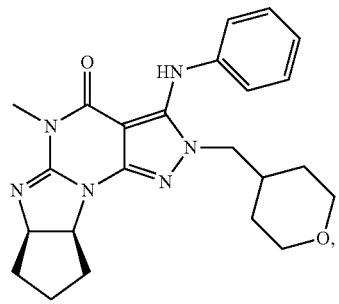
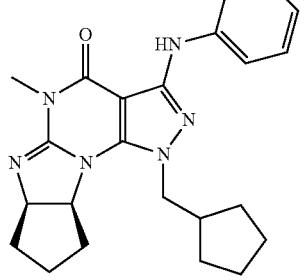
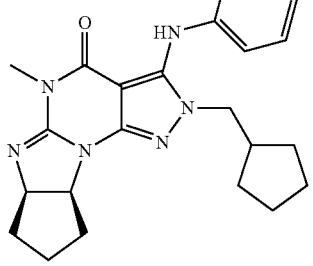
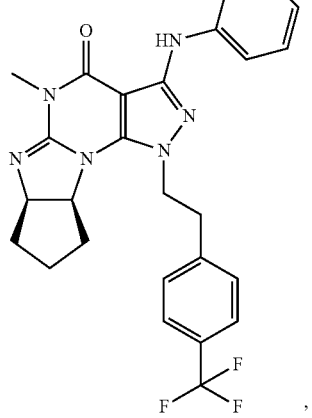

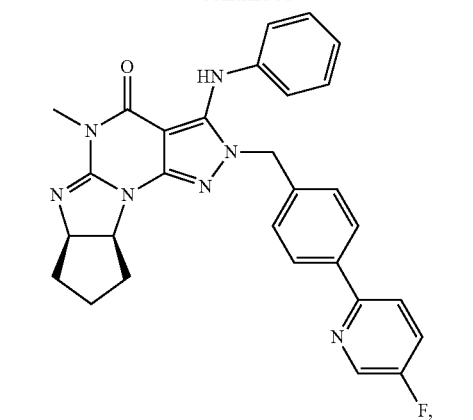
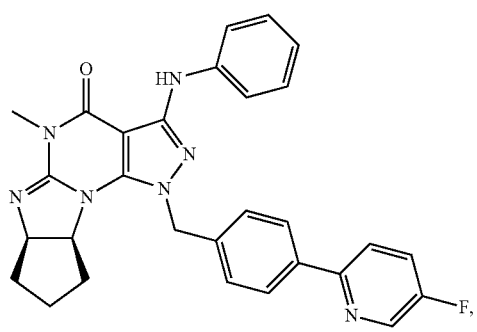
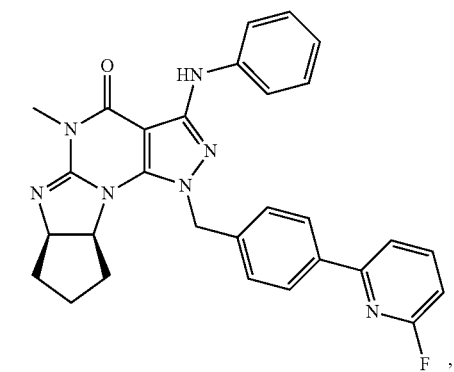
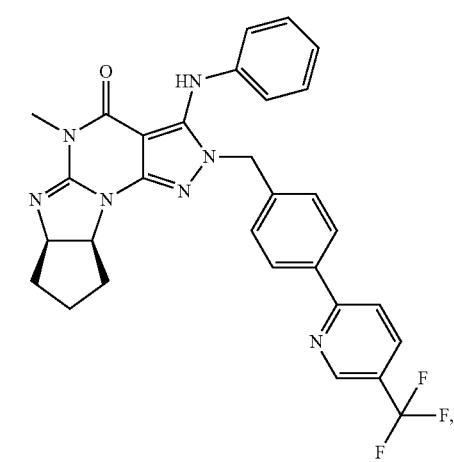
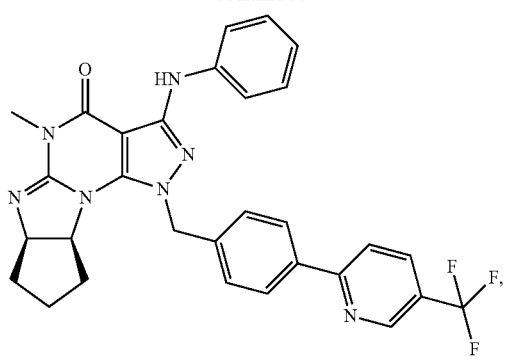
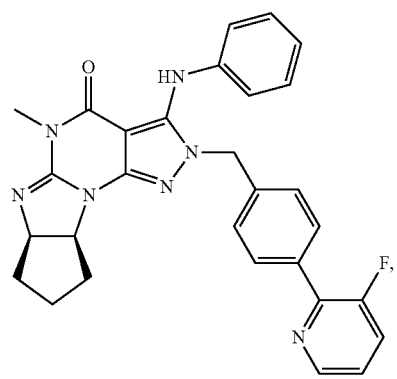
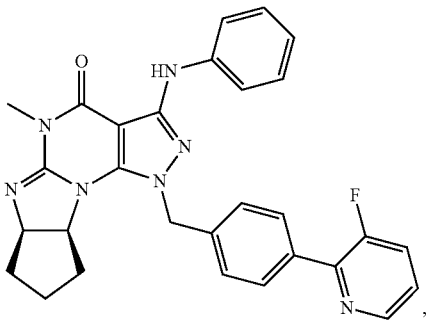
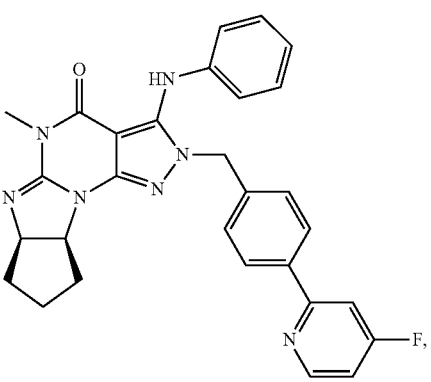

17
-continued
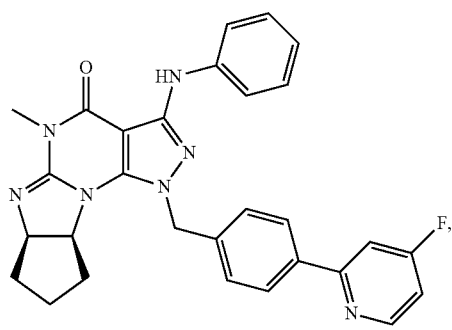
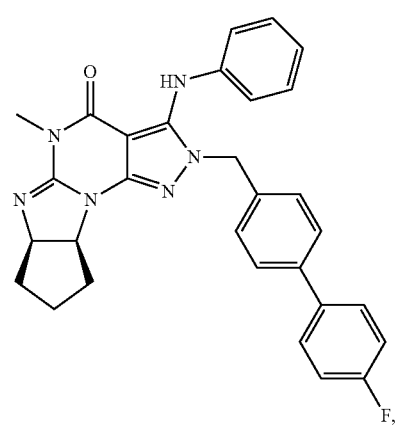
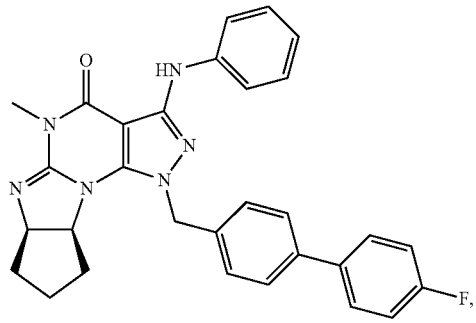
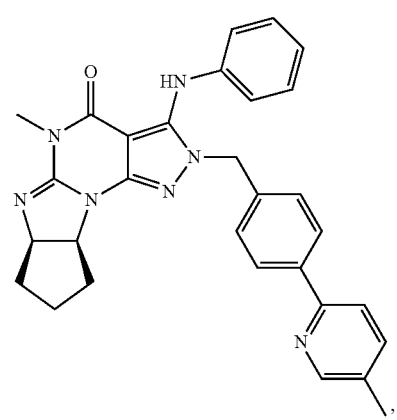
18
-continued
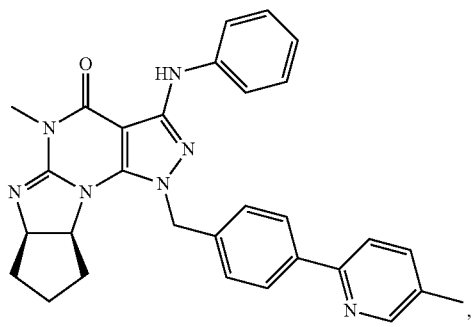
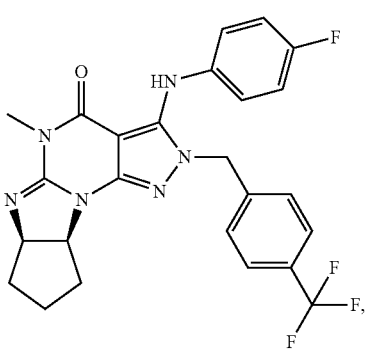
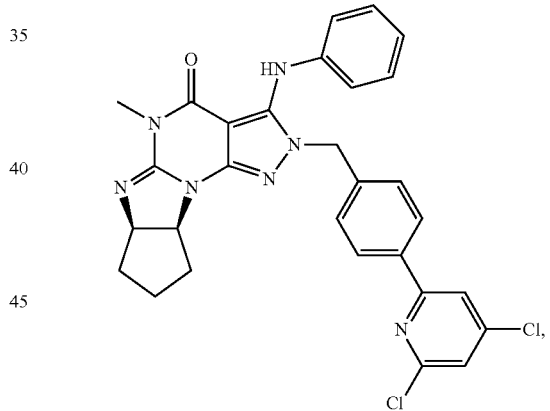
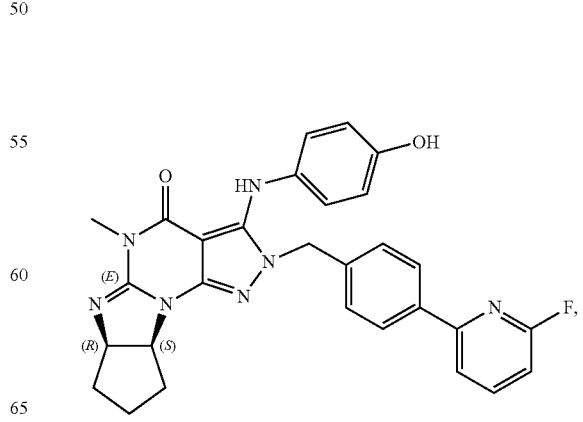

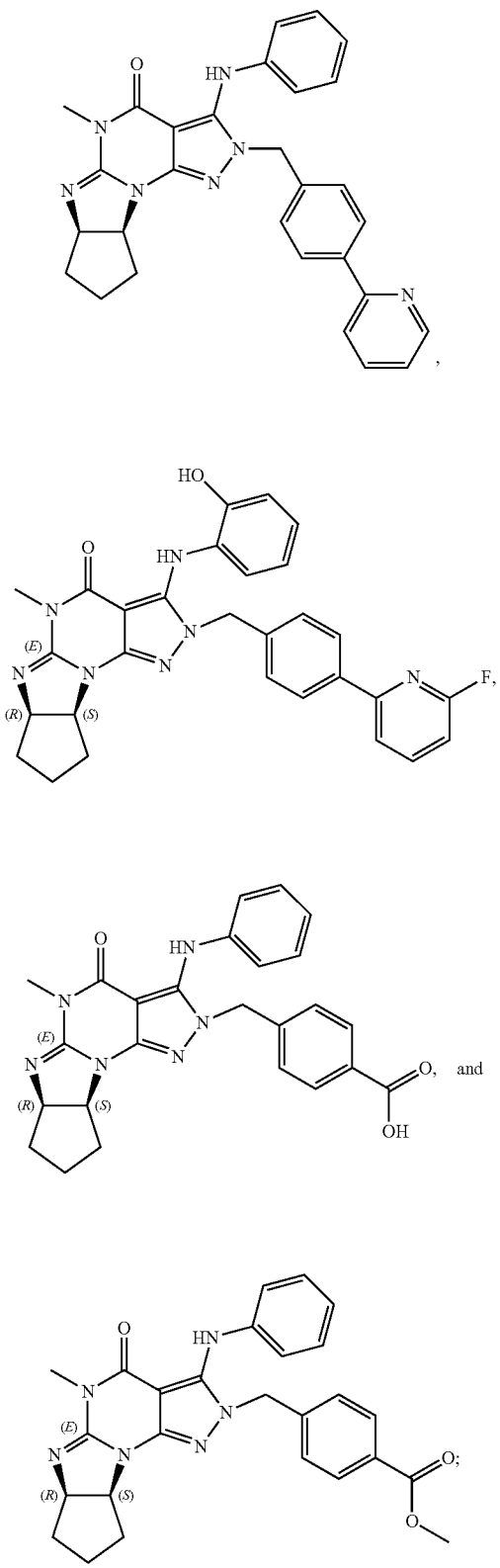

in free or salt form.

In yet another embodiment, the PDE 1 Inhibitors for use in the methods of treatment described herein are compounds of Formula XIII:

Formula XIII wherein
(i) X is $C_{1-4}$alkylene (e.g., methylene, ethylene or prop-2-yn-1-ylene);
(ii) Y is a single bond, alkynylene (e.g., —C≡C—), arylene (e.g., phenylene) or heteroarylene (e.g., pyridylene);
(iii) Z is H, aryl (e.g., phenyl), heteroaryl (e.g., pyrid-2-yl), halo (e.g., F, Br, Cl), halo$C_{1-4}$alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl);
(iv) $R^1$ is $C_{1-4}$alkyl, halo$C_{1-4}$alkyl;
(v) $R^2$ and $R^3$ are independently H or $C_{1-4}$alkyl,
(vi) wherein X, Y and Z are independently and optionally substituted with halo (e.g., F, Cl or Br), for example, Z is pyrid-2-yl substituted with fluoro (e.g., 6-fluoropyrid-2-yl), in free, salt or prodrug form, including its enantiomers, diastereoisomers and racemates.

In yet another embodiment, the PDE 1 Inhibitors for use in the methods of treatment described herein are compounds of Formula XIV:

Formula XIV wherein
(i) $R_1$ is H or $C_{1-6}$ alkyl (e.g., methyl);
(ii) $R_4$ is H or $C_{1-6}$ alkyl and $R_2$ and $R_3$ are, independently, H or $C_{1-6}$alkyl optionally substituted with halo or hydroxyl (e.g., $R_2$ and $R_3$ are both methyl, or $R_2$ is H and $R_3$ is ethyl, isopropyl or hydroxyethyl), aryl, heteroaryl, (optionally hetero)arylalkoxy, or (optionally hetero)aryl$C_{1-6}$alkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(iii) R$_5$ is a substituted heteroarylC$_{1-6}$alkyl, e.g., substituted with C$_{1-6}$haloalkyl;

R$_5$ is -D-E-F, wherein:
D is C$_{1-6}$alkylene (e.g., methylene, ethylene or prop-2-yn-1-ylene);
E is a single bond, alkynylene (e.g., —C≡C—), arylene (e.g., phenylene) or heteroarylene (e.g., pyridylene);
F is H, aryl (e.g., phenyl), heteroaryl (e.g., pyridyl, e.g., pyrid-2-yl), halo (e.g., F, Br, Cl), haloC$_{1-6}$alkyl (e.g., trifluoromethyl), —C(O)—R$_{15}$, —N(R$_{16}$)(R$_{17}$), or C$_{3-7}$cycloalkyl optionally containing at least one atom selected from a group consisting of N or O (e.g., cyclopentyl, cyclohexyl, tetrahydro-2H-pyran-4-yl, or morpholinyl);
wherein D, E and F are independently and optionally substituted with one or more halo (e.g., F, Cl or Br), C$_{1-6}$alkyl (e.g., methyl), haloC$_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-6}$alkyl (e.g., 5-trifluoromethylpyrid-2-yl) or C$_{1-6}$alkyl (e.g., 5-methylpyrid-2-yl), or Z is aryl, e.g., phenyl, substituted with one or more halo (e.g., 4-fluorophenyl);

or

R$_5$ is attached to one of the nitrogens on the pyrazolo portion of Formula XIV and is a moiety of Formula A Formula A

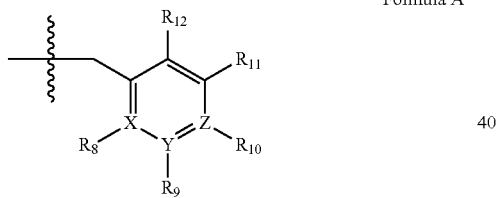

wherein X, Y and Z are, independently, N or C, and R$_8$, R$_9$, R$_{11}$ and R$_{12}$ are independently H or halogen (e.g., Cl or F), and R$_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, R$_8$, R$_9$, or R$_{10}$, respectively, is not present; and (iv) R$_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino);

or

R$_6$ is —N(R$_{18}$)(R$_{19}$) wherein R$_{18}$ and R$_{19}$ are independently H, C$_{1-6}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl);

(v) n=0 or 1;
(vi) when n=1, A is —C(R$_{13}$R$_{14}$)—;
(vii) wherein R$_{13}$ and R$_{14}$, are, independently, H or C$_{1-6}$alkyl, aryl, heteroaryl, (optionally hetero)arylalkoxy or (optionally hetero)arylalkyl;
(viii) R$_{15}$ is haloC$_{1-6}$alkyl, —OH or —OC$_{1-6}$alkyl (e.g., —OCH$_3$);
(ix) R$_{16}$ and R$_{17}$ are independently H or C$_{1-6}$alkyl;

in free, salt or prodrug form.

In yet another embodiment, the PDE 1 Inhibitor of Formula XIV for use in the methods of treatment described herein is:

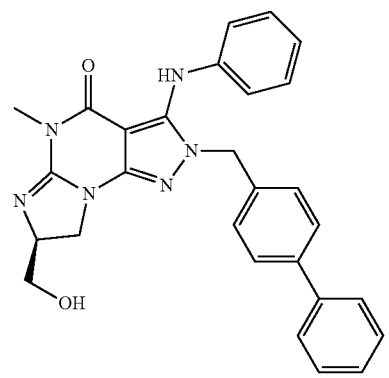 [SMILES: CN1C(=O)c2c(nn(Cc3ccc(-c4ccccc4)cc3)c2Nc2ccccc2)N2C[C@@H](CO)N=C12]

in free, salt or prodrug from.

In yet another embodiment, the PDE 1 Inhibitors for use in the methods of treatment described herein are compounds of Formula XV:

Formula XV

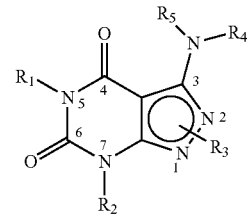

wherein
(i) R$_1$ is H or C$_{1-6}$alkyl (e.g., methyl);
(ii) R$_2$ is
H,
C$_{1-6}$alkyl (e.g., isopropyl, isobutyl, 2-methylbutyl, 2,2-dimethyl propyl),
C$_{3-8}$cycloalkyl (e.g., cyclopentyl, cyclohexyl) optionally substituted with one or more amino (e.g., —NH$_2$), for example, 2-aminocyclopentyl or 2-aminocyclohexyl),
C$_{3-8}$heterocycloalkyl (e.g., pyrrolidinyl, for example, pyrrolidin-3-yl) optionally substituted with C$_{1-6}$alkyl (e.g., methyl), for example, 1-methylpyrrolidin-3-yl,
C$_{3-8}$cycloalkyl-C$_{1-6}$alkyl (e.g., cyclopropylmethyl),
C$_{1-6}$haloalkyl (e.g., trifluoromethyl, 2,2,2-trifluoroethyl),
C$_{0-6}$alkylaminoC$_{0-6}$alkyl (e.g., 2-(dimethylamino) ethyl, 2-aminopropyl),
hydroxyC$_{1-6}$alkyl (e.g., 3-hydroxy-2-methylpropyl),
arylC$_{0-6}$alkyl (e.g., benzyl),
heteroarylalkyl (e.g., pyridylmethyl), $C_{1-6}$alkoxyaryl$C_{1-6}$alkyl (e.g., 4-methoxybenzyl), or -G-J wherein:
G is a single bond or, alkylene (e.g., methylene);
J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));

(iii) $R_3$ is
a) D-E-F wherein
1. D is single bond, $C_{1-6}$alkylene (e.g., methylene), or aryl$C_{1-6}$alkylene (e.g., benzylene or —$CH_2C_6H_4$—);
2. E is a $C_{1-6}$alkylene (e.g., methylene, ethynylene, prop-2-yn-1-ylene), arylene (e.g., phenylene or —$C_6H_4$—), $C_{1-6}$alkylarylene (e.g., -benzylene- or —$CH_2C_6H_4$—), amino$C_{1-6}$alkylene (e.g., —$CH_2N(H)$—) or amino (e.g., —N(H)—); and
3. F is
$C_{1-6}$alkyl (e.g., isobutyl, isopropyl),
aryl (e.g., phenyl),
heteroaryl (e.g., 1,2,4-triazolyl, imidazolyl, pyridyl) optionally substituted with $C_{1-6}$alkyl, for example, pyrid-2-yl, imidazol-1-yl, 4-methyl imidazolyl, 1-methylimidazol-2-yl, 1,2,4-triazol-1-yl,
hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
amino (e.g., —$NH_2$),
$C_{1-6}$alkoxy, or
—O-halo$C_{1-6}$alkyl (e.g., —O—$CF_3$),
b) $R_3$ is a substituted heteroarylalkyl, e.g., substituted with $C_{1-6}$haloalkyl; or
c) $R_3$ is attached to one of the nitrogen atoms on the pyrazolo portion of Formula XV and is a moiety of Formula A

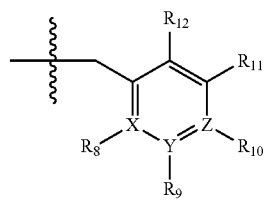

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl, $C_{3-8}$cycloalkyl, $C_{1-6}$haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), $C_{1-6}$alkoxadiazolyl (e.g., 5-methyl-1,2,4-oxadiazol), pyrazolyl (e.g., pyrazol-1-yl), $C_{1-6}$alkyl sulfonyl (e.g., methyl sulfonyl), arylcarbonyl (e.g., benzoyl), or heteroarylcarbonyl, $C_{1-6}$alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;
(iv) $R_4$ is aryl (e.g., phenyl) optionally substituted with one or more halo (e.g., F or Cl) or hydroxyl, heteroaryl (e.g., pyrid-4-yl, pyrid-2-yl or pyrazol-3-yl) or hetero$C_{3-6}$cycloalkyl (e.g., pyrrolidin-3-yl); and
(v) $R_5$ is H, $C_{1-6}$alkyl, $C_{3-8}$cycloalkyl (e.g., cyclopentyl), heteroaryl, aryl, p-benzylaryl (e.g., biphenyl-4-ylmethyl);
wherein "alk", "alkyl", "haloalkyl" or "alkoxy" refers to $C_{1-6}$ alkyl and "cycloalkyl" refers to $C_{3-8}$cycloalkyl;
in free, salt or prodrug form.

In yet another embodiment, the PDE 1 Inhibitors of Formula XV for use in the methods of treatment described herein are as follows:

15.1. Formula XV wherein, $R_1$ is H or $C_{1-6}$alkyl (e.g., methyl);
15.2. Formula XV wherein, $R_1$ is $C_{1-6}$alkyl (e.g., methyl);
15.3. Formula XV wherein, $R_1$ is methyl;
15.4. Formula XV or any of 1.1-15.3 wherein, $R_2$ is H; $C_{1-6}$alkyl (e.g., isopropyl, isobutyl, 2-methylbutyl, 2,2-dimethylpropyl); $C_{3-8}$cycloalkyl (e.g., cyclopentyl, cyclohexyl) optionally substituted with one or more amino (e.g., —$NH_2$), for example, 2-aminocyclopentyl or 2-aminocyclohexyl); $C_{3-8}$heterocycloalkyl (e.g., pyrrolidinyl, for example, pyrrolidin-3-yl) optionally substituted with $C_{1-6}$alkyl (e.g., methyl), for example, 1-methylpyrrolidin-3-yl; $C_{3-8}$cycloalkyl-$C_{1-6}$alkyl (e.g., cyclopropylmethyl); halo$C_{1-6}$alkyl (e.g., trifluoromethyl, 2,2,2-trifluoroethyl); $C_{0-6}$alkylamino$C_{0-6}$alkyl (e.g., 2-(dimethylamino)ethyl, 2-aminopropyl), hydroxy$C_{1-6}$alkyl (e.g., 3-hydroxy-2-methylpropyl); aryl$C_{0-6}$alkyl (e.g., benzyl), heteroarylalkyl (e.g., pyridylmethyl), or alkoxyarylalkyl (e.g., 4-methoxybenzyl); or -G-J wherein: G is a single bond or, alkylene (e.g., methylene) and J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
15.5. Formula XV or any of 1.1-15.4, wherein $R_2$ is H
15.6. Formula XV or any of 1.1-15.4, wherein $R_2$ is $C_{1-6}$ alkyl;
15.7. Formula 15.6 wherein, $R_2$ is isopropyl, isobutyl, 2,2-dimethylpropyl, or 2-methylbutyl;
15.8. Formula 15.6 wherein, $R_2$ is isobutyl;
15.9. Formula 15.6 wherein, $R_2$ is 2,2-dimethylpropyl;
15.10. Formula XV or any of 1.1-15.4, wherein $R_2$ is hydroxy$C_{1-6}$ alkyl;
15.11. Formula 15.10, wherein $R_2$ is 3-hydroxy-2-methylpropyl;
15.12. Formula XV or any of 1.1-15.4, wherein $R_2$ is $C_{1-6}$alkoxyaryl$C_{1-6}$alkyl (e.g., $C_{1-6}$alkoxybenzyl);
15.13. Formula 15.12 wherein $R_2$ is p-methoxybenzyl;
15.14. Formula XV or 1.1 wherein $R_2$ is $C_{3-8}$cycloalkyl (e.g., cyclopentyl, cyclohexyl) optionally substituted with one or more amino (e.g., —$NH_2$), for example, 2-aminocyclopentyl or 2-aminocyclohexyl);
15.15. Formula 15.14 wherein $R_2$ is cyclopentyl or cyclohexyl;
15.16. Formula 15.14 wherein $R_2$ is 2-aminocyclopentyl;
15.17. Formula 15.14 wherein $R_2$ is 2-aminocyclohextyl;
15.18. Formula XV or any of 1.1-15.4, wherein $R_2$ is $C_{1-6}$haloalkyl;
15.19. Formula 15.18, wherein $R_2$ is 2,2,2-trifluoroethyl;
15.20. Formula XV or any of 1.1-15.4, wherein $R_2$ is $C_{3-8}$heterocycloalkyl (e.g., pyrrolidinyl, for example, pyrrolidin-3-yl) optionally substituted with $C_{1-6}$alkyl (e.g., methyl), for example, 1-methylpyrrolidin-3-yl;
15.21. Formula 15.20, wherein $R_2$ is pyrrolidinyl (e.g., pyrrolidin-3-yl);

15.22. Formula 15.20, wherein $R_2$ is 1-methylpyrrolidin-3-yl;
15.23. Formula XV or any of 1.1-15.4, wherein $R_2$ is $C_{3-8}$cycloalkyl-$C_{1-6}$alkyl (e.g., cyclopropylmethyl);
15.24. Formula 15.23, wherein $R_2$ is cyclopropylmethyl;
15.25. Formula XV or any of 1.1-15.4, wherein $R_2$ is $C_{0-6}$alkylamino$C_{0-6}$alkyl (e.g., 2-(dimethylamino)ethyl, 2-aminopropyl);
15.26. Formula 15.25, wherein $R_2$ is 2-(dimethylamino)ethyl;
15.27. Formula 15.25, wherein $R_2$ is 2-aminopropyl;
Formula XV or any of 1.1-15.4, wherein $R_2$ is aryl$C_{0-6}$alkyl (e.g., benzyl);
15.28. Formula 15.27, wherein $R_2$ is benzyl;
15.29. Formula XV or any of 1.1-15.4, wherein $R_2$ is heteroarylalkyl (e.g., pyridylmethyl);
15.30. Formula 15.29, wherein $R_2$ is pyridylmethyl;
15.31. Formula XV or any of 1.1-15.4, wherein $R_2$ is -G-J wherein: G is a single bond or, $C_{1-6}$alkylene (e.g., methylene) and J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
15.32. Formula 15.31, wherein G is $C_{1-6}$alkylene;
15.33. Formula 15.31, wherein G is methylene;
15.34. Formula 15.31, wherein G is a single bond;
15.35. Any of formulae 15.31-15.34, wherein J is cycloalkyl or heterocycloalkyl (e.g., oxetan-2-yl, pyrolyin-3-yl, pyrolyin-2-yl) optionally substituted with alkyl (e.g., 1-methylpyrrolidin-2-yl);
15.36. Any of formulae 15.31-15.34, wherein J is oxetan-2-yl, pyrolyin-3-yl, pyrolyin-2-yl;
15.37. Any of formulae 15.31-15.34, wherein J is 1-methylpyrrolidin-2-yl;
15.38. Any of the preceding formulae wherein $R_3$ is D-E-F;
15.39. Formula 15.38, wherein D is single bond, $C_{1-6}$alkylene (e.g., methylene), or aryl$C_{1-6}$ alkylene (e.g., benzylene or —$CH_2C_6H_4$—);
15.40. Formula 15.38, wherein D is $C_{1-6}$alkylene (e.g., methylene);
15.41. Formula 15.38, wherein D is methylene;
15.42. Formula 15.38, wherein D is aryl$C_{1-6}$alkylene;
15.43. Formula 15.38, wherein D is benzylene;
15.44. Any of formulae 15.38-15.43, wherein E is $C_{1-6}$alkylene (e.g., methylene, ethynylene, prop-2-yn-1-ylene), arylene (e.g., phenylene or —$C_6H_4$—), $C_{1-6}$alkylarylene (e.g., -benzylene- or —$CH_2C_6H_4$—), amino$C_{1-6}$alkylene (e.g., —$CH_2N(H)$—) or amino (e.g., —N(H)—);
15.45. Formula 15.44, wherein E is $C_{1-6}$alkylene (e.g., methylene or ethynylene);
15.46. Formula 15.44, wherein E is methylene;
15.47. Formula 15.44, wherein E is ethynylene;
15.48. Formula 15.44, wherein E is amino$C_{1-6}$alkylene (e.g., —$CH_2N(H)$—);
15.49. Formula 15.44, wherein E is arylene (e.g., phenylene or —$C_6H_4$—);
15.50. Formula 15.44, wherein E is phenylene or —$C_6H_4$—;
15.51. Any of formulae 15.38-15.50, wherein F is $C_{1-6}$alkyl (e.g., isobutyl, isopropyl); aryl (e.g., phenyl); heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidazol-2-yl, 1,2,4-triazol-1-yl; hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl; amino (e.g., —$NH_2$); $C_{1-6}$alkoxy; or —O-halo$C_{1-6}$alkyl (e.g., —O—$CF_3$);
15.52. Formula 15.51, wherein F is aryl (e.g., phenyl);
15.53. Formula 15.51, wherein F is phenyl;
15.54. Formula 15.51, wherein F is alkoxy (e.g., methoxy);
15.55. Formula 15.51 or 15.54, wherein F is methoxy;
15.56. Formula 15.51, wherein F is —O—$C_{1-6}$haloalkyl (e.g., —$OCF_3$);
15.57. Formula 15.51 or 15.56, wherein F is —$OCF_3$;
15.58. Formula 15.51, wherein F is —$NH_2$;
15.59. Formula 15.51, wherein F is hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl;
15.60. Formula 15.51 or 15.59 wherein F is pyrrolidin-1-yl;
15.61. Formula 15.51 or 15.59 wherein F is pyrrolidin-2-yl;
15.62. Formula 15.51 or 15.59 wherein F is 1-methylpyrrolidin-2-yl;
15.63. Formula 15.51 or 15.59 wherein F is piperidin-2-yl;
15.64. Formula 15.51 or 15.59 wherein F is 1-methylpiperidin-2-yl or 1-ethylpiperidin-2-yl;
15.65. Formula 15.51, wherein F is $C_{1-6}$alkyl (e.g., isobutyl, isopropyl);
15.66. Formula 15.51 or 15.65, wherein F is isobutyl;
15.67. Formula 15.51 or 15.65, wherein F is isopropyl;
15.68. Formula 15.51, wherein F is heteroaryl (e.g., 1,2,4-triazolyl, imidazolyl, pyridyl) optionally substituted with $C_{1-6}$alkyl, for example, pyrid-2-yl, imidazol-1-yl, 4-methylimidazol-1-yl, 1-methylimidazol-2-yl, 1,2,4-triazol-1-yl;
15.69. Formula 15.51 or 15.68, wherein F is pyridyl (e.g., pyrid-2-yl);
15.70. Formula 15.51 or 15.68, wherein F is imidazolyl optionally substituted with $C_{1-6}$alkyl;
15.71. Formula 15.51 or 15.68, wherein F is imidazol-1-yl;
15.72. Formula 15.51 or 15.68, wherein F is 4-methylimidazol-1-yl;
15.73. Formula 15.51 or 15.68, wherein F is 1-methylimidazol-2-yl;
15.74. Formula 15.51 or 15.68, wherein F is 1,2,4-triazol-1-yl;
15.75. Any of formulae 15.1-15.37, wherein $R_3$ is a substituted heteroarylalkyl, e.g., substituted with $C_{1-6}$haloalky;
15.76. Any of formulae 15.1-15.37, wherein $R_3$ is attached to one of the nitrogen atoms on the pyrazolo portion of Formula I and is a moiety of Formula A as hereinbefore described in Formula Q;
15.77. Formula 15.76, wherein $R_8$, $R_9$, $R_{11}$ and $R_{12}$ of Formula A are each H and $R_{10}$ is phenyl;
15.78. Formula 15.76, wherein $R_8$, $R_9$, $R_{11}$ and $R_{12}$ are each H and $R_{10}$ is pyridyl or thiadizolyl;
15.79. Formula 15.76, wherein $R_8$, $R_9$, $R_{11}$ and $R_{12}$ are each H and $R_{10}$ is 2-pyridyl;
15.80. Formula 15.76, wherein $R_8$, $R_9$, $R_{11}$ and $R_{12}$ are each H and $R_{10}$ is 4,6-dimethylpyrid-2-yl or 2-pyrrolinyl;

15.81. Formula 15.76, wherein X, Y and Z are all C,
15.82. Any of the preceding formulae, wherein R$_4$ aryl (e.g., phenyl) optionally substituted with one or more halo (e.g., F or Cl) or hydroxyl, heteroaryl (e.g., pyrid-4-yl, pyrid-2-yl or pyrazol-3-yl) or heteroC$_{3-6}$cycloalkyl (e.g., pyrrolidin-3-yl);
15.83. Formula 15.82, wherein R$_4$ is aryl (e.g., phenyl), heteroaryl (e.g., pyrid-4-yl, pyrid-2-yl or pyrazol-3-yl) or heterocycloalkyl (e.g., pyrrolidin-3-yl);
15.84. Formula 15.82 or 15.83, wherein R$_4$ is aryl (e.g., phenyl) optionally substituted with one or more halo or hydroxyl;
15.85. Formula 15.82 or 15.83, wherein R$_4$ is phenyl optionally substituted with one or more halo or hydroxyl;
15.86. Formula 15.82 or 15.83, wherein R$_4$ is phenyl, 4-fluorophenyl, 4-hydroxyphenyl, 2-hydroxyphenyl, 2,4-dichlorophenyl;
15.87. Formula 15.82 or 15.83, wherein R$_4$ is heteroaryl;
15.88. Formula 15.82 or 15.83, wherein R$_4$ is pyrid-4-yl, pyrid-2-yl or pyrazol-3-yl;
15.89. Formula 15.82 or 15.83, wherein R$_4$ is heterocycloalkyl (e.g., pyrrolidin-3-yl)
15.90. Any of the preceding formulae wherein R$_5$ is H, C$_{1-6}$alkyl, C$_{3-8}$cycloalkyl (e.g., cyclopentyl), heteroaryl, aryl, p-benzylaryl (e.g., biphenyl-4-ylmethyl);
15.91. Formula 15.90, wherein R$_5$ is H,
15.92. Formula 15.90, wherein R$_5$ is C$_{1-6}$alkyl;
15.93. A compound selected from any of the following:

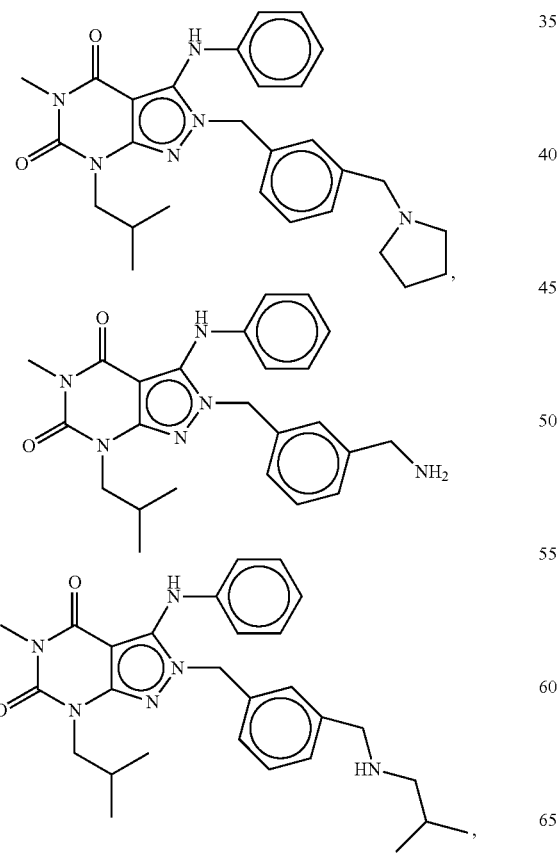

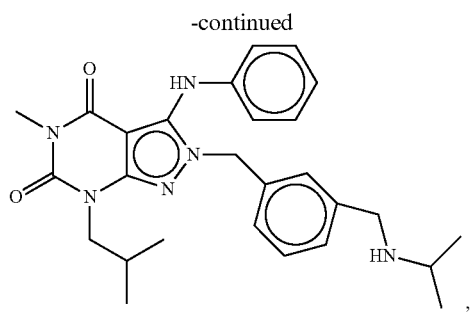

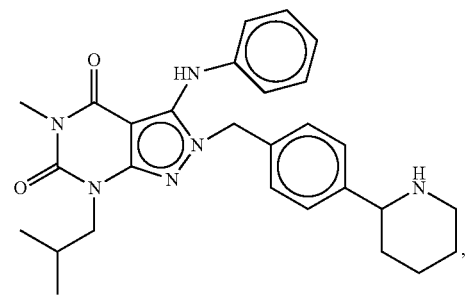

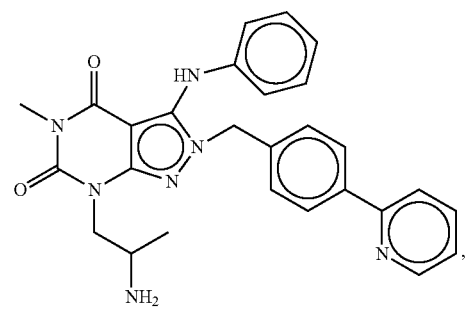

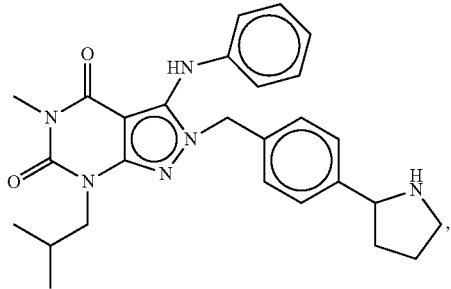

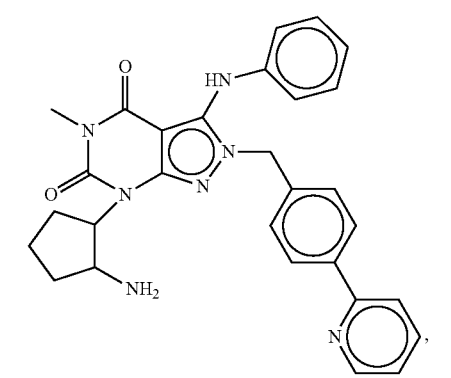

-continued
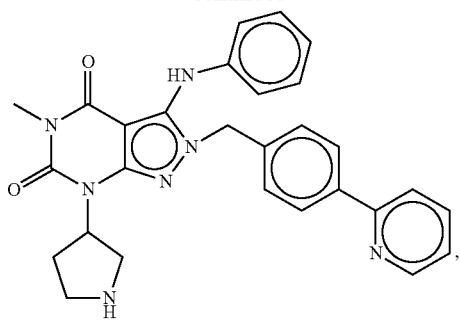
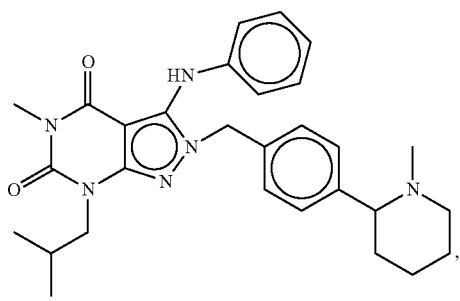
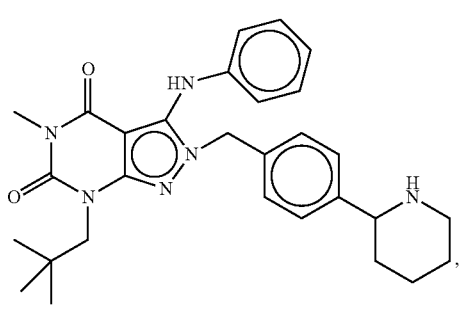
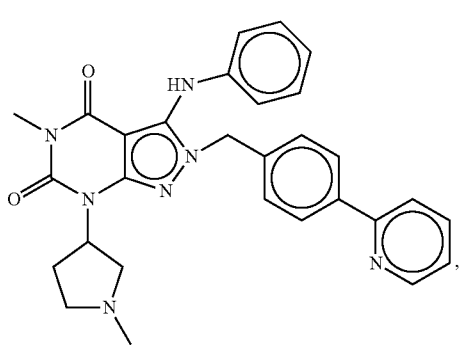
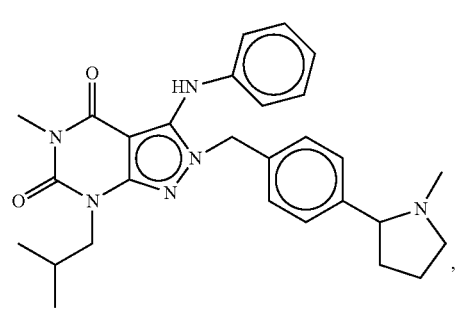
-continued
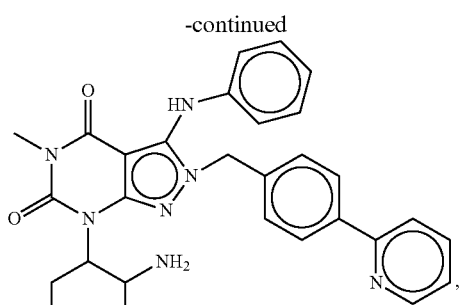
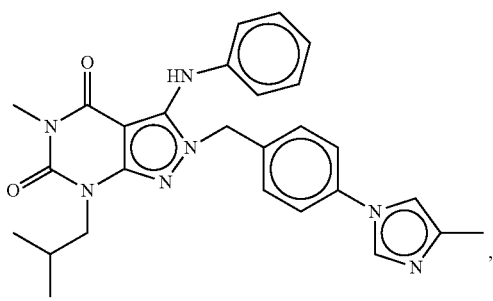
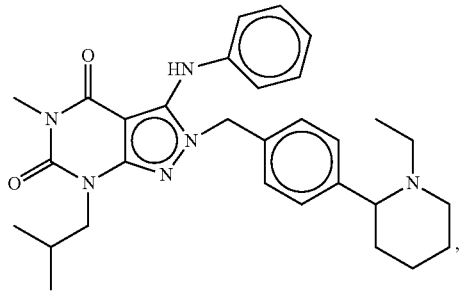
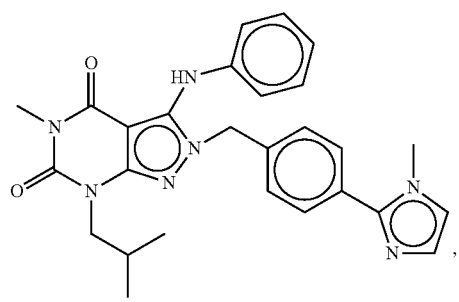
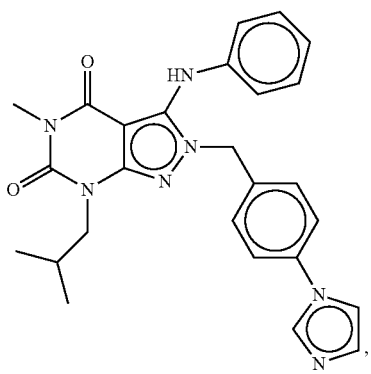

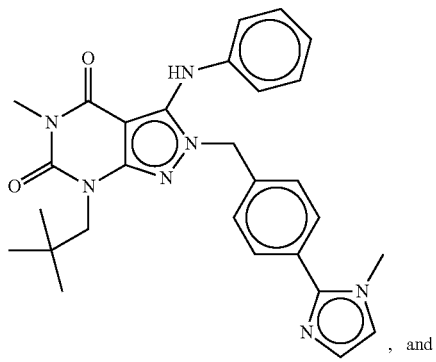
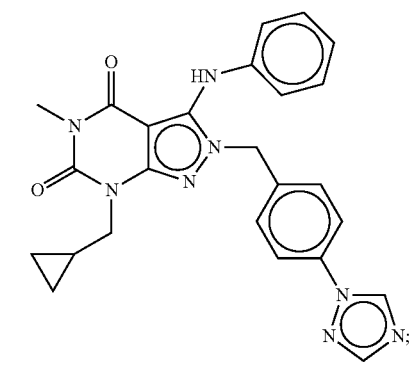
15.94. A compound selected from any of the following:
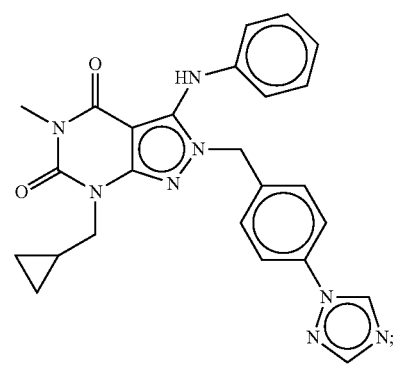
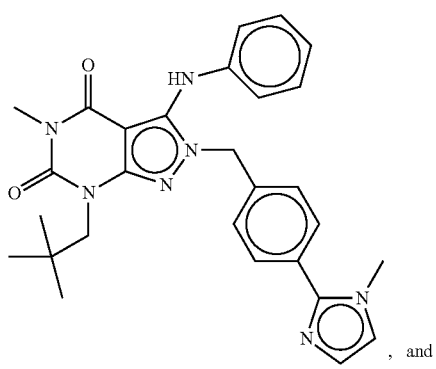
, and
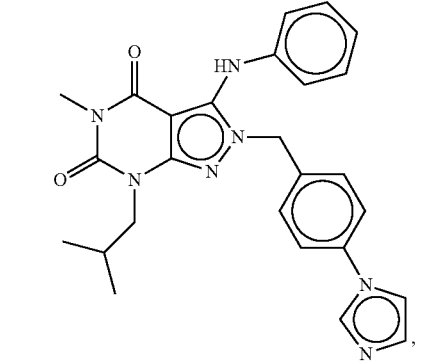
,
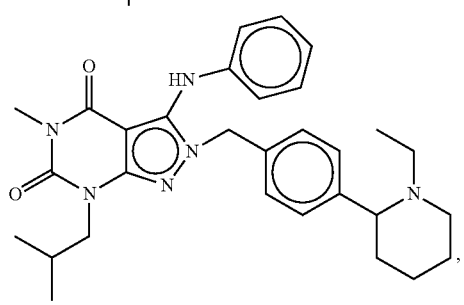
,
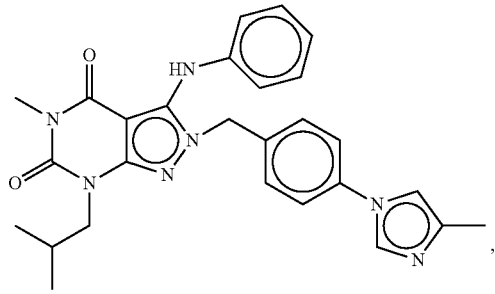
,
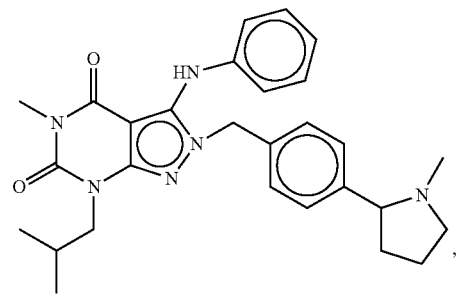
,

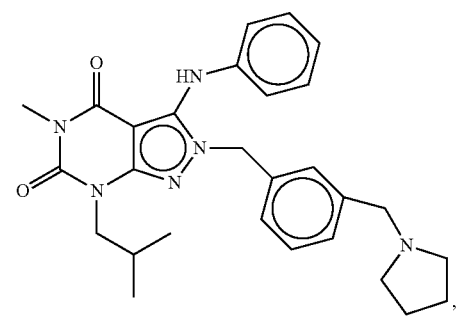
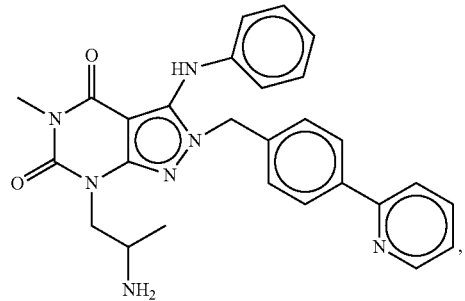
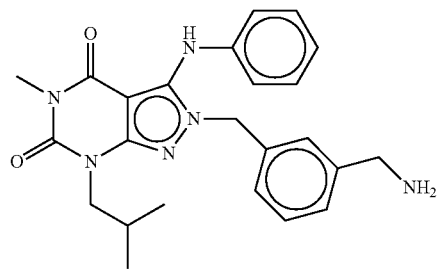
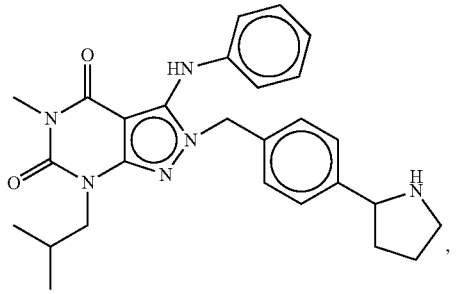
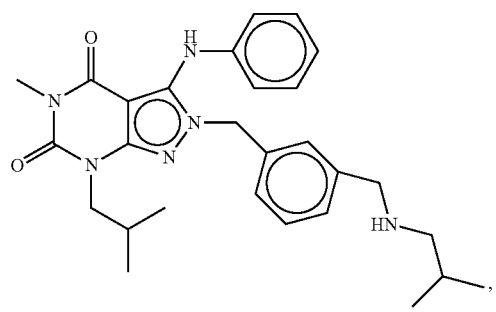
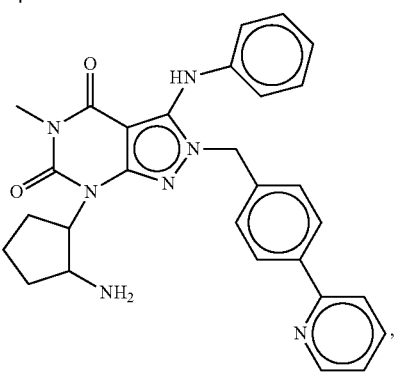
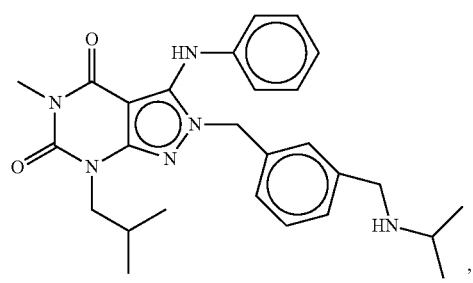
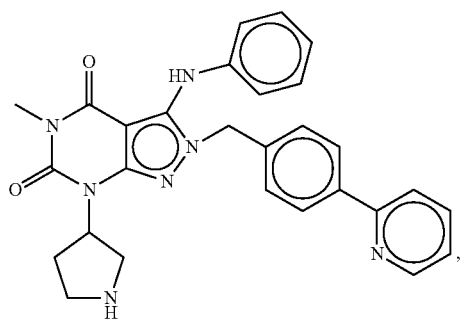
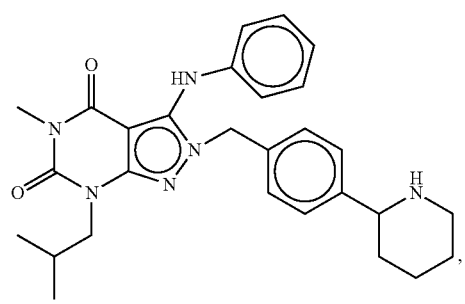
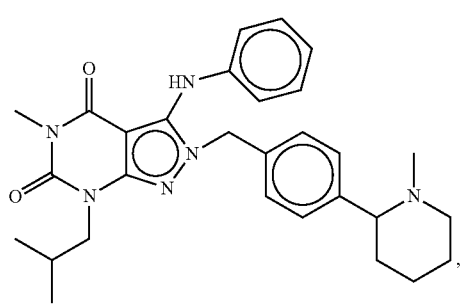

-continued

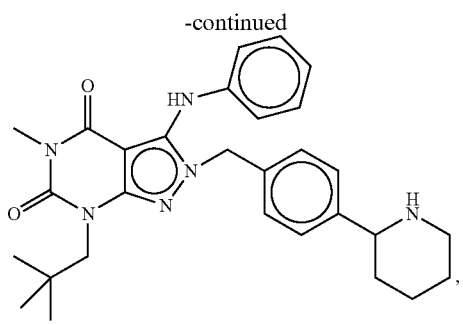

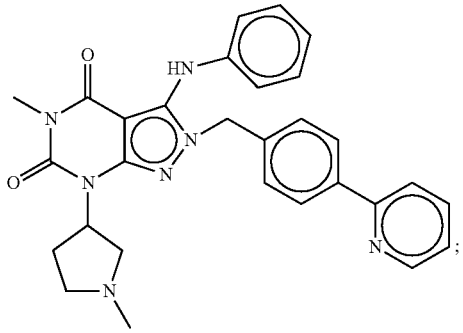

15.95. Any one of the preceding formulae wherein the compounds inhibit phosphodiesterase-mediated (e.g., PDE 1-mediated, especially PDE1B-mediated) hydrolysis of cGMP, e.g., with an $IC_{50}$ of less than 1 μM, preferably less than preferably less than 250 nM, preferably less than 50 nM, more preferably less than 25 nM in an immobilized-metal affinity particle reagent PDE assay, for example, as described in Example 1 below;

such compounds according to any of the preceding formulae being in free, salt or prodrug form.

In yet another embodiment, the PDE 1 Inhibitors for use in the methods of treatment described herein are compounds of Formula XVI:

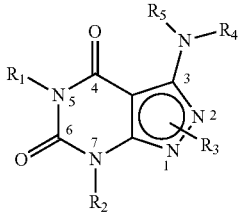

Formula XVI wherein
(i) $R_1$ is H or $C_{1-6}$alkyl (e.g., methyl);
(ii) $R_2$ is H, alkyl (e.g., isopropyl, isobutyl, 2-methylbutyl, 2,2-dimethyl propyl), cycloalkyl (e.g., cyclopentyl, cyclohexyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), heteroarylalkyl (e.g., pyridylmethyl), or alkoxyarylalkyl (e.g., 4-methoxybenzyl);
(iii) $R_3$ is D-E-F wherein
 1. D is single bond, $C_{1-6}$alkylene (e.g., methylene), or aryl$C_{1-6}$alkylene (e.g., benzylene or —$CH_2C_6H_4$—);
 2. E is a $C_{1-6}$alkylene (e.g., methylene, ethynylene, prop-2-yn-1-ylene), arylene (e.g., phenylene or —$C_6H_4$—), $C_{1-6}$alkylarylene (e.g., -benzylene- or —$CH_2C_6H_4$—), amino$C_{1-6}$alkylene (e.g., —$CH_2N(H)$—) or amino (e.g., —N(H)—); and
 3. F is
  $C_{1-6}$alkyl (e.g., isobutyl, isopropyl),
  aryl (e.g., phenyl),
  heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidazol-2-yl, 1,2,4-triazol-1-yl,
  hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
  amino (e.g., —$NH_2$),
  $C_{1-6}$alkoxy, or
  —O-halo$C_{1-6}$alkyl (e.g., —O—$CF_3$),
  provided that when -D-E- is an heteroarylalkyl or arylalkyl (e.g., benzyl), F is not aryl or heteroaryl;
(iv) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); and
(v) $R_5$ is H, alkyl, cycloalkyl (e.g., cyclopentyl), heteroaryl, aryl, p-benzylaryl (e.g., biphenyl-4-ylmethyl);
wherein "alk", "alkyl", "haloalkyl" or "alkoxy" refers to $C_{1-6}$ alkyl and "cycloalkyl" refers to $C_{3-8}$ cycloalkyl;
in free, salt or prodrug form.

In yet another embodiment, the PDE 1 Inhibitors for use in the methods of treatment described herein are compounds of Formula XVII

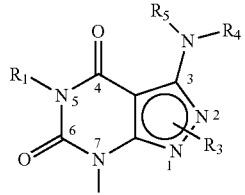

Formula XVII wherein
(i) $R_1$ is H or alkyl (e.g., methyl);
(ii) $R_2$ is H, alkyl (e.g., isopropyl, isobutyl, 2-methylbutyl, 2,2-dimethyl propyl), cycloalkyl (e.g., cyclopentyl, cyclohexyl), haloalkyl (e.g., trifluoromethyl, 2,2,2-trifluoroethyl), alkylaminoalkyl (e.g., 2-(dimethylamino)ethyl), hydroxyalkyl (e.g., 3-hydroxy-2-methyl propyl), arylalkyl (e.g., benzyl), heteroarylalkyl (e.g., pyridylmethyl), or alkoxyarylalkyl (e.g., 4-methoxybenzyl);
(iii) $R_3$ is D-E-F wherein
 1. D is single bond, alkylene (e.g., methylene), or arylalkylene (e.g., benzylene or —$CH_2C_6H_4$);
 2. E is a alkylene (e.g., methylene, ethynylene, prop-2-yn-1-ylene), arylene (e.g., phenylene or —$C_6H_4$—), alkylarylene (e.g., -benzylene- or —$CH_2C_6H_4$—), aminoalkylene (e.g., —$CH_2N(H)$—) or amino (e.g., —N(H)—); and
 3. F is alkyl (e.g., isobutyl), aryl (e.g., phenyl), heteroaryl (e.g., pyrid-2-yl, 1,2,4-triazolyl), hetero$C_{3-6}$ cycloalkyl (e.g., pyrrolidin-1-yl), amino (e.g., —$NH_2$), $C_{1-4}$alkoxy, or —O-haloalkyl (e.g., —O—$CF_3$);

provided that when -D-E- is an heteroarylalkyl or arylalkyl (e.g., benzyl), F is not aryl or heteroaryl.

(iv) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); and (v) $R_5$ is H, alkyl, cycloalkyl (e.g., cyclopentyl), heteroaryl, aryl, p-benzylaryl (e.g., biphenyl-4-ylmethyl);

wherein "alk", "alkyl", "haloalkyl" or "alkoxy" refers to $C_{1-6}$ alkyl and "cycloalkyl" refers to $C_{3-6}$ cycloalkyl;

in free, salt or prodrug form.

In yet another embodiment, the PDE 1 Inhibitors of Formula XVII for use in the methods of treatment described herein are as follows:

17.1. Formula XVII wherein $R_1$ is methyl;
17.2. Formula XVII or 2.1 wherein $R_2$ is $C_{1-6}$ alkyl;
17.3. Formula 2.2 wherein $R_2$ is isopropyl, isobutyl, 2,2-dimethylpropyl, or 2-methylbutyl;
17.4. Formula XVII or 2.1 wherein $R_2$ is hydroxy $C_{1-6}$ alkyl;
17.5. Formula XVII or 2.1 wherein $R_1$ is 3-hydroxy-2-methyl propyl;
17.6. Formula XVII or 2.1 wherein $R_1$ is $C_{1-6}$ alkoxybenzyl;
17.7. Formula 2.6 wherein $R_1$ is p-methoxybenzyl;
17.8. Formula XVII or 2.1 wherein $R_2$ is $C_{3-6}$ cycloalkyl;
17.9. Formula 2.8 wherein $R_2$ is cyclopentyl or cyclohexyl;
17.10. Formula XVII or 2.1 wherein $R_2$ is $C_{1-6}$ haloalkyl;
17.11. Formula 2.10 wherein $R_2$ is 2,2,2-trifluoroethyl;
17.12. Any of the preceding formulae wherein $R_3$ is D-E-F and D is single bond, alkylene (e.g., methylene), or arylalkylene (e.g., -benzylene- or —$CH_2C_6H_4$—);
17.13. Any of the preceding formulae wherein $R_3$ is D-E-F and D is alkylene (e.g., methylene);
17.14. Any of the preceding formulae XVII-17.11 wherein $R_3$ is D-E-F and D is methylene
17.15. Any of the preceding formulae XVII-17.11 wherein $R_3$ is D-E-F and D is benzylene;
17.16. Any of the preceding formulae XVII-17.15, wherein $R_3$ is D-E-F and E is alkylene (e.g., methylene or ethynylene), arylene (e.g., phenylene), alkylarylene (e.g., -benzylene-), aminoalkylene (e.g., —$CH_2N(H)$—) or amino (e.g., —N(H)—);
17.17. Any of the preceding formulae XVII-17.16, wherein $R_3$ is D-E-F and E is alkylene (e.g., methylene or ethynylene);
17.18. Any of the preceding formulae XVII-17.17, wherein $R_3$ is D-E-F and E is methylene;
17.19. Any of the preceding formulae XVII-17.17, wherein $R_3$ is D-E-F and E is ethynylene;
17.20. Any of the preceding formulae XVII-17.17, wherein $R_3$ is D-E-F and E is aminoalkylene (e.g., —$CH_2N(H)$—);
17.21. Any of the preceding formulae XVII-17.20, wherein $R_3$ is D-E-F and F is alkyl (e.g., isobutyl), aryl (e.g., phenyl), heteroaryl (e.g., pyrid-2-yl, 1,2,4-triazolyl), hetero$C_{3-6}$cycloalkyl (e.g., pyrrolidin-1-yl), amine (e.g., —$NH_2$), alkoxy (e.g., methoxy) or —O-haloalkyl (—$OCF_3$);
17.22. Any of the preceding formulae XVII-17.21, wherein $R_3$ is D-E-F and F is aryl (e.g., phenyl);
17.23. Any of the preceding formulae XVII-17.22, wherein $R_3$ is D-E-F and F is phenyl;
17.24. Any of the preceding formulae XVII-17.21, wherein $R_3$ is D-E-F and F is alkoxy (e.g., methoxy) or —O-haloalkyl (e.g., —$OCF_3$);

17.25. Any of the preceding formulae XVII-17.21 or 17.24, wherein $R_3$ is D-E-F and F is methoxy;
17.26. Any of the preceding formulae XVII-17.21 or 17.24, wherein $R_3$ is D-E-F and F is —$OCF_3$;
17.27. Any of the preceding formulae XVII-17.21, wherein $R_3$ is D-E-F and F is —$NH_2$;
17.28. Any of the preceding formulae I-17.21, wherein $R_3$ is D-E-F and F is hetero$C_{3-6}$cycloalkyl (e.g., pyrrolidin-1-yl);
17.29. Any of the preceding formulae XVII-17.21 or 17.28, wherein $R_3$ is D-E-F and F is pyrrolidin-1-yl;
17.30. Any of the preceding formulae XVII-17.21, wherein $R_3$ is D-E-F and F is alkyl (e.g., isobutyl);
17.31. Any of the preceding formulae XVII-17.21 or 17.30, wherein $R_3$ is D-E-F and F is isobutyl;
17.32. Any of the preceding formulae XVII or any of 17.1-17.31, wherein $R_4$ is aryl (e.g., phenyl), heteroaryl (e.g., pyrid-4-yl, pyrid-2-yl or pyrazol-3-yl) or heterocycloalkyl (e.g., pyrrolidin-3-yl);
17.33. Any of the preceding formulae or any of 17.1-17.32, wherein $R_4$ is phenyl;
17.34. Any of the preceding formulae wherein $R_4$ is heteroaryl;
17.35. Any of the preceding formulae wherein $R_4$ is pyrid-4-yl, pyrid-2-yl or pyrazol-3-yl;
17.36. Any of the preceding formulae wherein $R_4$ is heterocycloalkyl (e.g., pyrrolidin-3-yl)
17.37. Any of the preceding formulae wherein $R_5$ is H;
17.38. A compound selected from the compounds of Examples 7, 8, 9, 15, 16 and 17 below; and/or
17.39. Any one of the preceding formulae wherein the compounds inhibit phosphodiesterase-mediated (e.g., PDE1-mediated, especially PDE 1B-mediated) hydrolysis of cGMP, e.g., with an $IC_{50}$ of less than 1 μM, preferably less than 25 nM in an immobilized-metal affinity particle reagent PDE assay, for example, as described in Example 1 below;

such compounds according to any of the preceding formulae being in free, salt or prodrug form.

In yet another embodiment, the PDE 1 Inhibitors for use in the methods of treatment described herein are Compounds of Formula XVIII:

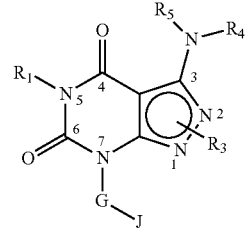

Formula XVIII wherein
(i) $R_1$ is H or alkyl (e.g., methyl);
(ii) G is a single bond or, alkylene (e.g., methylene);
(iii) J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl)); or
-G-J is
$C_{3-8}$cycloalkyl (e.g., cyclopentyl, cyclohexyl) substituted with one or more amino (e.g., —$NH_2$), for example, 2-aminocyclopentyl or 2-aminocyclohexyl), C$_{3-8}$heterocycloalkyl (e.g., pyrrolidinyl, for example, pyrrolidin-3-yl) optionally substituted with C$_{1-6}$alkyl (e.g., methyl), for example, 1-methylpyrrolidin-3-yl, C$_{3-8}$cycloalkyl-C$_{1-6}$alkyl (e.g., cyclopropylmethyl), aminoC$_{1-6}$alkyl (e.g., 2-aminopropyl), provided that when G is a single bond, J is not an unsubstituted cycloalkyl;

(iv) R$_3$ is
a) D-E-F wherein
1. D is single bond, C$_{1-6}$alkylene (e.g., methylene), or arylC$_{1-6}$alkylene (e.g., benzylene or —CH$_2$C$_6$H$_4$—);
2. E is a C$_{1-6}$alkylene (e.g., methylene, ethynylene, prop-2-yn-1-ylene), arylene (e.g., phenylene or —C$_6$H$_4$—), C$_{1-6}$alkylarylene (e.g., -benzylene- or —CH$_2$C$_6$H$_4$—), aminoC$_{1-6}$alkylene (e.g., —CH$_2$N(H)—) or amino (e.g., —N(H)—); and
3. F is
C$_{1-6}$alkyl (e.g., isobutyl, isopropyl),
aryl (e.g., phenyl),
heteroaryl (e.g., 1,2,4-triazolyl, imidazolyl, pyridyl) optionally substituted with C$_{1-6}$alkyl, for example, pyrid-2-yl, imidazol-1-yl, 4-methylimidazolyl, 1-methylimidazol-2-yl, 1,2,4-triazol-1-yl,
heteroC$_{3-8}$cycloalkyl (e.g., piperidinyl, pyrrolidinyl) optionally substituted with C$_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
amino (e.g., —NH$_2$),
C$_{1-6}$alkoxy, or
—O-haloC$_{1-6}$alkyl (e.g., —O—CF$_3$),
b) R$_3$ is a substituted heteroarylaklyl, e.g., substituted with haloalkyl; or
c) R$_3$ is attached to one of the nitrogen atoms on the pyrazolo portion of Formula XVIII and is a moiety of Formula A

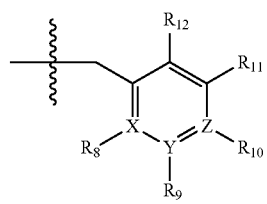

Formula A wherein X, Y and Z are, independently, N or C, and R$_8$, R$_9$, R$_{11}$ and R$_{12}$ are independently H or halogen (e.g., Cl or F); and R$_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl (e.g., methoxycarbonyl), aminocarbonyl; preferably phenyl or pyridyl, e.g., 2-pyridyl; provided that when X, Y or X is nitrogen, R$_8$, R$_9$ or R$_{10}$, respectively, is not present;

(v) R$_4$ is aryl (e.g., phenyl) optionally substituted with one or more halo (e.g., F or Cl) or hydroxyl, heteroaryl (e.g., pyrid-4-yl, pyrid-2-yl or pyrazol-3-yl) or heteroC$_{3-6}$cycloalkyl (e.g., pyrrolidin-3-yl); and (vi) R$_5$ is H, C$_{3-8}$cycloalkyl (e.g., cyclopentyl), heteroaryl, aryl, p-benzylaryl (e.g., biphenyl-4-ylmethyl), wherein "alk", "alkyl", "haloalkyl" or "alkoxy" refers to C$_{1-6}$ alkyl and "cycloalkyl" refers to C$_{3-6}$ cycloalkyl;

in free, salt or prodrug form.

In yet another embodiment, the PDE 1 Inhibitors for use in the methods of treatment described herein are compounds of Formula XIX:

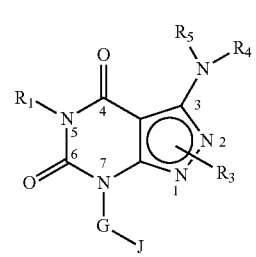

Formula XIX wherein
(i) R$_1$ is H or alkyl (e.g., methyl);
(ii) G is a single bond or, alkylene (e.g., methylene);
(iii) J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
provided that when G is a single bond, J is not cycloalkyl;

(iv) R$_3$ is
a) D-E-F wherein
1. D is single bond, alkylene (e.g., methylene), arylalkylene (e.g., benzylene or —CH$_2$C$_6$H$_4$—);
2. E is a alkylene (e.g., methylene, ethynylene, prop-2-yn-1-ylene), arylene (e.g., phenylene or —C$_6$H$_4$—), alkylarylene (e.g., -benzylene- or —CH$_2$C$_6$H$_4$—), aminoalkylene (e.g., —CH$_2$N(H)—) or amino (e.g., —N(H)—); and
3. F is alkyl (e.g., isobutyl), aryl (e.g., phenyl), heteroaryl (e.g., pyrid-2-yl, 1,2,4-triazolyl), heteroC$_{3-6}$cycloalkyl (e.g., pyrrolidin-1-yl), amino (e.g., —NH$_2$), C$_{1-6}$alkoxy, or —O-haloalkyl (e.g., —O—CF$_3$);
b) R$_3$ is a substituted heteroarylaklyl, e.g., substituted with haloalkyl; or
c) R$_3$ is attached to one of the nitrogen atoms on the pyrazolo portion of Formula XIX and is a moiety of Formula A

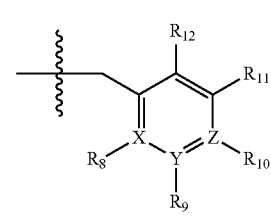

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;

(v) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); and (vi) $R_5$ is H, alkyl, cycloalkyl (e.g., cyclopentyl), heteroaryl, aryl, p-benzylaryl (e.g., biphenyl-4-ylmethyl);

wherein "alk", "alkyl", "haloalkyl" or "alkoxy" refers to $C_{1-6}$ alkyl and "cycloalkyl" refers to $C_{3-6}$ cycloalkyl;

in free, salt or prodrug form.

In yet another embodiment, the PDE 1 Inhibitors of Formula XIX for use in the methods of treatment described herein are as follows:

19.1. Formula XIX wherein $R_1$ is methyl;

19.2. Formula XIX or 19.1, wherein G is a single bond or alkylene (e.g., methylene) and J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl);

19.3. Formula XIX or 19.1 or 3.2 wherein G is alkylene (e.g., methylene);

19.4. Formula XIX or any of 19.1-19.3 wherein G is methylene;

19.5. Formula XIX or any of 19.1-19.4 wherein J is cycloalkyl or heterocycloalkyl (e.g., oxetan-2-yl, pyrolyin-3-yl, pyrolyin-2-yl) optionally substituted with alkyl (e.g., 1-methylpyrrolidin-2-yl);

19.6. Formula XIX or any of 19.1-19.5 wherein J is oxetan-2-yl, pyrolyin-3-yl, pyrolyin-2-yl;

19.7. Formula XIX or any of 19.1-19.5 wherein J is (1-methylpyrrolidin-2-yl);

19.8. Any of the preceding formulae wherein $R_3$ is D-E-F and D is single bond, alkylene (e.g., methylene), or arylalkylene (e.g., -benzylene-);

19.9. Any of the preceding formulae wherein D is alkylene (e.g., methylene);

19.10. Any of the preceding formulae XIX-19.9 wherein $R_3$ is D-E-F and D is methylene 19.11. Any of the preceding formulae XIX-19.8 wherein $R_3$ is D-E-F and D is benzylene;

19.12. Any of the preceding formulae XIX-19.11 wherein $R_3$ is D-E-F and E is a alkylene (e.g., methylene, ethynylene, prop-2-yn-1-ylene), arylene (e.g., phenylene or —$C_6H_4$—), alkylarylene (e.g., -benzylene- or —$CH_2C_6H_4$—), aminoalkylene (e.g., —$CH_2N(H)$—) or amino (e.g., —N(H)—);

19.13. Any of the preceding formulae XIX-19.12, wherein $R_3$ is D-E-F and E is alkylene (e.g., methylene or ethynylene);

19.14. Any of the preceding formulae XIX-19.13, wherein $R_3$ is D-E-F and E is methylene;

19.15. Any of the preceding formulae XIX-19.13, wherein $R_3$ is D-E-F and E is ethynylene;

19.16. Any of the preceding formulae XIX-19.12, wherein $R_3$ is D-E-F and E is aminoalkylene (e.g., —$CH_2N(H)$—);

19.17. Any of the preceding formulae XIX-19.16, wherein $R_3$ is D-E-F and F is alkyl (e.g., isobutyl), aryl (e.g., phenyl), heteroaryl (e.g., pyrid-2-yl, 1,2,4-triazolyl), heteroC$_{3-6}$cycloalkyl (e.g., pyrrolidin-1-yl), amino (e.g., —$NH_2$), $C_{1-4}$alkoxy, or —O-haloalkyl (e.g., —O—$CF_3$);

19.18. Any of the preceding formulae XIX-19.17, wherein $R_3$ is D-E-F and F is aryl (e.g., phenyl);

19.19. Any of the preceding formulae XIX-19.18, wherein $R_3$ is D-E-F and F is phenyl;

19.20. Any of the preceding formulae XIX-19.17, wherein $R_3$ is D-E-F and F is —O-alkyl (e.g., methoxy) or —O-haloalkyl (e.g., —$OCF_3$);

19.21. Any of the preceding formulae XIX-19.17 or 19.20 wherein $R_3$ is D-E-F and F is methoxy;

19.22. Any of the preceding formulae XIX-19.17 or 19.20, wherein $R_3$ is D-E-F and F is —$OCF_3$;

19.23. Any of the preceding formulae XIX-19.17, wherein $R_3$ is D-E-F and F is —$NH_2$;

19.24. Any of the preceding formulae XIX-19.17, wherein $R_3$ is D-E-F and F is heteroC$_{3-6}$cycloalkyl (e.g., pyrrolidin-1-yl);

19.25. Any of the preceding formulae XIX-19.17 or 19.24, wherein $R_3$ is D-E-F and F is pyrrolidin-1-yl;

19.26. Any of the preceding formulae XIX-19.17, wherein $R_3$ is D-E-F and F is alkyl;

19.27. Any of the preceding formulae XIX-19.17 or 19.26, wherein F is isobutyl;

19.28. Any of the preceding formulae XIX-19.7 wherein $R_3$ is a moiety of Formula A wherein $R_8$, $R_9$, $R_{11}$ and $R_{12}$ are each H and $R_{10}$ is phenyl;

19.29. Any of the preceding formulae XIX-19.7 wherein $R_3$ is a moiety of Formula A wherein $R_8$, $R_9$, $R_{11}$ and $R_{12}$ are each H and $R_{10}$ is pyridyl or thiadizolyl;

19.30. Formula 19.29 wherein $R_3$ is a moiety of Formula A wherein $R_8$, $R_9$, $R_{11}$ and $R_{12}$ are each H and $R_{10}$ is 2-pyridyl optionally substituted with fluoro (e.g., 6-fluoropyrid-2-yl);

19.31. Any of the preceding formulae XIX-19.7 or 19.28-19.30, wherein X, Y and Z are all C 19.32. Any of the preceding formulae XIX-19.31, wherein $R_4$ is aryl (e.g., phenyl), heteroaryl (e.g., pyrid-4-yl, pyrid-2-yl or pyrazol-3-yl) or heterocycloalkyl (e.g., pyrrolidin-3-yl);

19.33. Any of the preceding formulae XIX-19.32, wherein $R_4$ is phenyl;

19.34. Any of the preceding formulae XIX-19.31, wherein $R_4$ is heteroaryl (e.g., pyrid-4-yl, pyrid-2-yl or pyrazol-3-yl);

19.35. Any of the preceding formulae XIX-19.31 or 19.34, wherein $R_4$ is pyrid-4-yl, pyrid-2-yl or pyrazol-3-yl;

19.36. Any of the preceding formulae XIX-19.31 or 19.34, wherein $R_4$ is pyrrolidin-3-yl;

19.37. Any of the preceding formulae wherein $R_5$ is H, 19.38. A compound selected from the compounds of Examples 6, 12, 13 and 14 below; and/or 19.39. Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 µM, preferably less than 25 nM in an immobilized-metal affinity particle reagent PDE assay, for example, as described in Example 19;

such compounds according to any of the preceding formulae being in free, salt or prodrug form.

In yet another embodiment, the PDE 1 Inhibitors for use in the methods of treatment described herein are compounds of Formula XX:

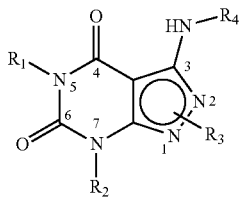

Formula XX wherein
(i) $R_1$ is H or alkyl (e.g., methyl);
(ii) $R_2$ is alkyl (e.g., isopropyl, isobutyl, isopropyl, 2,2-dimethylpropyl);
(iii) $R_3$ is
   a) D-E-F wherein
      1. D is single bond, $C_{1-6}$alkylene (e.g., methylene), or arylC$_{1-6}$alkylene (e.g., benzylene or —CH$_2$C$_6$H$_4$—);
      2. E is a $C_{1-6}$alkylene (e.g., methylene, ethynylene, prop-2-yn-1-ylene), arylene (e.g., phenylene or —C$_6$H$_4$—), $C_{1-6}$alkylarylene (e.g., -benzylene- or —CH$_2$C$_6$H$_4$—), amino$C_{1-6}$alkylene (e.g., —CH$_2$N(H)—) or amino (e.g., —N(H)—); and
      3. F is
         $C_{1-6}$alkyl (e.g., isobutyl, isopropyl),
         aryl (e.g., phenyl),
         heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidazol-2-yl,
         heteroC$_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
         amino (e.g., —NH$_2$),
         $C_{1-6}$alkoxy, or
         —O-haloC$_{1-6}$alkyl (e.g., —O—CF$_3$),
   b) $R_3$ is a substituted heteroarylaklyl, e.g., substituted with haloalkyl; or
   c) $R_3$ is attached to one of the nitrogen atoms on the pyrazolo portion of Formula XX and is a moiety of Formula A

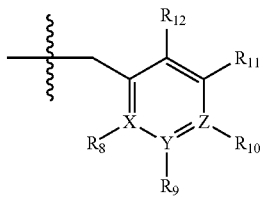

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;

(iv) $R_4$ is aryl (e.g., phenyl) optionally substituted with one or more halo (e.g., F or Cl) or hydroxyl, heteroaryl (e.g., pyrid-4-yl, pyrid-2-yl or pyrazol-3-yl) or heteroC$_{3-6}$cycloalkyl (e.g., pyrrolidin-3-yl);

wherein "alk", "alkyl", "haloalkyl" or "alkoxy" refers to $C_{1-6}$ alkyl and "cycloalkyl" refers to $C_{3-6}$ cycloalkyl;

in free, salt or prodrug form.

In a further embodiment, the Compound of Formula XX includes the proviso that when $R_4$ is unsubstituted aryl (e.g., phenyl), and $R_3$ is a moiety of Formula A, wherein $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl, In yet another embodiment, the PDE 1 Inhibitors for use in the methods of treatment described herein are compounds of Formula XXI:

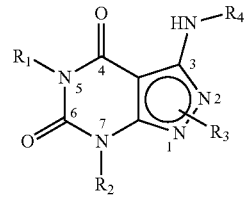

Formula XXI wherein
(i) $R_1$ is H or alkyl (e.g., methyl);
(ii) $R_2$ is alkyl (e.g., isopropyl, isobutyl, isopropyl, 2,2-dimethylpropyl);
(iii) $R_3$ is
   a) D-E-F wherein
      1. D is single bond, alkylene (e.g., methylene) or arylalkylene (e.g., benzylene or —CH$_2$C$_6$H$_4$—);
      2. E is a alkylene (e.g., methylene, ethynylene, prop-2-yn-1-ylene), arylene (e.g., phenylene or —C$_6$H$_4$), alkylarylene (e.g., -benzylene- or —CH$_2$C$_6$H$_4$—), aminoalkylene (e.g., —CH$_2$N(H)—) or amino (e.g., —N(H)—); and
      3. F is alkyl (e.g., isobutyl), aryl (e.g., phenyl), heteroaryl (e.g., pyrid-2-yl, 1,2,4-triazolyl), heteroC$_{3-6}$cycloalkyl (e.g., pyrrolidin-1-yl), amino (e.g., —NH$_2$), $C_{1-6}$alkoxy, or —O-haloalkyl (e.g., —O—CF$_3$);
   b) $R_3$ is a substituted heteroarylaklyl, e.g., substituted with haloalkyl; or
   c) $R_3$ is attached to one of the nitrogen atoms on the pyrazolo portion of Formula XXI and is a moiety of Formula A

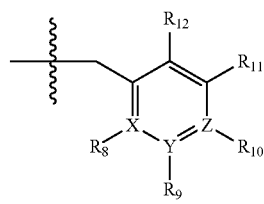

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;

(iv) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl, wherein "alk", "alkyl", "haloalkyl" or "alkoxy" refers to $C_{1-6}$ alkyl and "cycloalkyl" refers to $C_{3-6}$ cycloalkyl;

in free, salt or prodrug form.

The invention further provides compounds of Formula XXI as follows:

21.1. Formula XXI wherein $R_1$ is methyl;
21.2. Formula XXI or 21.1 wherein $R_2$ is $C_{1-6}$ alkyl;
21.3. Formula XXI, 21.1 or 21.2, wherein $R_2$ is isobutyl, 2,2-dimethyl propyl, or 2-methylbutyl;
21.4. Formula XXI or any of 21.1-21.3, wherein $R_2$ is hydroxy $C_{1-6}$ alkyl;
21.5. Formula XXI or any of 21.1-21.3, wherein $R_2$ is 3-hydroxy-2-methyl propyl;
21.6. Formula XXI or 21.1 wherein $R_2$ is $C_{1-6}$ alkoxybenzyl;
21.7. Formula 21.6 wherein $R_2$ is p-methoxybenzyl;
21.8. Formula XXI or 21.1 wherein $R_2$ is $C_{3-6}$ cycloalkyl;
21.9. Formula 21.8 wherein $R_2$ is cyclopentyl or cyclohexyl;
21.10. Formula XXI or 21.1 wherein $R_2$ is $C_{1-6}$ haloalkyl;
21.11. Formula 21.10 wherein $R_2$ is 2,2,2-trifluoroethyl;
21.12. Any of the preceding formulae XXI or any of 21.1-21.11, wherein $R_3$ is a moiety of Formula A wherein $R_8$, $R_9$, $R_{11}$ and $R_{12}$ are each H and $R_{10}$ is phenyl;
21.13. Any of the preceding formulae XXI or any of 21.1-21.12, wherein $R_3$ is a moiety of Formula A wherein $R_8$, $R_9$, $R_{11}$ and $R_{12}$ are each H and $R_{10}$ is pyridyl or thiadizolyl;
21.14. Formula XXI or any of 21.1-21.13, wherein $R_3$ is a moiety of Formula A wherein $R_8$, $R_9$, $R_{11}$ and $R_{12}$ are each H and $R_{10}$ is 2-pyridyl;
21.15. Formula XXI or any of 21.1-21.13, wherein $R_3$ is a moiety of Formula A wherein $R_8$, $R_9$, $R_{11}$ and $R_{12}$ are each H and $R_{10}$ is 4,6-dimethylpyrid-2-yl or 2-pyrrolinyl
21.16. Any of the preceding formulae XXI or any of 21.1-21.15, wherein X, Y and Z are all C,
21.17. Any of the preceding formulae XXI or any of 21.1-21.11 or 21.16, wherein $R_3$ is D-E-F and D is single bond, alkylene (e.g., methylene) or arylalkylene (e.g., -benzyl-);
21.18. Any of the preceding formulae XXI or any of 21.1-21.11 or 21.16-21.17, wherein $R_3$ is D-E-F and D is alkylene (e.g., methylene);
21.19. Any of the preceding formulae XXI or any of 21.1-21.11 or 21.16-21.18, wherein $R_3$ is D-E-F and D is methylene
21.20. Any of the preceding formulae XXI or any of 21.1-21.11 or 21.16-21.16, wherein $R_3$ is D-E-F and D is benzylene;
21.21. Any of the preceding formulae XXI or any of 21.1-21.11 or 21.16-21.20, wherein $R_3$ is D-E-F and E is alkylene (e.g., methylene or ethynylene), arylene (e.g., phenylene), alkylarylene (e.g., -benzylene-), aminoalkylene (e.g., —$CH_2N(H)$—) or amino (e.g., —$N(H)$—);
21.22. Any of the preceding formulae XXI or any of 21.1-21.11 or 21.16-21.21, wherein $R_3$ is D-E-F and E is alkylene (e.g., methylene or ethynylene);
21.23. Any of the preceding formulae XXI or any of 21.1-21.11 or 21.16-21.22, wherein $R_3$ is D-E-F and E is methylene;
21.24. Any of the preceding formulae XXI or any of 21.1-21.11 or 21.16-21.22, wherein $R_3$ is D-E-F and E is ethynylene;
21.25. Any of the preceding formulae XXI or any of 21.1-21.11 or 21.16-21.20, wherein $R_3$ is D-E-F and E is aminoalkylene (e.g., —$CH_2N(H)$—);
21.26. Any of the preceding formulae XXI or any of 21.1-21.11 or 21.16-21.25, wherein $R_3$ is D-E-F and F is alkyl (e.g., isobutyl), aryl (e.g., phenyl), heteroaryl (e.g., pyrid-2-yl, 1,2,4-triazolyl), hetero$C_{3-6}$cycloalkyl (e.g., pyrrolidin-1-yl), amine (e.g., —$NH_2$), alkoxy (e.g., methoxy) or —O-haloalkyl (—$OCF_3$);
21.27. Any of the preceding formulae XXI or any of 21.1-21.11 or 21.16-21.26, wherein $R_3$ is D-E-F and F is aryl (e.g., phenyl);
21.28. Any of the preceding formulae XXI or any of 21.1-21.11 or 21.16-21.27, wherein $R_3$ is D-E-F and F is phenyl;
21.29. Any of the preceding formulae XXI or any of 21.1-21.11 or 21.16-21.25, wherein $R_3$ is D-E-F and F is alkoxy (e.g., methoxy) or —O-haloalkyl (e.g., —$OCF_3$);
21.30. Any of the preceding formulae XXI or any of 21.1-21.11 or 21.16-21.25 or 21.29, wherein $R_3$ is D-E-F and F is methoxy;
21.31. Any of the preceding formulae XXI or any of 21.1-21.11 or 21.16-21.25 or 21.29, wherein $R_3$ is D-E-F and F is —$OCF_3$;
21.32. Any of the preceding formulae XXI or any of 21.1-21.11 or 21.16-21.25, wherein $R_3$ is D-E-F and F is —$NH_2$;

21.33. Any of the preceding formulae XXI or any of 21.1-21.11 or 21.16-21.25, wherein $R_3$ is D-E-F and F is heteroC$_{3-6}$cycloalkyl (e.g., pyrrolidin-1-yl);

21.34. Any of the preceding formulae XXI or any of 21.1-21.11 or 21.16-21.25 or 21.33, wherein $R_3$ is D-E-F and F is pyrrolidin-1-yl;

21.35. Any of the preceding formulae XXI or any of 21.1-21.11 or 21.16-21.25, wherein $R_3$ is D-E-F and F is alkyl (e.g., isobutyl);

21.36. Any of the preceding formulae XXI or any of 21.1-21.11 or 21.16-21.25 or 21.35, wherein $R_3$ is D-E-F and F is isobutyl;

21.37. Any of the preceding formulae XXI or any of 21.1-21.36, wherein $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl;

21.38. Any of the preceding formulae XXI or any of 21.1-21.37, wherein $R_4$ is heterocycloalkyl (e.g., pyrrolidin-3-yl);

21.39. Any of the preceding formulae XXI or any of 21.1-21.38, wherein $R_4$ is pyrrolidin-3-yl);

21.40. Any of the preceding formulae XXI or any of 21.1-21.37 or 21.39, wherein $R_4$ is pyrid-4-yl, pyrid-2-yl or pyrazol-3-yl;

21.41. Any of the preceding formulae XXI or any of 21.1-21.37 or 21.40, wherein $R_4$ is aryl, provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl;

21.42. Any of the preceding formulae XXI or any of 21.1-21.37 or 21.40-21.41, wherein $R_4$ is phenyl, provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl;

21.43. A compound selected from the compounds of Examples 1-5 and 9-11, below; and/or 21.44. Any one of the preceding formulae wherein the compounds inhibit phosphodiesterase-mediated (e.g., PDE1-mediated, especially PDE1B-mediated) hydrolysis of cGMP, e.g., with an IC$_{50}$ of less than 1 µM, preferably less than 25 nM in an immobilized-metal affinity particle reagent PDE assay, for example, as described in Example 1 below;

The invention further provides a Compound of Formula XV, XVI, XVIII or XX as hereinbefore defined as follows:

22.1. Formula XV, XVI, XVIII or XX, wherein $R_2$ is C$_{3-8}$cycloalkyl (e.g., cyclopentyl, cyclohexyl) is substituted with one or more amino (e.g., —NH$_2$), for example, 2-aminocyclopentyl or 2-aminocyclohexyl);

22.2. Formula 22.1, wherein $R_2$ is 2-aminocyclopentyl;

22.3. Formula 22.1, wherein $R_2$ is 2-aminocyclohexyl;

22.4. Formula Formula XV, XVI, XVIII or XX, wherein $R_2$ is 2-aminopropyl;

22.5. Formula XV, XVI, XVIII or XX, wherein $R_2$ is C$_{3-8}$heterocycloalkyl (e.g., pyrrolidinyl, for example, pyrrolidin-3-yl) optionally substituted with C$_{1-6}$alkyl (e.g., methyl), for example, 1-methylpyrrolidin-3-yl;

22.6. Formula 22.5, wherein $R_2$ is pyrrolidinyl (e.g., pyrrolidin-3-yl) optionally substituted with C$_{1-6}$alkyl;

22.7. Formula 22.5, wherein $R_2$ is 1-methylpyrrolidin-3-yl;

22.8. Formula XV, XVI, XVIII or XX, wherein $R_2$ is C$_{3-8}$cycloalkyl-C$_{1-6}$alkyl (e.g., cyclopropylmethyl);

22.9. Formula 22.8, wherein $R_2$ is cyclopropylmethyl;

22.10. Formula XV, XVI, XVIII or XX, or any of 22.1-22.9, wherein $R_4$ is aryl (e.g., phenyl) optionally substituted with one or more halo (e.g., F or Cl) or hydroxyl;

22.11. Formula 22.10, wherein $R_4$ is phenyl optionally substituted with one or more halo;

22.12. Formula 22.10, wherein $R_4$ is phenyl substituted with one or more fluoro or chloro;

22.13. Formula 22.10, wherein $R_4$ is phenyl substituted with one or more hydroxyl;

22.14. Formula XV, XVI, XVIII or XX, or any of 22.1-22.13, wherein $R_3$ is D-E-F and F is amino;

22.15. Formula XV, XVI, XVIII or XX, or any of 22.1-22.13, wherein $R_3$ is D-E-F and F is isopropyl;

22.16. Formula XV, XVI, XVIII or XX, or any of 22.1-22.13, wherein $R_3$ is D-E-F and F is piperidinyl (e.g., piperidin-2-yl);

22.17. Formula XV, XVI, XVIII or XX, or any of 22.1-22.13, wherein $R_3$ is D-E-F and F is pyrrolidin-2-yl;

22.18. Formula XV, XVI, XVIII or XX, or any of 22.1-22.13, wherein $R_3$ is D-E-F and F is 1-methylpyrrolidin-2-yl;

22.19. Formula XV, XVI, XVIII or XX, or any of 22.1-22.13, wherein $R_3$ is D-E-F and F is 1-methylpiperidin-2-yl or 1-ethylpiperidin-2-yl;

22.20. Formula XV, XVI, XVIII or XX, or any of 22.1-22.13, wherein $R_3$ is D-E-F and F is imidazolyl (e.g., imidazol-1-yl);

22.21. Formula XV, XVI, XVIII or XX, or any of 22.1-22.13, wherein $R_3$ is D-E-F and F is 1-methylimidazol-2-yl;

22.22. A compound selected from any of the following:

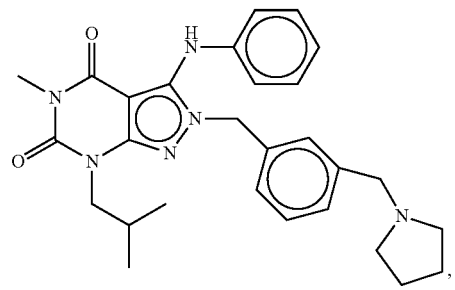

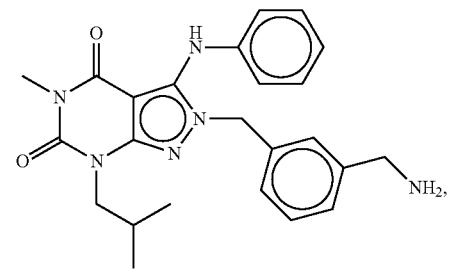

49
-continued
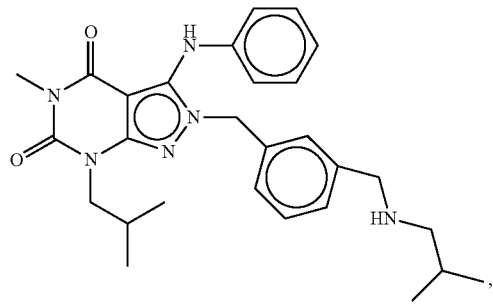
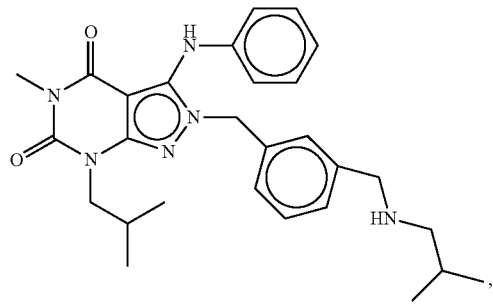
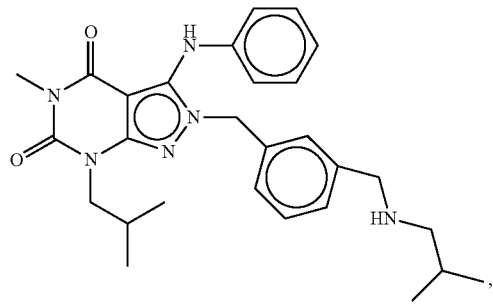
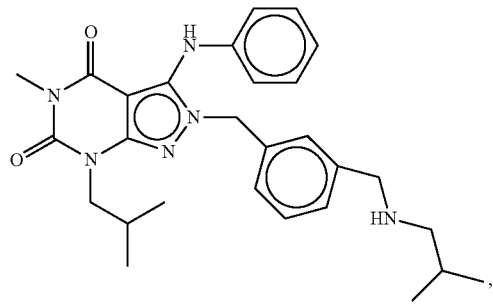
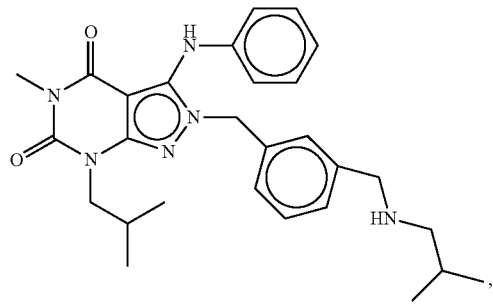
50
-continued
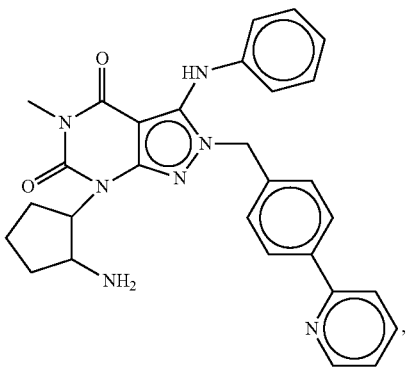
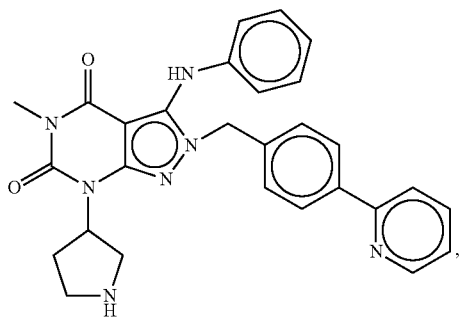
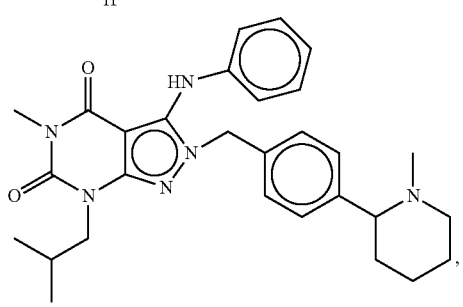
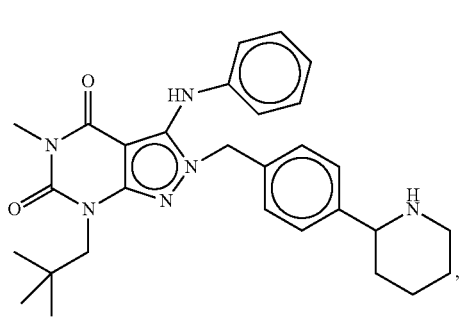
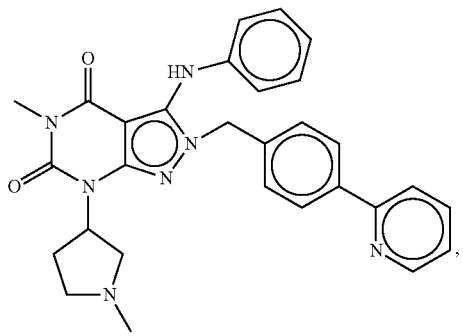

-continued
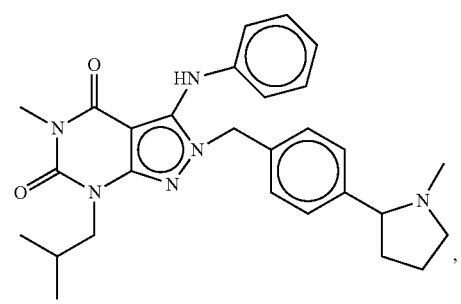
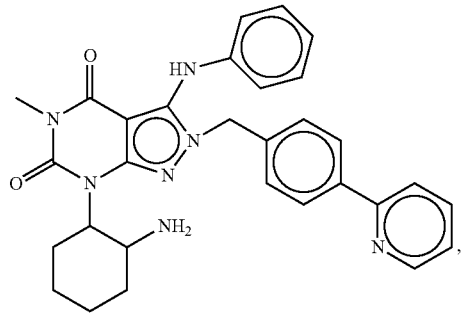
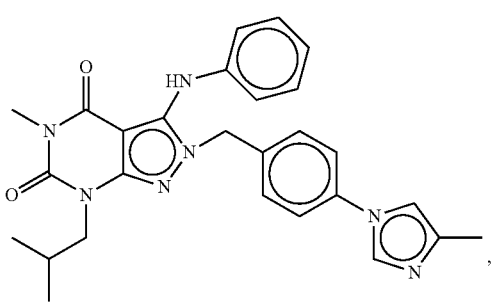
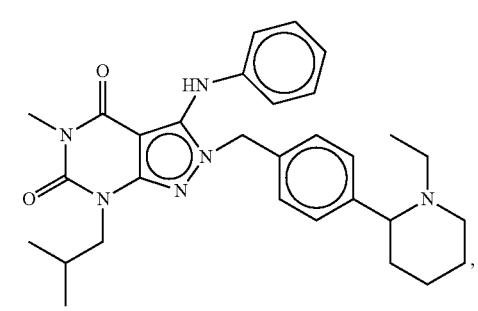
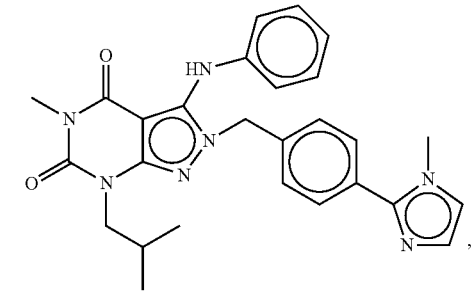
-continued
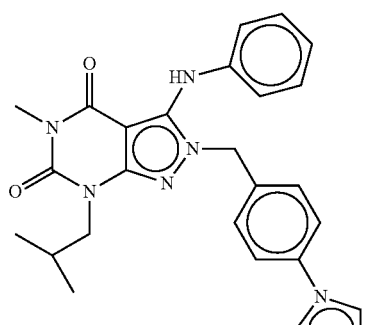
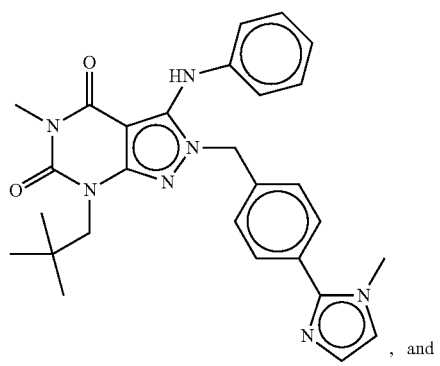
, and
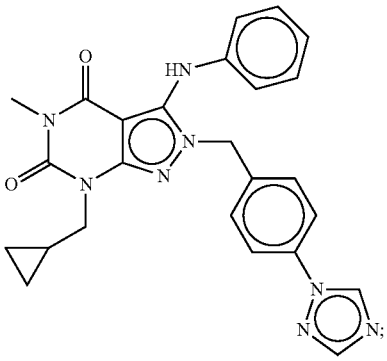
22.23. A compound selected from any of the following:
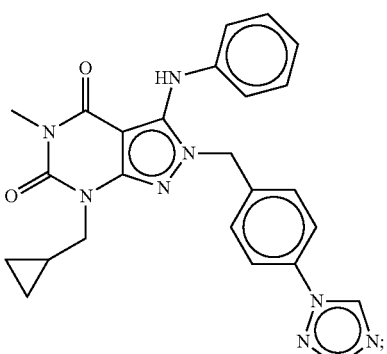

53
-continued
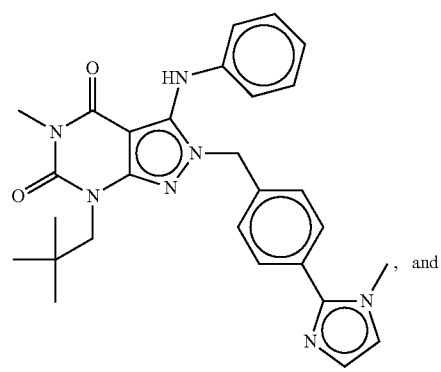, and
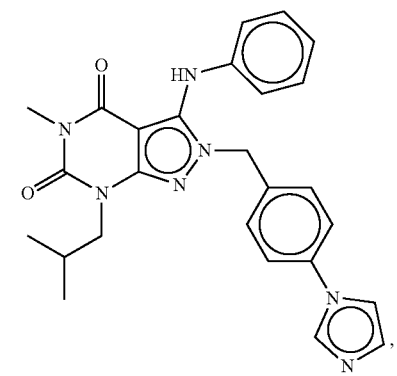,
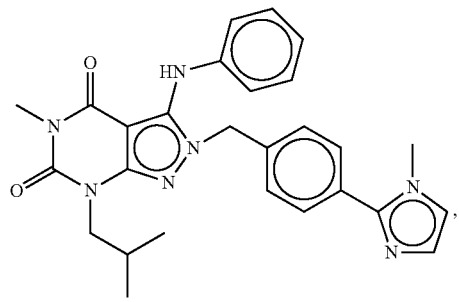,
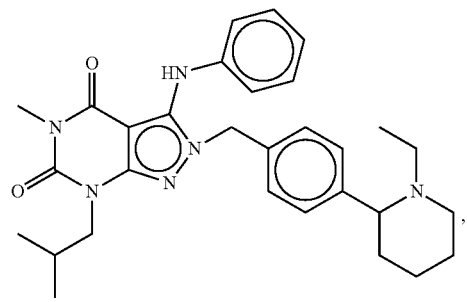,
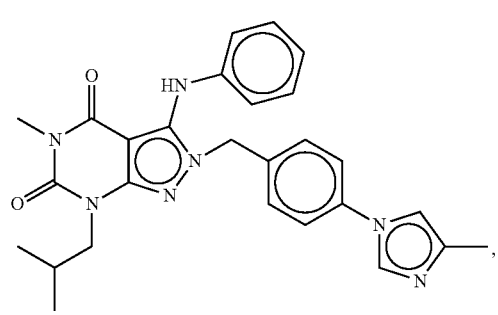,
54
-continued
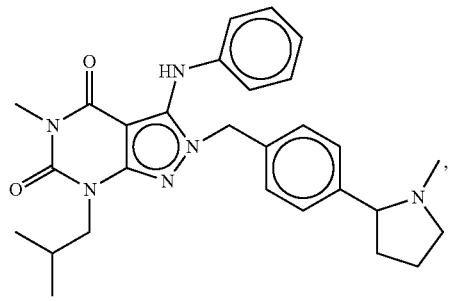,
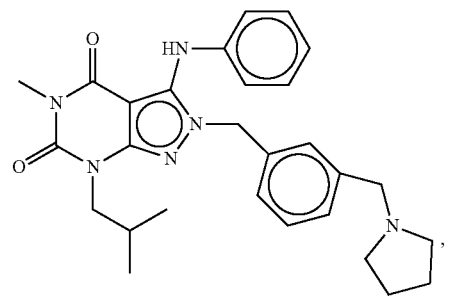,
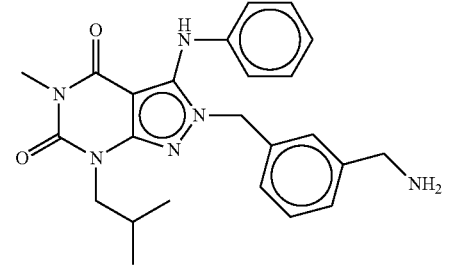,
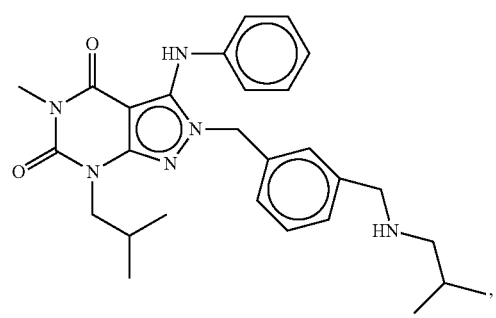,
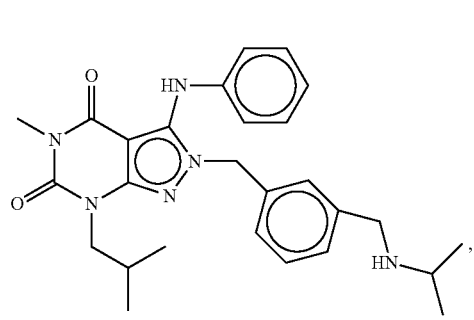, -continued

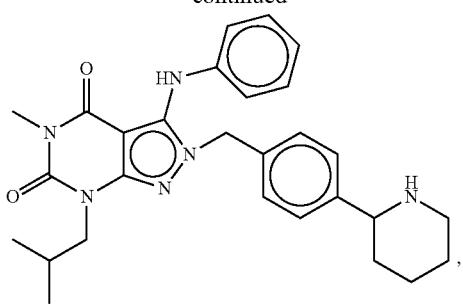

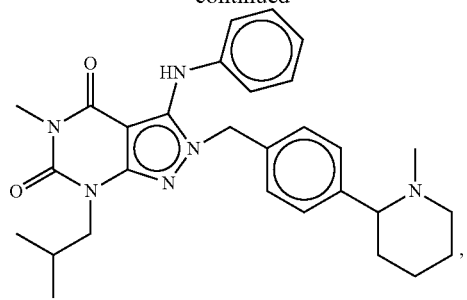

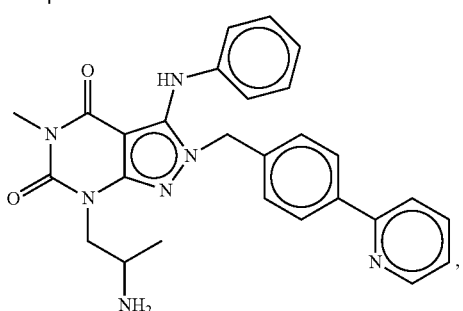

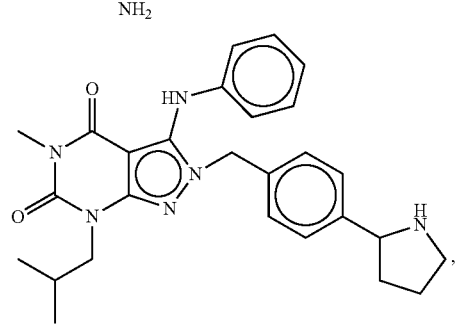

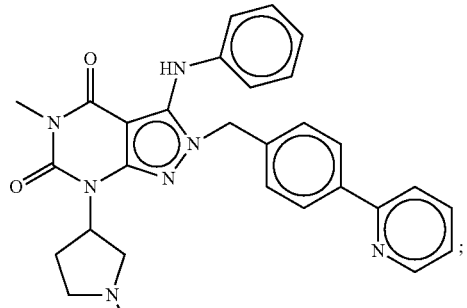

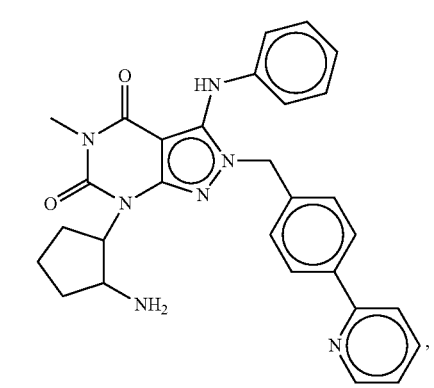

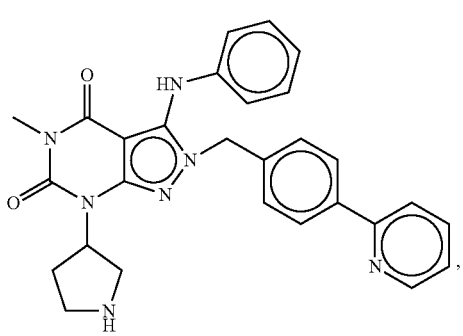

22.24. Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than preferably less than 250 nM, preferably less than 50 nM, more preferably less than 25 nM in an immobilized-metal affinity particle reagent PDE assay, for example, as described in Example 1 below, in free, salt or prodrug form.

In still another embodiment, the PDE 1 Inhibitors for use in the methods of treatment described herein are a 1,3,5-substituted 6,7-dihydro-1H-pyrazolo[4,3-d]pyrimidin-7-one, of formula VI

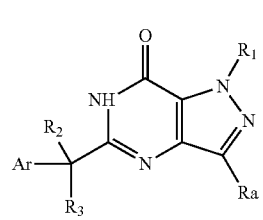

Formula VI wherein
$R_a$ is methyl or $C_2$-$C_6$ alkyl;
$R_1$ is H or $C_1$-$C_4$ alkyl;

each of $R_2$ and $R_3$ is independently selected from H and $C_1$-$C_4$ alkyl, or $R_2$ is H or $C_1$-$C_4$ alkyl and $R_3$ is OH, $C_2$-$C_4$ alkanoyloxy or fluoro, or $R_2$ and $R_3$ when taken together represent $C_2$-$C_6$ alkylene, or $R_2$ and $R_3$ when taken together with the carbon atom to which they are attached represent a carbonyl group;

Ar is either (a)

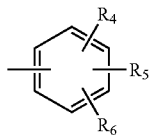

wherein
each of $R_4$, $R_5$ and $R_6$ is independently selected from
H
$C_1$-$C_4$ alkyl,
$C_1$-$C_4$ alkoxy,
$C_1$-$C_4$ alkoxy-Z—,
halo,
halo($C_1$-$C_4$)alkyl,
phenoxy, optionally substituted by up to three substitutents each of which substituent is independently selected from halo, $C_{1-4}$ alkyl, and $C_1$-$C_4$ alkoxy,
nitro,
hydroxy,
hydroxy-Z—,
$C_2$-$C_4$ alkanoyl,
amino,
amino-Z—,
($C_1$-$C_4$ alkyl)NH,
($C_1$-$C_4$ alkyl)$_2$N—,
($C_1$-$C_4$ alkyl)NH—Z—,
($C_1$-$C_4$ alkyl)$_2$N—Z—,
—COOH,
—Z—COOH,
—COO($C_1$-$C_4$ alkyl),
—Z—COO($C_1$-$C_4$ alkyl)
$C_1$-$C_4$ alkanesulphonamido,
$C_1$-$C_4$ alkanesulphonamido-Z—,
halo($C_1$-$C_4$)alkanesulphonamido,
halo($C_1$-$C_4$)alkanesulphonamido-Z—,
$C_1$-$C_4$ alkanamido,
$C_1$-$C_4$ alkanamido-Z—,
HOOC—Z—NH—,
HOOC—Z—NH—Z—,
($C_1$-$C_4$ alkyl)OOC—Z—NH—,
($C_1$-$C_4$ alkyl)OOC—Z—NH—Z—,
$C_1$-$C_4$ alkyl-NH—SO$_2$—NH—,
$C_1$-$C_4$ alkyl-NH—SO$_2$—NH—Z—,
($C_1$-$C_4$ alkyl)$_2$-N—SO$_2$—NH—,
($C_1$-$C_4$ alkyl)$_2$-N—SO$_2$—NH—Z—,
$C_1$-$C_4$ alkoxy CH=CH—Z—CONH—,
$C_1$-$C_4$ alkoxy CH=CHCONH
$C_1$-$C_4$ alkyl-SO$_2$—N($C_1$-$C_4$ alkyl)-,
$C_1$-$C_4$ alkyl-SO$_2$—N($C_1$-$C_4$ alkyl)-Z—,
($C_1$-$C_4$ alkyl)NH—Z—SO$_2$—NH—,
($C_1$-$C_4$ alkyl)$_2$N—Z—SO$_2$—NH—,
($C_1$-$C_4$ alkyl)NH—Z—SO$_2$—NH—Z—,
($C_1$-$C_4$ alkyl)$_2$N—Z—SO$_2$—NH—Z—,
benzenesulphonamido, optionally ring substituted by up to three substituents each of which is independently selected from halo, $C_{1-4}$ alkyl, and $C_1$-$C_4$ alkoxy,
$C_1$-$C_4$ alkanoyl-N($C_1$-$C_4$ alkyl)-,
$C_1$-$C_4$ alkanoyl-N($C_1$-$C_4$ alkyl)-Z—,
$C_1$-$C_4$ alkoxycarbonyl-CH(CH$_2$OH)NHSO$_2$—,
—SO$_3$H,
—SO$_2$NH$_2$,
H$_2$NOC—CH(CH$_2$OH)—NHSO$_2$—,
HOOC—Z—O—, and
($C_1$-$C_4$ alkyl)OOC—Z—O—,
or optionally one of $R_4$, $R_5$ and $R_6$ is a G-Het group and wherein the others of $R_4$, $R_5$ and $R_6$ are independently selected from the $R_4$, $R_5$ and $R_6$ substitutents listed above;

Z is $C_1$-$C_4$ alkylene,
G is a direct link, Z, O, —SO$_2$NH—, SO$_2$, or —Z—N($C_1$-$C_4$ alkyl)SO$_2$—,
Het is a 5- or 6-membered heterocyclic group containing 1, 2, 3 or 4 nitrogen heteroatoms; or 1 or 2 nitrogen heteroatoms and 1 sulphur heteroatom or 1 oxygen heteroatom; or the heterocyclic group is furanyl or thiophenyl; wherein the Het group is saturated or partially or fully unsaturated and optionally substituted by up to 3 substitutents, wherein each substitutent is independently selected from $C_1$-$C_4$ alkyl, oxo, hydroxy, halo, and halo($C_1$-$C_4$) alkyl;
or (b) any one of the following bicyclic groups:
benzodioxolanyl,
benzodioxanyl,
benzimidazolyl,
quinolinyl,
indolyl,
quinazolinyl,
isoquinolinyl,
benzotriazolyl,
benzofuranyl,
benzothiophenyl,
quinoxalinyl, or
phthalizinyl,
wherein said bicyclic Ar groups are linked to the neighbouring —C($R_2R_3$)— group via the benzo ring portion, and wherein the heterocyclic portion of said bicyclic Ar group is optionally partially or fully saturated, said group being optionally substituted by one or more of $C_1$-$C_1$ alkyl, halo, hydroxy, oxo, amino, and alkoxy;
or a pharmaceutically acceptable salt of the compound, or a pharmaceutically acceptable solvate of the compound or the salt.

For example, PDE 1 Inhibitors for use in the present invention include 1,3,5,-substituted, 6,7-dihydro-1H-pyrazolo[4,3-d]pyrimidin-7-one, in free or pharmaceutically acceptable salt form, particularly compounds of Formula VI or the following formulae:
3.2 of Formula VI wherein $R_a$ is a $C_{2-5}$ alkyl group;
3.3 of Formula VI wherein $R_a$ is a $C_{2-4}$ alkyl group;
3.4 of Formula VI wherein $R_a$ is a $C_3$ alkyl group;
3.5 of Formula VI wherein $R_a$ is methyl;
3.6 of Formula VI, 3.2, 3.3, 3.4 or 3.5 wherein $R_1$ is a $C_{1-6}$ alkyl group;
3.7 of any of the preceding formulae wherein $R_1$ is a $C_{1-3}$ alkyl group;
3.8 Of any of the preceding formulae wherein $R_1$ is a methyl group;
3.9 of any of the preceding formulae wherein $R_2$ is H,
3.10 of any of the preceding formulae wherein $R_3$ is H,
3.11 of any of the preceding formulae wherein $R_4$, $R_5$ and $R_6$ are independently selected from H, ($C_{1-4}$ alkyl)$_2$N—, $C_{1-4}$ alkanesulphonamido and benzenesulphonamido;

3.12 of any of the preceding formulae wherein $R_4$, $R_5$ and $R_6$ are independently selected from H, diethylamino, methanesulphonamido and benzenesulphonamido;

3.13 of any of the preceding formulae wherein Ar is 4-diethylaminophenyl;

3.14 of any of the preceding formulae wherein Ar is 2-methanesulphonamidophenyl;

3.15 of any of the preceding formulae wherein Ar is 4-benzenesulphonamidophenyl;

3.16 of any of the preceding formulae wherein one of $R_4$, $R_5$ and $R_6$ is $(C_{1-4}$ alkyl$)_2$N— and wherein the other two of $R_4$, $R_5$ and $R_6$ are H.

3.17 of any of the preceding formulae wherein one of $R_4$, $R_5$ and $R_6$ is diethylamino and wherein the other two of $R_4$, $R_5$ and $R_6$ are H.

3.18 of any of the preceding formulae wherein $R_a$ is methyl;

3.19 of any of the preceding formulae wherein $R_a$ is $C_2$-$C_6$ alkyl;

3.20 of any of the preceding formulae wherein the compound is selected from the following:

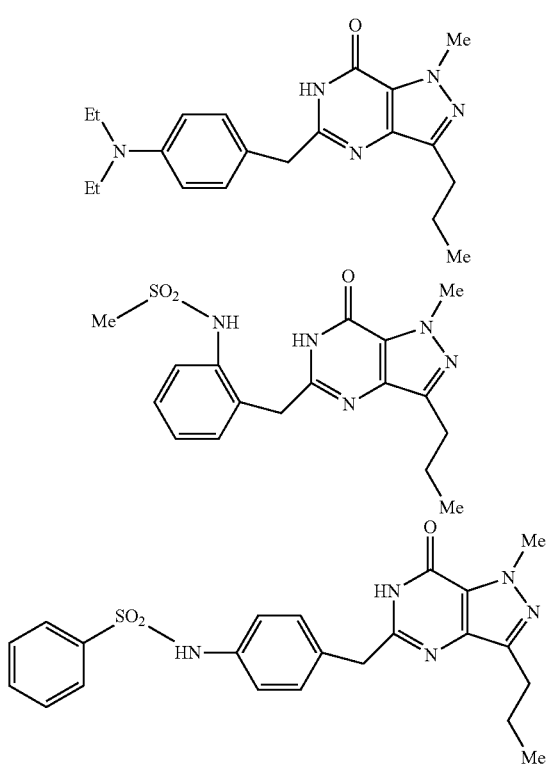

3.21 of any of the preceding formulae wherein the compound is

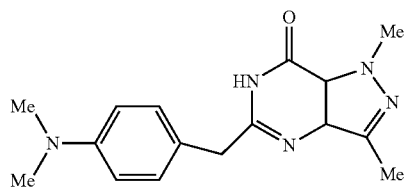 [SMILES: CC1=NN(C)C2C(=O)NC(Cc3ccc(N(C)C)cc3)=NC12]

in free or salt form;

3.22 A compound which is a 1,3,5,-substituted, 6,7-dihydro-1H-pyrazolo[4,3-d]pyrimidin-7-one, in free or pharmaceutically acceptable salt form, e.g. a compound of Formula VI or according to any of formulae 3.2-3.21, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

In another embodiment, the PDE 1 Inhibitors for use in the methods of treatment described herein are substituted (imidazo, pryimido or diazepino)[2,1-b]purin-4-ones of Formula VIIa or VIIb:

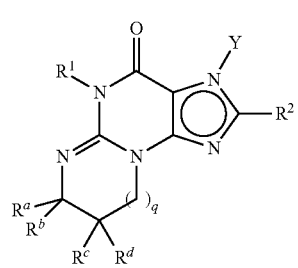

Formula VIIa

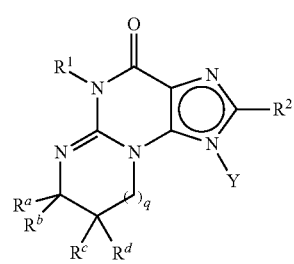

Formula VIIb in free, salt or prodrug form, including its enantiomers, diasterisomers and racemates, wherein:
i) q=0, 1 or 2;
ii) $R^1$, $R^a$, $R^b$, $R^c$ and $R^d$ are each independently H, alkyl, aryl, heteroaryl, cycloalkyl or heterocycloalkyl groups, wherein each alkyl group of $R^1$, $R^a$, $R^b$, $R^c$ and $R^d$ is independently unsubstituted or substituted with 1 to 5 independently selected $R^3$ moieties which can be the same or different, each $R^3$ moiety being independently selected from the group consisting of hydroxy, alkoxy, cycloalkoxy, aryloxy, alkylthio, arylthio, aryl, haloaryl, heteroaryl, cycloalkyl, heterocycloalkyl, amino, alkylamino, dialkylamino, cycloalkylamino and heterocycloalkylamino groups;
wherein each of the aryl, heteroaryl, cycloalkyl and heterocycloalkyl groups of $R^1$, $R^a$, $R^b$, $R^c$ and $R^d$ is independently unsubstituted or substituted with 1 to 5 independently selected $R^4$ moieties which can be the same or different, each $R^4$ moiety being independently selected from the group consisting of: halo, optionally substituted aryl (e.g., phenyl, chlorophenyl, methoxyphenyl), heteroaryl (e.g., pyridyl, pyrrolyl), nitro, cyano, haloalkyl, haloalkoxy, alkyl, alkoxy, cycloalkyl, heterocycloalkyl (e.g., pyrrolidinyl, morpholin-4-yl, pyrrol-1-yl), cycloalkylalkyl, amino, alkylamino, dialkylamino, —$OCF_3$, acyloxy, —$OR^8$, —$C(O)R^9$, —$C(O)OR^8$, —$NR^{10}C(O)R^9$, —$NR^{10}C(O)OR^8$, —$NR^{10}S(O)_2R^9$, —$S(O)_{0-2}R^9$ groups, carbonyl when two hydrogens attached to the same carbon atom of the cycloalkyl or heterocycloalkyl group of $R^1$ are substituted, and $=CR^8R^9$ when two hydrogens attached to the same carbon atom of the cycloalkyl or heterocycloalkyl groups of $R^1$ are substituted, wherein each of the aryl, heteroaryl, cycloalkyl and heterocycloalkyl groups of the $R^3$ and $R^4$ moieties above is independently unsubstituted or substituted with 1 to 5 independently selected $R^{12}$ moieties which can be the same or different, each $R^{12}$ moiety being independently selected from the group consisting of: halo, phenyl, nitro, cyano, haloalkyl, haloalkoxy, alkyl, cycloalkyl, cycloalkylalkyl, amino, alkylamino, $-OCF_3$, acyloxy, $-OR^8$, $-C(O)R^9$, $-C(O)OR^8$, $-NR^{10}C(O)R^9$, $-NR^{10}C(O)OR^8$, $-NR^{10}S(O)_2R^9$, $-S(O)_{0-2}R^9$ groups, carbonyl when two hydrogens attached to the same carbon atom of the cycloalkyl or heterocycloalkyl group of $R^3$ or $R^4$ are substituted, and $=CR^8R^9$ when two hydrogens attached to the same carbon atom of the cycloalkyl or heterocycloalkyl group of $R^3$ or $R^4$ are substituted; or iii) $R^a$ and $R^b$, together with the carbon to which they are both attached, form a 4- to 7-membered cycloalkyl or heterocycloalkyl ring, and $R^c$ and $R^d$ are each independently H or an alkyl group; or iv) $R^a$ and $R^c$, together with the respective carbons to which they are attached, form a 4- to 7-membered cycloalkyl or heterocycloalkyl ring, and $R^b$ and $R^d$ are each independently H or an alkyl group, preferably $R^a$ and $R^c$ together have the cis configuration, e.g., where the carbons carrying $R^a$ and $R^c$ have the R and S configurations, respectively;

v) $R^2$ is H, halo, alkyl, haloalkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group, wherein each alkyl group of $R^2$ is independently unsubstituted or substituted with 1 to 5 independently selected $R^{13}$ moieties which can be the same or different, each $R^{13}$ moiety being independently selected from the group consisting of halo, hydroxy, alkoxy, alkyl, aryl (e.g., phenyl, naphthyl) heteroaryl (e.g., 1H-imidazol-2-yl), cycloalkyl, heterocloalkyl (e.g., pyrrolidin-1-yl), amino, monoalkylamino or dialkylamino group, wherein each aryl group of $R^{13}$ is independently unsubstituted or substituted with 1 to 5 independently selected $R^4$ moieties which can be the same or different;

vi) Y is H or an alkyl group substituted with (i) an aryl, heteroaryl, cycloalkyl, hydroxy, alkoxy, amino, monoalkylamino or dialkylamino group, or (ii) an aryl group substituted with from one to three moieties each independently selected from the group consisting of: halo, alkyl, phenyl, hydroxy, alkoxy, phenoxy, amino, monoalkylamino and dialkylamino group;

vii) each $R^8$ is independently H, alkyl or aryl;

viii) each $R^9$ is independently H, alkyl, aryl or $-NR^{10}R^{11}$;

ix) each $R^{10}$ is independently H, alkyl, aryl, heteroaryl, arylalkyl or heteroarylalkyl, wherein each alkyl, aryl, heteroaryl, arylalkyl or heteroarylalkyl of $R^{10}$ is unsubstituted or independently substituted with 1 to 5 $R^{14}$ moieties which can be the same or different, each $R^{14}$ moiety being independently selected from the group consisting of: halo, alkyl, aryl, cycloalkyl, $-CF_3$, $-OCF_3$, $-CN$, $-OR^8$, $-CH_2OR^8$, $-C(O)OR^8$ and $-C(O)NR^8R^8$; and x) each $R^{11}$ is independently H, alkyl, aryl, heteroaryl, arylalkyl or heteroarylalkyl, wherein each alkyl, aryl, heteroaryl, arylalkyl or heteroarylalkyl of $R^{11}$ is unsubstituted or independently substituted with 1 to 5 $R^{14}$ moieties which can be the same or different.

The invention further provides the use of PDE 1 Inhibitors of Formula VIIIa or VIIb, in free or salt form, as follows:

4.1: Formula VIIa or VIIb, wherein q=0, 1 or 2;

4.2: Formula VIIa or VIIb, wherein q=0;

4.3: Formula VIIa or VIIb or 4.1 or 4.2, wherein $R^1$ is alkyl;

4.4: Formula VIIIa or VIIb or 4.1-4.3, wherein $R^1$ is methyl;

4.5: Formula VIIa or VIIb or 4.1-4.4, wherein $R^a$ and $R^c$, together with the respective carbons to which they are attached, form a 4- to 7-membered cycloalkyl or heterocycloalkyl ring, and $R^b$ and $R^d$ are each independently H or an alkyl group;

4.6: Formula VIIa or VIIb or 4.1-4.4, wherein $R^a$ and $R^c$, together with the respective carbons to which they are attached, form a 5-membered heterocycloalkyl ring, and $R^b$ and $R^d$ are each independently H, 4.7: Formula 4.6 wherein $R^a$ and $R^c$ together have a cis configuration;

4.8: Formula VIIa or VIIb or 4.1-4.4, wherein $R^a$ and $R^b$, together with the respective carbons to which they are attached, form a 5-membered heterocycloalkyl ring, and $R^c$ and $R^d$ are each independently H, 4.9: Formula VIIIa or VIIb or 4.1-4.7, wherein $R^2$ is alkyl or haloalkyl;

4.10: Formula VIIa or VIIb or 4.1-4.7, wherein $R^2$ is biphenyl-4-ylmethyl;

4.11: Formula VIIa or VIIb or 4.1-4.7, wherein $R^2$ is benzyl;

4.12: Formula VIIa or VIIb or 4.1-4.7, wherein $R^2$ is cyclopentylmethyl;

4.13: Formula VIIa or VIIb or 4.1-4.7, wherein $R^2$ is cyclopropylmethyl; and/or 4.14: Formula VIIa or VIIb or 4.1-4.12, wherein Y is benzyl;

4.15: Of any of the preceding formulae wherein the compound is selected from the following:

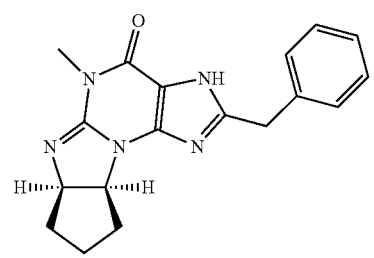

-continued

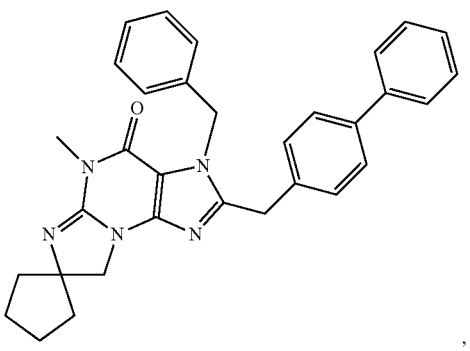

,

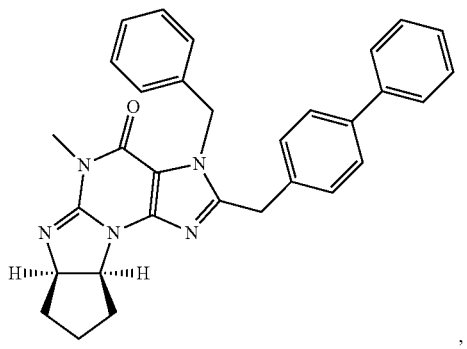

,

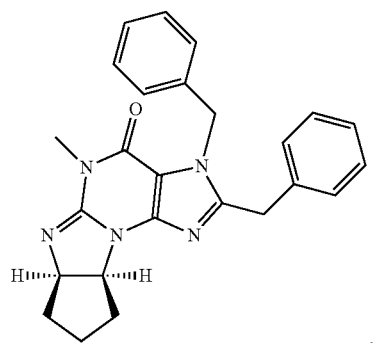

,

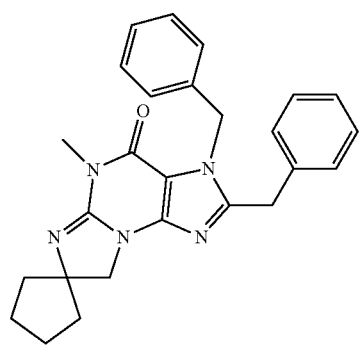

4.16: Of any of the preceding formulae wherein the compound is

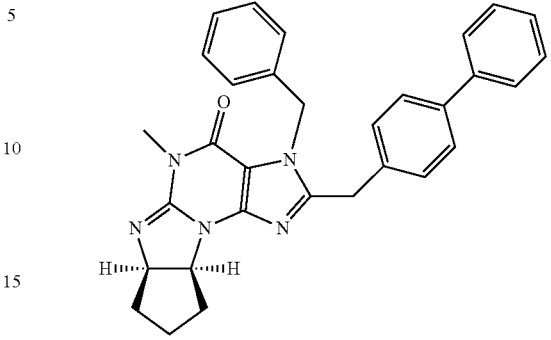

in free or salt form;

4.17: A compound which is a substituted imidazo[2,1-b]purin-4-one, in free or pharmaceutically acceptable salt form, e.g. a compound of Formula VIIa or according to any of formulae 4.1-4.16, wherein the compound inhibits phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 1 below.

Preferably, compounds of Formula VIIa or VIIb are selected from a group consisting of (6aR,9aS)-5,6a,7,8,9,9a-hexahydro-5-methyl-2,3-bis(phenylmethyl)-cyclopent[4,5]imidazo[2,1-b]purin-4(3H)-one, (6aR,9aS)-2-(biphenyl-4-ylmethyl)-5,6a,7,8,9,9a-hexahydro-5-methyl-3-(phenylmethyl)cyclopent[4,5]imidazo[2,1-b]purin-4(3H)-one, 5'-methyl-2',3'-bis(phenylmethyl)spiro[cyclopentane-1,7'(8'H)-[3H]imidazo[2,1-b]purin]-4'(5'H)-one and 5'-methyl-2'-(biphenyl-4-ylmethyl)-3'-(phenylmethyl)spiro-[cyclopentane-1,7'(8'H)-[3H]imidazo[2,1-b]purin]-4'(5'H)-one, in free or pharmaceutically acceptable salt form.

In an especially preferred embodiment, compound of Formula VIIa is (6aR,9aS)-2-(biphenyl-4-ylmethyl)-5,6a,7,8,9,9a-hexahydro-5-methyl-3-(phenylmethyl)cyclopent-[4,5]imidazo[2,1-b]purin-4(3H)-one, in free or salt form.

The numbering of substituted imidazo[2,1-b]purin-4-one of Formula VIIa or VIIb as described herein is shown below as an example, wherein q=0:

Formula VIIa

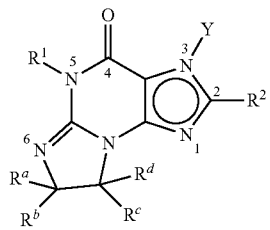

Formula VIIb

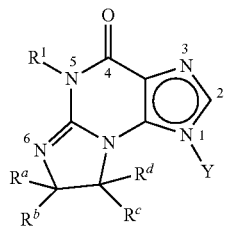

wherein q=1:

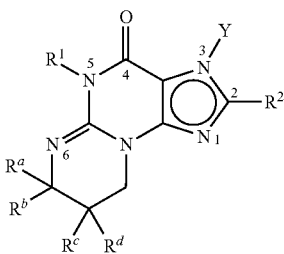

Formula VIIa

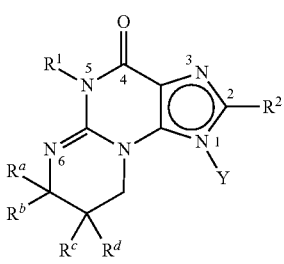

Formula VIIb

In another embodiment, the PDE 1 Inhibitors for use in the methods of treatment described herein are Compounds of Formula VIIIa or VIIIb:

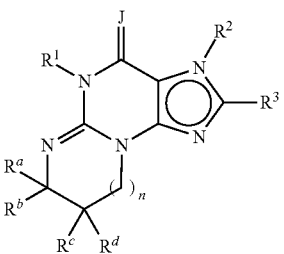

Formula VIIIa

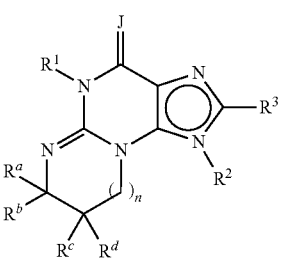

Formula VIIIb in free or salt form, wherein:
J is oxygen or sulfur,
$R^1$ is hydrogen, alkyl or alkyl substituted with aryl or hydroxy;
$R^2$ is hydrogen, aryl, heteroaryl, cycloalkyl, alkyl or alkyl substituted with aryl, heteroaryl, hydroxy, alkoxy, amino, monoalkyl amino or dialkylamino, or —$(CH_2)_m$ TCOR$^{20}$ wherein m is an integer from 1 to 6, T is oxygen or —NH— and $R^{20}$ is hydrogen, aryl, heteroaryl, alkyl or alkyl substituted with aryl or heteroaryl;
$R^3$ is hydrogen, halo, trifluoromethyl, alkoxy, alkylthio, alkyl, cycloalkyl, aryl, aminosulfonyl, amino, monoalkylamino, dialkylamino, hydroxyalkylamino, aminoalkylamino, carboxy, alkoxycarbonyl or aminocarbonyl or alkyl substituted with aryl, hydroxy, alkoxy, amino, monoalkylamino or dialkylamino;
$R^a$, $R^b$, $R^c$ and $R^d$ independently represent hydrogen, alkyl, cycloalkyl or aryl; or ($R^a$ and $R^b$) or ($R^c$ and $R^d$) or ($R^b$ and $R^c$) can complete a saturated ring of 5- to 7-carbon atoms, or ($R^a$ and $R^b$) taken together and ($R^b$ and $R^c$) taken together, each complete a saturated ring of 5- to 7-carbon atoms, wherein each ring optionally can contain a sulfur or oxygen atom and whose carbon atoms may be optionally substituted with one or more or the following: alkenyl, alkynyl, hydroxy, carboxy, alkoxycarbonyl, alkyl or alkyl substituted with hydroxy, carboxy or alkoxycarbonyl; or such saturated ring can have two adjacent carbon atoms which are shared with an adjoining aryl ring; and
n is zero or one.

The invention further provides the use of PDE 1 Inhibitors of Formula VIIIa or VIIIb as follows:
5.1: Formula VIIIa or VIIIb, wherein J=O
5.2: Formula VIIIa or VIIIb or 5.1, wherein $R^1$ is alkyl.
5.3: Formula VIIIa or VIIIb, 5.1 or 5.2, wherein $R^2$ is hydrogen, benzyl, 4-chlorobenzyl, cyclohexylmethyl or trimethylacetoxymethyl.
5.4: Formula VIIIa or VIIIb, 5.1, 5.2 or 5.3, wherein $R^3$ is hydrogen, or alkyl such as methyl or ethyl.
5.5: Formula VIIIa or VIIIb, 5.1, 5.2, 5.3 or 5.4, wherein n is zero; and
5.6: Formula VIIIa or VIIIb, 5.1, 5.2, 5.3, 5.4 or 5.5, wherein $R^a$ and $R^b$ form a saturated 5 membered ring, or ($R^b$ and $R^c$) form a saturated 5, 6 or 7 membered ring, or ($R^a$ and $R^b$) and ($R^b$ and $R^c$) each complete a saturated ring and each ring contains 5 or 6 carbon atoms.
5.7 Formula VIIIa or VIIIb, in free or salt form, selected from the following:
cis-5,6a,7,8,9,9a-Hexahydro-5-methyl-3-(phenylmethyl)cyclopenta[4,5]imidazo-[2,1-b]purin-4-one;
7,8-Dihydro-5-methyl-3-(phenylmethyl)-3H-imidazo[2,1-b]purin-4(5H)-one;
cis-6a,7,8,9,10,10a-Hexahydro-5-methyl-3-(phenylmethyl)-3H-benzimidazo[2,1-b]purin-4(5H)-one;
5,7,8,9-Tetrahydro-5-methyl-3-(phenylmethyl)pyrimido[2,1-b]purin-4(3H)-one;
7,8-Dihydro-8-phenyl-5-methyl-3-(phenylmethyl)-3H-imidazo[2,1-b]purin-4(5H)-one;
5',7'-Dihydro-5'-methyl-3'-(phenylmethyl)spiro[cyclohexane-1,8'-(8H)imidazo-[2,1-b]purin]-4'(3'H)-one;
cis-5,6a,11,11a-Tetrahydro-5-methyl-3-(phenylmethyl)indeno[1',2':4,5]imidazo-[2,1-b]purin-4(3H)-one;
5',7'-Dihydro-2',5' dimethyl-3'-(phenylmethyl)spiro {cyclohexane-1,7'(8'H)-imidazo[2,1-b]purin}-4'-(3'H)-one;
7,8-Dihydro-2,5,7,7,8(R,S)-pentamethyl-3H-imidazo[2,1-b]purin-4(5H)-one;
cis-5,6a,7,11b-Tetrahydro-5-methyl-3-(phenylmethyl)indeno[2',1',4,5]imidazo[2,1-b]purin-4(3H)-one;
cis-5,6a,7,8,9,9a-Hexahydro-2,5-dimethyl-3-(phenylmethyl)cyclopent[4,5]-imidazo[2,1-b]purin-4-(3H)-one;
5'-Methyl-3'-(phenylmethyl)-spiro[cyclopentane-1,7'-(8'H)-(3'H)imidazo[2,1-b]purin]-4-(5'H)-one;
7,8-Dihydro-2,5,7,7-tetramethyl-3-(phenylmethyl)-3H-imidazo[2,1-b]purin-4(5'H)-one;
7,8-Dihydro-7(R)-phenyl-2,5-dimethyl-3-(phenylmethyl)-3H-imidazo[2,1-b]purin-4(5H)-one;
7,8-Dihydro-2,5-dimethyl-3,7(R)-bis(phenylmethyl)-3H-imidazo[2,1-b]purin-4(5H)-one;
(±)-7,8-Dihydro-2,5-dimethyl-7-ethyl-3-(phenylmethyl)-3H-imidazo[2,1-b]purin-4(5H)-one;

6a(S)-7,8,9,10,10a(R)-Hexhydro-2,5-dimethyl-3-(phenylmethyl)-3H-benzimidazo[2,1-b]purin-4(5H)-one;

6a(R)-7,8,9,10,10a(S)-hexahydro-2,5-dimethyl-3-(phenylmethyl)-3H-benzimidazo-[2,1-b]purin-4(5H)-one;

7,8-Dihydro-2,5-dimethyl-7(R)-isopropyl-3-(phenylmethyl)-3H-imidazo[2,1-b]purin-4(5H)-one;

7,8-Dihydro-2,5,7(R)-trimethyl-3-(phenylmethyl)-3H-imidazo[2,1-b]purin-4(5H)-one;

cis-7,7a,8,9,10,10a-Hexahydro-2,5-dimethyl-3-(phenylmethyl)-3H-cyclopenta-[5,6]pyrimido[2,1-b]purin-4(5H)-one;

7,8-Dihydro-2,5-dimethyl-7(S)-(1-methylpropyl)-3-(phenylmethyl)-3H-imidazo-[2,1-b]purin-4(5H)-one;

7,8-Dihydro-2,5-dimethyl-7(R)-(2-methylpropyl)-3-(phenylmethyl)-3H-imidazo-[2,1-b]purin-4(5H)-one;

7,8-Dihydro-2,5-dimethyl-7(R,S)-(methoxycarbonyl)-3-(phenylmethyl)-3H-imidazo[2,1-b]purin-4(5H)-one;

7,8-Dihydro-2,5-dimethyl-7(R,S)-(1-propyl)-3-(phenylmethyl)-3H-imidazo[2,1-b]purin-4(5H)-one;

7,8-Dihydro-2,5-dimethyl-7(S)-(1-methylethyl)-3-(phenylmethyl)-3H-imidazo[2,1-b]purin-4(5H)-one;

7,8-Dihydro-2,5,7,7,8(R,S)-pentamethyl-3H-imidazo[2,1-b]purin-4(5H)-one;

5,7,8,9-Tetrahydro-2,5,7,9(R,S)-pentamethyl-3-(phenylmethyl)-pyrimido[2,1-b]purin-4(3H)-one;

5,6a(R),7,8,9,9a(S)-Hexahydro-2,5-dimethyl-3-(phenylmethyl)cyclopent-[4,5]imidazo[2,1-b]purin-4(3H)-one;

5,6a(S),7,8,9,9a(R)-Hexahydro-2,5-dimethyl-3-(phenylmethyl)cyclopent-[4,5]imidazo[2,1-b]purin-4(3H)-one;

cis-6a,7,8,9,10,10a-Hexahydro-2,5-dimethyl-3-(phenylmethyl)-3H-benzimidazo[2,1-b]purin-4(5H)-one;

5',7'-Dihydro-2',5'-dimethyl-3'-(phenylmethyl)spiro[cyclohexane-1,8-(8H)-imidazo[2,1-b]purin]-4-(3'H)-one;

cis-5,6a,7,8,9,9a-Hexahydro-2,5-dimethyl-3-(phenylmethyl)cyclohept-[6,7]imidazo[2,1-b]purin-4(3H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-6a,7,8,9,10,10a-Hexahydro-5-methyl-2-ethyl-3-(phenylmethyl)-3H-benzimidazo[2,1-b]purin-4-(5H)-one;

cis-5,6a,7,8,9,9a-Hexahydro-5-methyl-2-ethyl-3-(phenylmethyl)cyclopent-[4,5]imidazo[2,1-b]purin-4(3H)-one;

cis-5,6a,7,8,9,9a-Hexahydro-5-methyl-2-phenyl-3-(phenylmethyl)cyclopent-[4,5]imidazo[2,1-b]purin-4(3H)-one;

cis-6a,7,8,9,10,10a-Hexahydro-5-methyl-2-phenyl-3-(phenylmethyl)-3H-benzimidazo[2,1-b]purin-4-(5H)-one;

cis-5,6a,7,8,9,9a-Hexahydro-5-methylcyclopenta[4,5]imidazo[2,1-b]purin-4(3H)-one;

cis-5,6a,7,8,9,9a-Hexahydro-2,5-dimethylcyclopenta[4,5]imidazo[2,1-b]purin-4(3H)-one;

cis-5,6a(R), 7,8,9,9a(S)-Hexahydro-2,5-di-methylcyclopent[4,5]imidazo[2,1-b]purin-4(3H)-one;

2',5'-dimethyl-spiro{cyclopentane-1,7'-(8'H)-(3'H)-imidazo[2,1-b]purin}-4'(5'H)-one;

7,8-Dihydro-2,5-dimethyl-7(R)-(1-methylethyl)-3H-imidazo[2,1-b]purin-4(5H)-one;

7,8-Dihydro-2,5,7,7-tetramethyl-3H-imidazo[2,1-b]purin-4(5H)-one;

7,8-Dihydro-2,5-dimethyl-7(S)-(1-methylethyl)-3H-imidazo[2,1-b]purin-4(5H)-one;

6a(R),7,8,9,10,10a(S)-Hexahydro-2,5-dimethyl-3H-benzimidazo[2,1-b]purin-4(5H)-one;

5',7'-Dihydro-2',5'-dimethylspiro{cyclohexane-1,7-(8'H)-imidazo[2,1-b]purin}-4'(3'H)-one;

cis-5,6a,7,8,9,9a-Hexahydro-5-methyl-3-(phenylmethyl)cyclopenta[4,5]-imidazo[2,1-b]purin-4(3H)-thione;

5,6a(R),7,8,9,9a(S)-Hexahydro-2,5-dimethyl-3-(phenylmethyl)cyclopent-[4,5]imidazo[2,1-b]purin-4(3H)-thione;

cis-5,6a,7,8,9,9a-Hexahydro-5-methyl-3-(4-chlorophenylmethyl)cyclopenta[4,5]-imidazo[2,1-b]purin-4(3H)-one;

cis-5,6a,7,8,9,9a-Hexahydro-5-methyl-3-(cyclohexylmethyl)cyclopent[4,5]-imidazo[2,1-b]purin-4(3H)-one;

cis-5,6a,7,8,9,9a-Hexahydro-5-methyl-3-(2-naphthylmethyl)cyclopent[4,5]-imidazo[2,1-b]purin-4(3H)-one;

5,6a(R),7,8,9,9a(S)-Hexahydro-2,5-dimethyl-3-(4-bromophenylmethyl)-cyclopent[4,5]imidazo[2,1-b]purin-4(3H)-one;

5,6a(R)-7,8,9,9a(S)-Hexahydro-2,5-dimethyl-3-(4-methoxyphenylmethyl)-cyclopent[4,5]imidazo[2,1-b]purin-4(3H)-one;

cis-5,6a,7,8,9,9a-Hexahydro-2,3,5-trimethylcyclopent[4,5]imidazo[2,1-b]purin-4(3H)-one;

cis-5,6a,7,8,9,9a-Hexahydro-2-(hydroxymethyl)-5-methyl-3-(phenylmethyl)-cyclopent[4,5]imidazo[2,1-b]purin-4(3H)-one;

cis-5,6a,7,8,9,9a-Hexahydro-2-methylthio-5-methyl-3-(Phenylmethyl)cyclopent-[4,5]imidazo[2,1-b]purin-4(3H)-one;

cis-3,4,5,6a,7,8,9,9a-Octahydro-5-methyl-4-oxo-3-(phenylmethyl)cyclopent-[4,5]imidazo[2,1-b]purin-2-carboxylic acid;

cis-3,4,5,6a,7,8,9,9a-Octahydro-5-methyl-4-oxo-3-(phenylmethyl)cyclopent-[4,5]imidazo[2,1-b]purin-2-carboxylic acid, methyl ester;

cis-5,6a,7,8,9,9a-Hexahydro-2-bromo-5-methyl-3-(phenylmethyl)cyclopent[4,5]imidazo[2,1-b]purin-4(3H)one;

cis-5,6a,7,8,9,9a-Hexahydro-2-(methylaminosulfonyl)-5-methyl-3-(phenylmethyl)cyclopent[4,5]imidazo[2,1-b]purin-4(3H)one;

cis-1-Cyclopentyl-5,6a,7,8,9,9a-hexahydro-5-methylcyclopent[4,5]imidazo[2,1-b]purin-4-(1H)one;

cis-5,6a,7,8,9,9a-Hexahydro-3,5-bis-(phenylmethyl)cyclopent(4,5)imidazo[2,1-b]purin-4(3H)one;

cis-6a,7,8,9,10,10a-Hexahydro-3,5-bis-(phenylmethyl)-3H-benzimidazo[2,1-b]purin-4(5H)one;

cis-3-Cyclopentyl-5,6a,7,8,9,9a-hexahydro-5-methylcyclopent[4,5]imidazo[2,1-b]purin-4(3H)one;

5'-Methyl-3'-(phenylmethyl)spiro[cyclopentane-1,7-(8'H)-(3'H)imidazo[2,1-b]purin]-4-(5H)one;

2',5'-Dimethyl-3'-(phenylmethyl)-spiro[cyclopentane-1,7-(8H)-(3'H)imidazo[2,1-b]purin]-4-(5'H)one;

cis-5,6a,(R)7,8,9,9a(S)-Hexahydro-5-methyl-3-(phenylmethyl)cyclopent[4,5]-imidazo[2,1-b]purin-4(3H)one;

cis-3-Cyclopentyl-5,6a,7,8,9,9a-Hexahydro-2,5-dimethyl-cyclopent[4,5]imidazo-[2,1-b]purin-4(3H)one;

5'-Methyl-2'-trifluoromethyl-3'-(phenylmethyl)spiro {cyclopentane-1,7'(8'H)-(3'H)imidazo[2,1-b]purin}-4-(5'H)-one;

7,8-Dihydro-5,7,7-trimethyl-2-trifluoromethyl-3-(phenylmethyl)-3H-imidazo[2,1-b]purin-4(5H)-one;

(+/−)-cis-5,6a,7,8,9,9a-Hexahydro-5-methyl-2-trifluoromethyl-3-(phenylmethyl)-cyclopent[4,5]imidazo[2,1-b]purin-4(3H)-one;

(+/−)-6a,7,8,9,9a,10,11,11a-Octahydro-2,5-dimethyl-3-(phenylmethyl)-3H-pentaleno[6a',1':4,5]imidazo[2,1-b]purin-4(5H)-one;

(+)-6a,7,8,9,9a,10,11,11a-Octahydro-2,5-dimethyl-3-phenylmethyl-3H-pentaleno[6a',1':4,5]imidazo[2,1-b]purin-4(5H)-one;

(−)-6a,7,8,9,9a,10,11,11a-Octahydro-2,5-dimethyl-3-phenylmethyl-3H-pentaleno[6a',1':4,5]Imidazo[2,1-b]purin-4(5H)-one;

(+/−) 6a,7,8,9,9a,10,11,11a-Octahydro-2,5-dimethyl-3H-pentaleno[6a',1':4,5]-imidazo[2,1-b]purin-4(5H)-one;

(+)-6a,7,8,9,9a,10,11,11a-Octahydro-2,5-dimethyl-3H-pentaleno[6a',1':4,5]-imidazo[2,1-b]purin-4(5H)-one;

(−)-6a,7,8,9,9a,10,11,11a-Octahydro-2,5-dimethyl-3H-pentaleno[6a',1':4,5]-imidazo[2,1-b]purin-4(5H)-one;

6a,7,8,9,10,10a,11,12,13,13a-Decahydro-2,5-dimethyl-(3-phenylmethyl)-napth[1,8a-d]imidazo[2,1-b]purin-4(5H) one;

7(R)-Cyclohexyl-7,8-dihydro-2,5-dimethyl-3-(phenylmethyl)-3H-imidazo[2,1-b]purin-4(3H)-one;

7(R)-Cyclohexyl-7,8-dihydro-2,5-dimethyl-3H-imidazo[2,1-b]purin-4(5H)-one;

7(S)-Cyclohexyl-7,8-dihydro-2,5-dimethyl-3-(phenylmethyl)-3H-imidazo[2,1-b]purin-4(3H)-one;

7(S)-Cyclohexyl-7,8-dihydro-2,5-dimethyl-3H-imidazo[2,1-b]purin-4(5H)-one;

5,6a(R),7,8,9,9a(S)-Hexahydro-2,5-dimethyl-[3-(trimethylacetoxy)methyl]-cyclopent[4,5]imidazo[2,1-b]purin-4(3H)-one;

5,6a(R),7,8,9,9a(S)-Hexahydro-2,5-dimethyl-3-(4-pyridylmethyl)cyclopent-[4,5]imidazo[2,1-b]purin-4(3H)-one;

5,6a(R),7,8,9,9a(S)-Hexahydro-2,5-dimethyl-3-[2-(4-morpholinyl)-ethyl]cyclopent[4,5]imidazo[2,1-b]purin-4(3H)-one;

5,6a(R),7,8,9,9a(S)-Hexahydro-2,5-dimethyl-3-[acetoxymethyl]cyclopent-[4,5]imidazo[2.1-b]purin-4(3H)-one;

5,6a,7,8,9,9a-Hexahydro-2,5,6a-trimethyl-3-(phenylmethyl)cyclopent-[4,5]imidazo[2,1-b]purin-4(3H)-one;

5,6a(R),7,8,9,9a(S)-Hexahydro-2,5,6a-trimethyl-3-(phenylmethyl)-cyclopent[4,5]imidazo[2,1-b]purin-4(3H)-one;

5,6a(S),7,8,9,9a(R)-Hexahydro-2,5,6a-trimethyl-3-(phenylmethyl)-cyclopent[4,5]imidazo[2,1-b]purin-4(3H)-one;

cis-6a,7,8,9,10,10a-Hexahydro-2,5,7-trimethyl-3-(phenylmethyl)-3H-benzimidazo[2,1-b]purin-4(5H)-one;

cis-5,6a,7,8,9,9a-Hexahydro-2,5,6a-trimethylcyclopent[4,5]imidazo[2,1-b]purin-4(3H)-one; or cis-[6a,7,8,9,10,10a-Hexahydro-2,5,7-trimethyl-3H-benzimidazo[2,1-b]purin-4(5H)-one], in free or salt form.

5.8: A compound which is a substituted imidazo[2,1-b]purin-4-one, in free or pharmaceutically acceptable salt form, e.g. a compound of Formula VIIIa, VIIIb or according to any of formulae 5.1-5.7, wherein the compound inhibits phosphodiesterase-mediated (e.g., PDE1-mediated, especially PDE1B-mediated) hydrolysis of cGMP, e.g., with an $IC_{50}$ of less than 10 μM preferably less than 100 nM in an immobilized-metal affinity particle reagent PDE assay, for example, as described in Example 1 below.

In another embodiment, the PDE 1 Inhibitors for use in the methods of treatment described herein are Compounds of Formula IXa or IXb

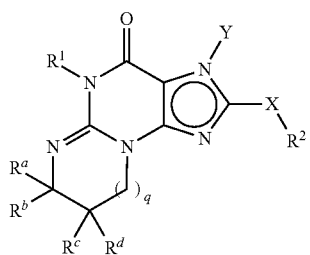

Formula IXa

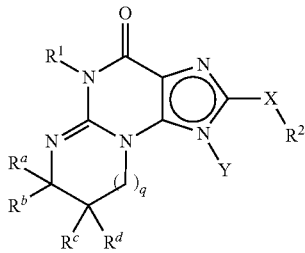

Formula IXb or a pharmaceutically acceptable salt thereof, wherein, q=0 or 1;

$R^1$ is 1-1, cycloalkyl, alkyl, $R^{23}$-alkyl- or $R^{26}$;

$R^a$, $R^b$ and $R^c$ are, independently of one another, each H, alkyl, cyoloalkyl, aryl, $R^{22}$-aryl- or $R^{24}$-alkyl-; or $R^a$ and $R^b$, together with the carbon to which they are both attached, form a 4- to 7-membered ring, and $R^c$ is H or alkyl; or $R^a$ and $R^c$, together with the respective carbons to which they are attached, form a 4- to 7-membered ring, and $R^b$ is H or alkyl;

(i) X is a bond;
Y is aryl-alkyl or $R^{22}$-aryl-alkyl-; and
$R^2$ is monohaloalkyl, polyhaloalkyl, provided that it is not trifluoromethyl, azido, cyano, oximino, cycloalkenyl, heteroaryl, $R^{22}$-heteroaryl- or $R^{27}$-alkyl-;

(ii) X is a bond;
Y is aryl-alkyl or $R^{22}$-aryl-alkyl-; and
$R^2$ is H, halo, —CONHR$^6$, —CONR$^6$R$^7$, —CO$_2$R$^6$, monohaloalkyl, polyhaloalkyl, azido, cyano, —C≡N—OR$^6$, cycloalkyl, cycloalkylalkyl, $R^{26}$, aminosulfonyl, alkyl or $R^{23}$-alkyl-(iii)

(iii) X is —O— or —S—;
Y is aryl-alkyl or $R^{22}$-aryl-alkyl-; and
$R^2$ is $R^{26}$, cycloalkyl cycloalkylalkyl, heterocycloalkyl, cycloalkenyl or $R^{26}$-alkyl-;

(iv) X is —O— or —S—;
Y is aryl-alkyl or $R^{22}$-aryl-alkyl-; and
$R^2$ is alkyl, $R^{26}$, cycloalkyl, cycloalkylalkyl, heterocycloalkyl, cycloalkenyl or $R^{28}$-alkyl-;

(v) X is —SO— or —SO$_2$—;
Y is aryl-alkyl or $R^{22}$-aryl-alkyl-; and
$R^2$ is alkyl, $R^{26}$, cycloalkyl, cycloalkylalkyl, heterocycloalkyl, cycloalkenyl or $R^{28}$-alkyl-;

(vi) X is —NR$^8$—;
Y is aryl-alkyl or $R^{22}$-aryl-alkyl-; and
$R^2$ is $(R^{29})_p$-alkyl-, cycloalkyl, $(R^{30})_p$-cycloalkyl-, cycloalkenyl, $(R^{30})_p$-cycloalkenyl-, heterocycloalkyl or $(R^{30})_p$-heterocycloalkyl-:

(vii) X is —NR$^8$—;
Y is aryl-alkyl or $R^{22}$-aryl-alkyl-; and
$R^2$ is alkyl, $R^{26}$, cycloalkyl, cycloalkylalkyl, heterocycloalkyl, cycloalkenyl or $R^{31}$-alkyl-; or (viii) X is —C≡C—;
Y is aryl-alkyl or $R^{22}$-aryl-alkyl-; and
$R^2$ is alkyl, $R^{26}$, cycloalkyl, cycloalkylalkyl or $R^{23}$-alkyl-;

where,
$R^6$ is H or $R^7$;
$R^7$ is alkyl, cycloalkyl or cycloalkylalkyl;
$R^8$ is heterocycloalkyl or $R^6$;
$R^{21}$ is 1-6 substituents each independently selected from the group consisting of halo, hydroxy, alkoxy, phenoxy, phenyl, nitro, aminosulfonyl, cyano, monohaloalkyl, polyhaloalkyl, thiol, alkylthio, cyoloalkyl, cycloalkyl-alkyl, amino, alkylamino, acylamino, carboxyl, —C(O)OR³⁴, carboxamido, —OCF₃ and acyloxy;

$R^{22}$ is 1-6 substituents each independently selected from the group consisting of alkyl and $R^{21}$;

$R^{23}$ is cycloalkoxy aryloxy, alkylthio, arylthio, cycloalkyl or $R^{28}$;

$R^{24}$ is cycloalkyl or $R^{26}$;

$R^{25}$ is hydroxy, alkoxy, amino, monoalkylamino, dialkylamino or $R^{26}$;

$R^{26}$ is aryl, $R^{22}$-aryl-, heteroaryl or $R^{22}$-heteroaryl-;

$R^{27}$ is cycloalkoxy, aryloxy, alkylthio, arylthio, heteroaryl, $R^{22}$-heteroaryl-, cycloalkyl, heterocycloalkyl, cycloalkenyl, cycloalkylamino or heterocycloalkylamino;

$R^{28}$ is cycloalkylamino, heterocycloalkylamino or $R^{25}$;

$R^{29}$ is alkoxy, cycloalkylamino, heterocycloalkylamino or $R^{26}$;

$R^{30}$ is halo, hydroxy, alkoxy, amino, aminosulfonyl, cyano, monohaloalkyl, polyhaloalkyl, thiol, alkylthio, alkyl, cyoloalkyl, cycloalkylalkyl or acyloxy;

$R^{31}$ is cycloalkyl or $R^{28}$;

$R^{34}$ is alkyl, aryl, aralkyl and heteroaryl; and p is 1 to 4.

The invention further provides the use of PDE 1 Inhibitors of Formula IXa or IXb as follows:

6.1 Formula IXa or IXb selected from a group consisting of:

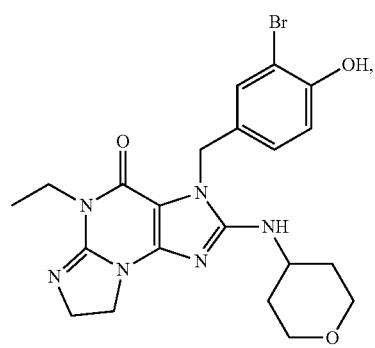

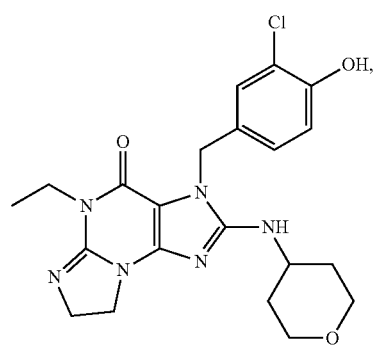

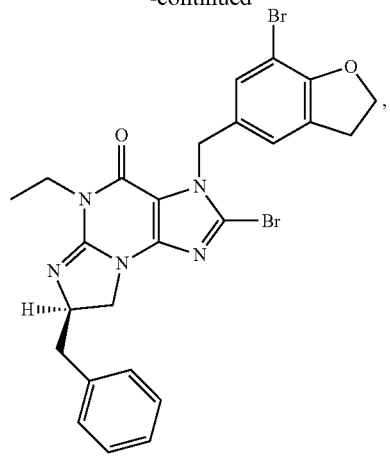

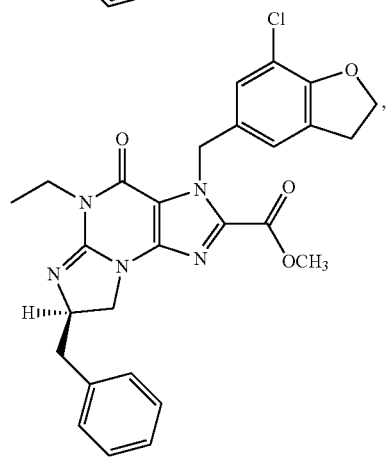

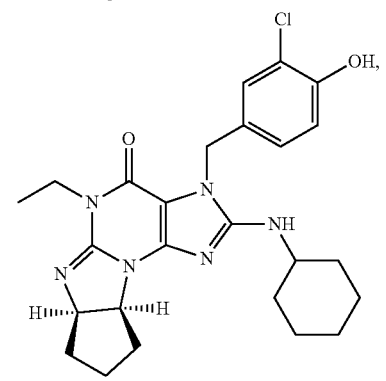

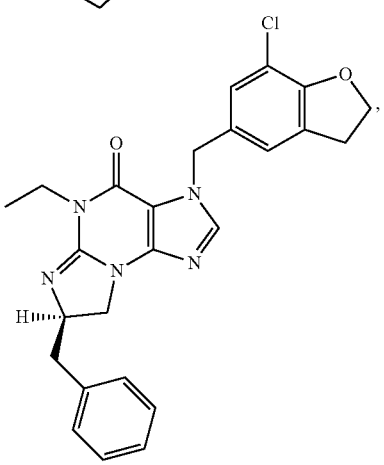

73
-continued
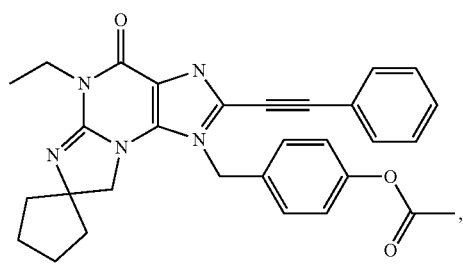
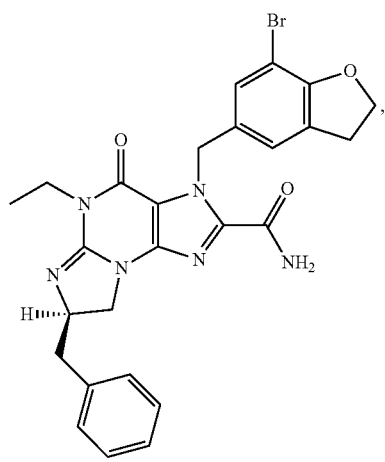
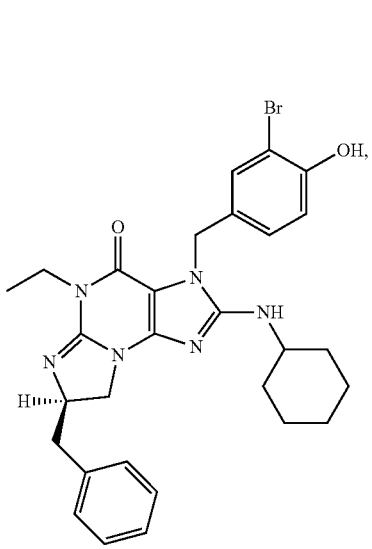
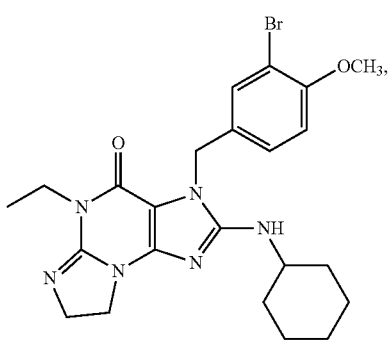
74
-continued
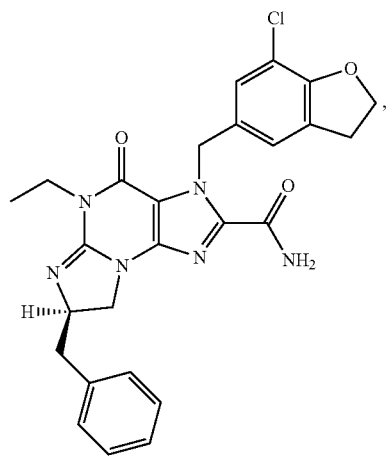
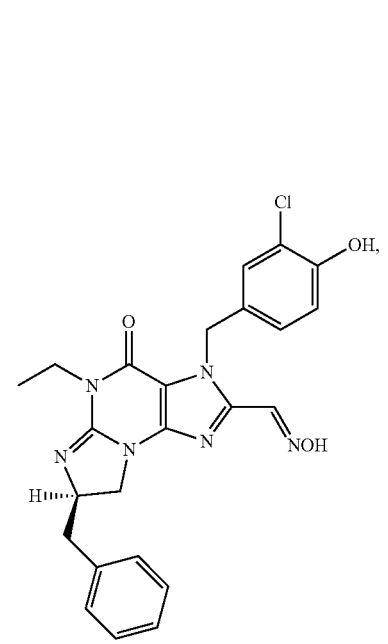
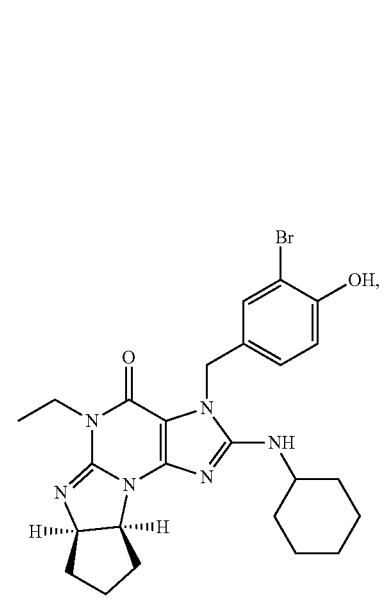

75
-continued
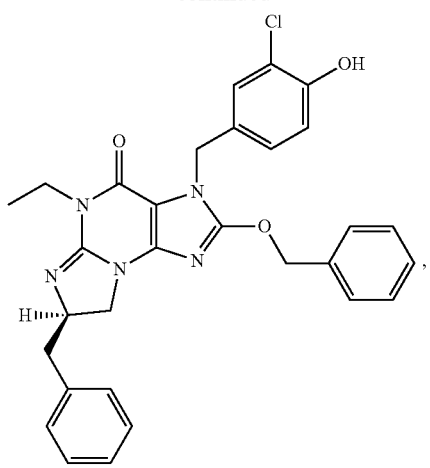
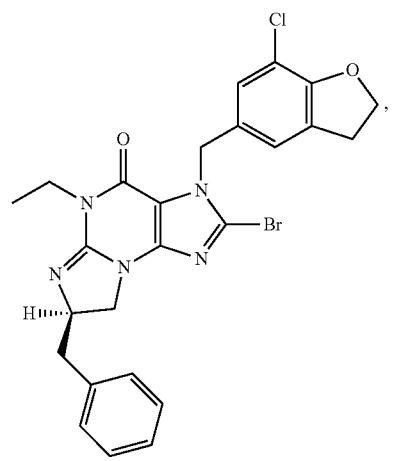
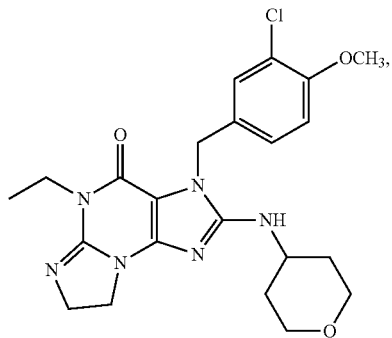
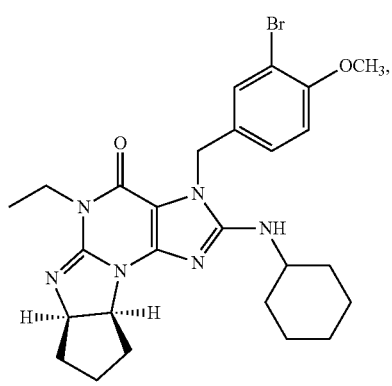
76
-continued
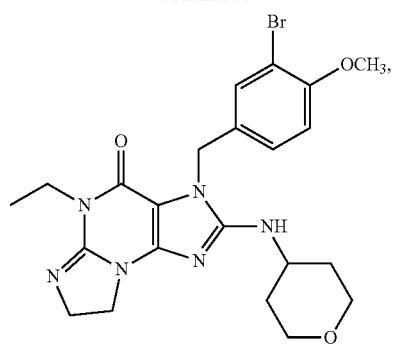
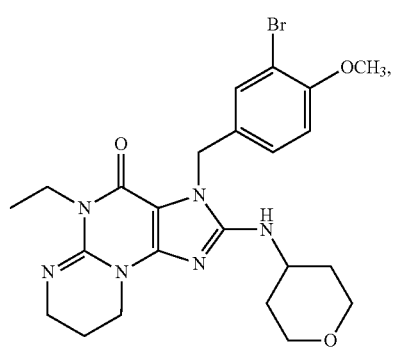
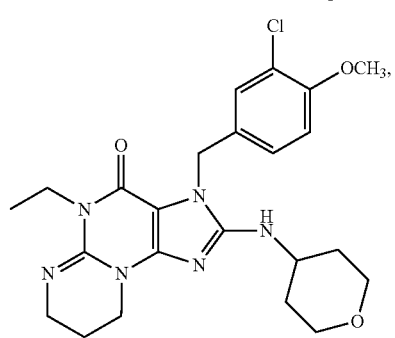
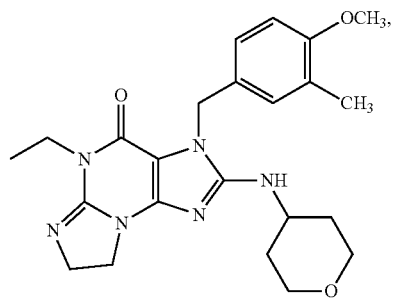
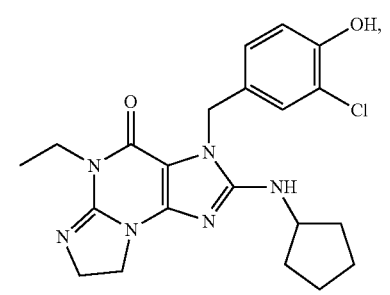

77
-continued
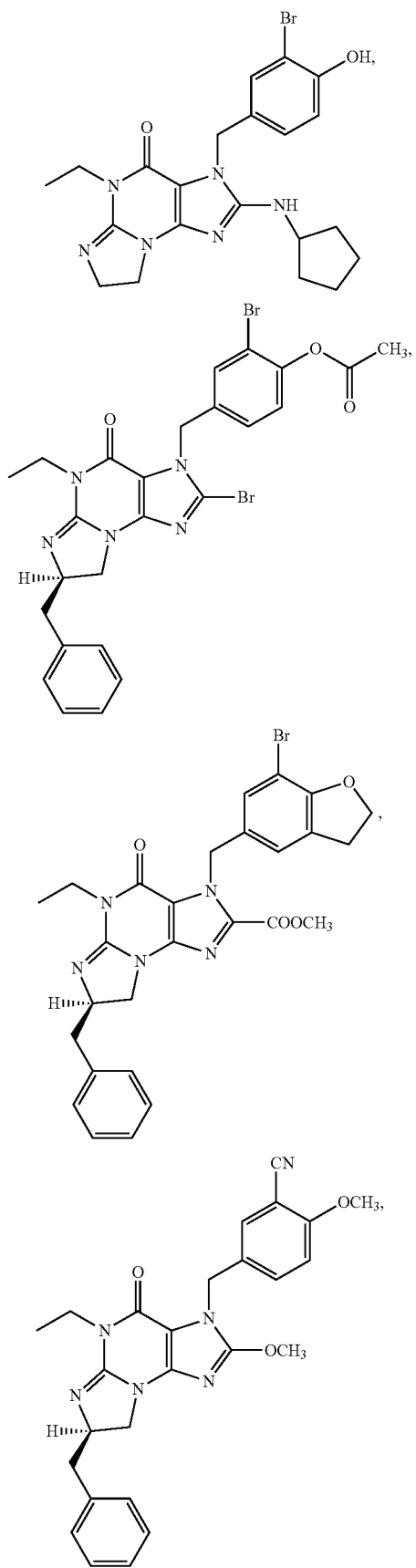
78
-continued
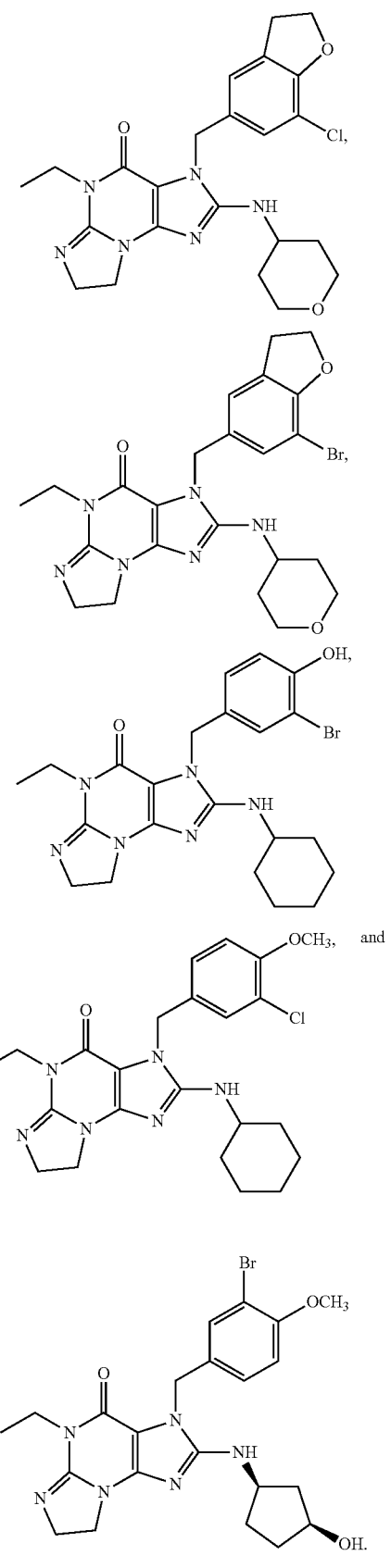

6.2 Formula IXa or IXb, in free or salt form, selected from a group consisting of:
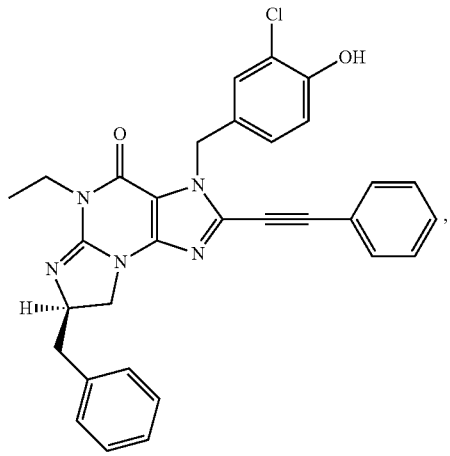
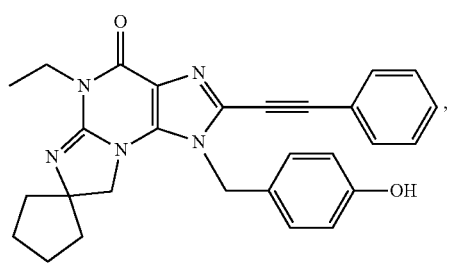
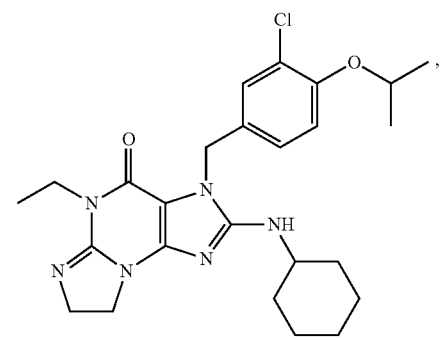
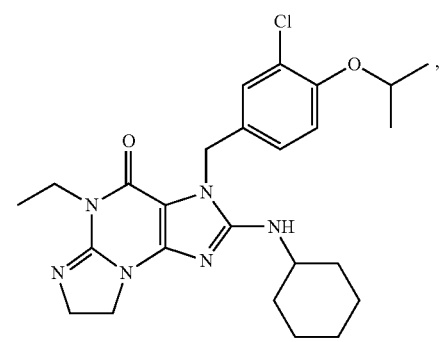
-continued
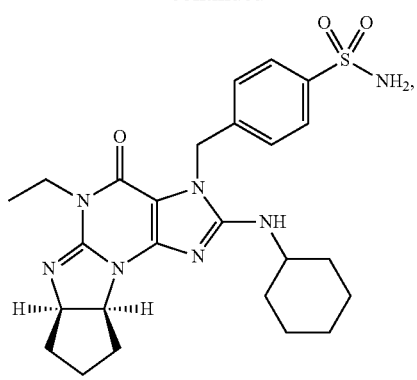
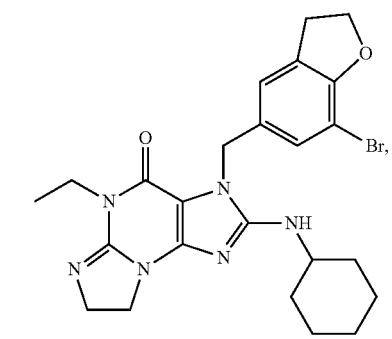
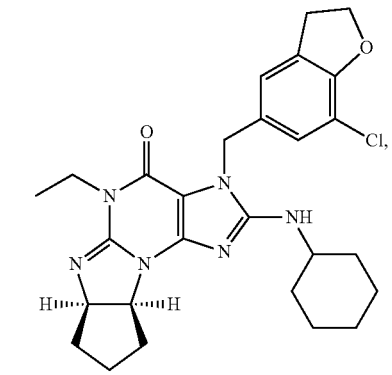
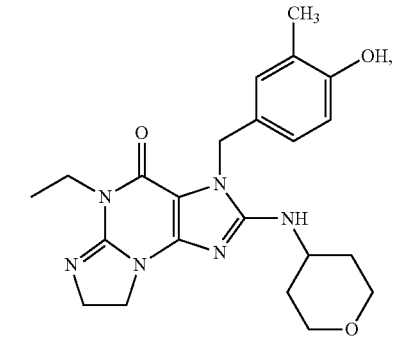

81
-continued
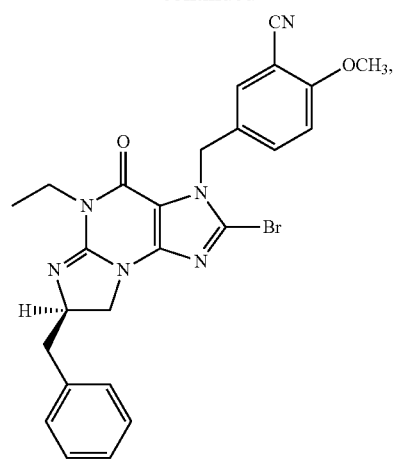
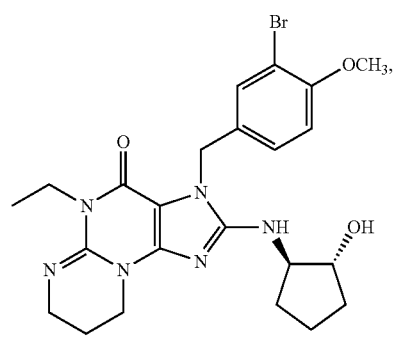
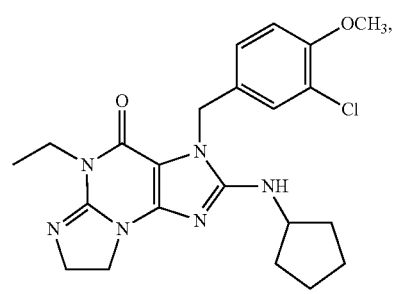
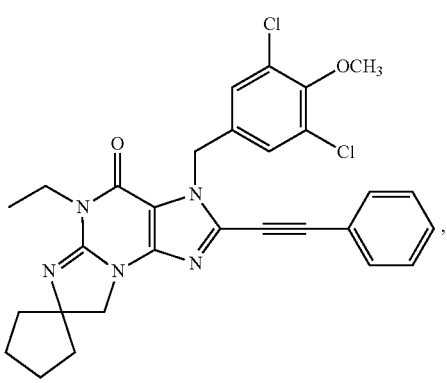
82
-continued
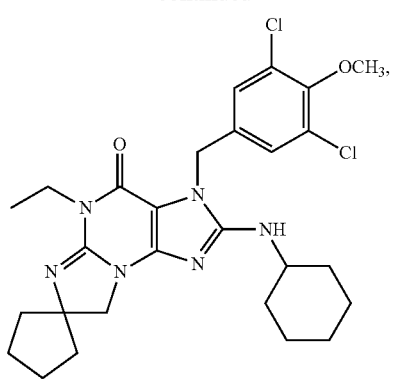
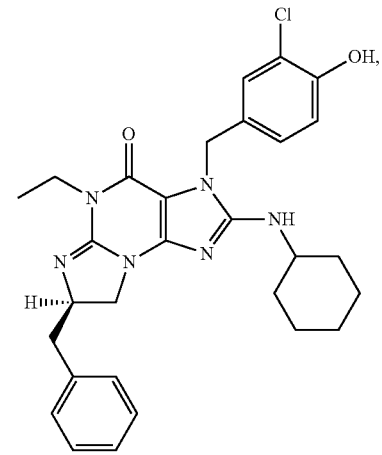
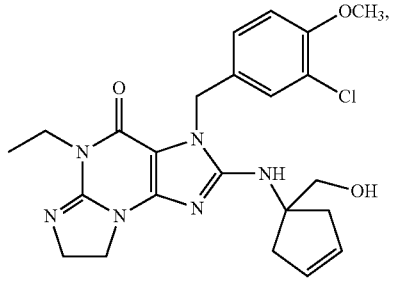
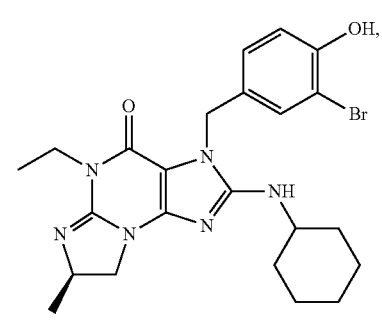

-continued
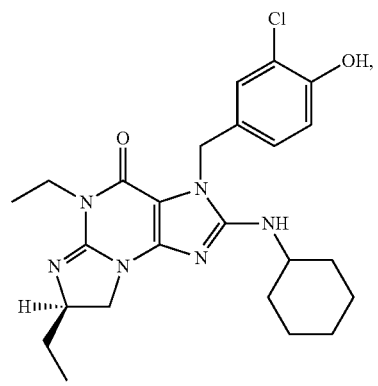
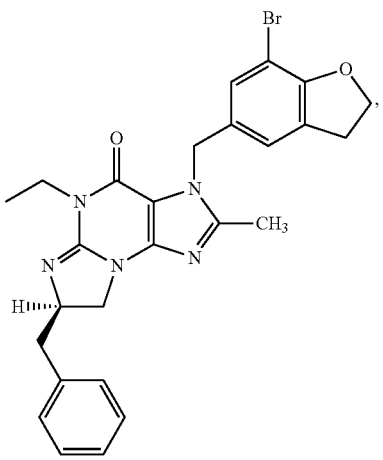
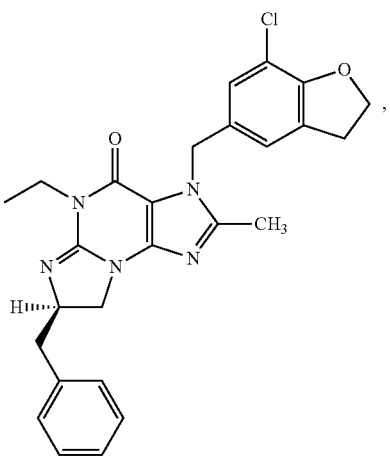
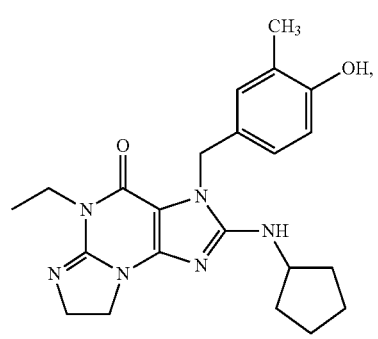
-continued
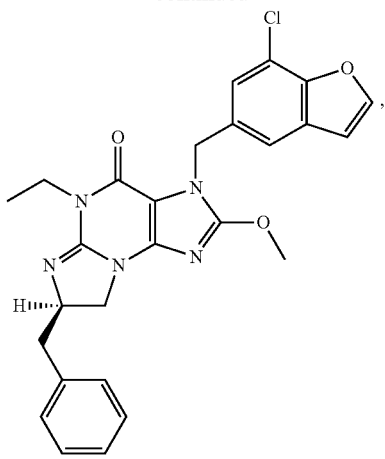
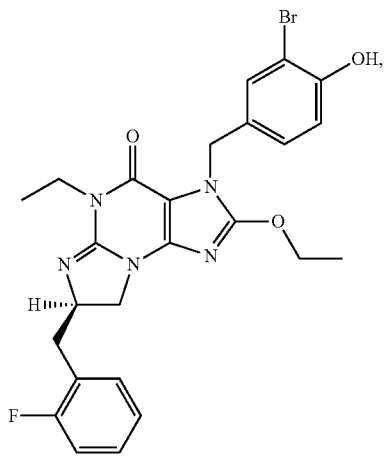
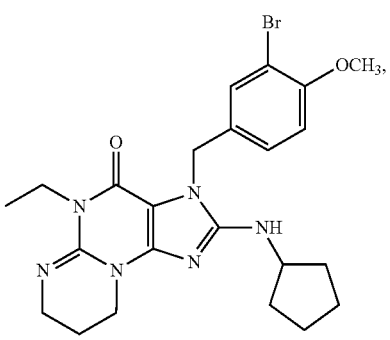
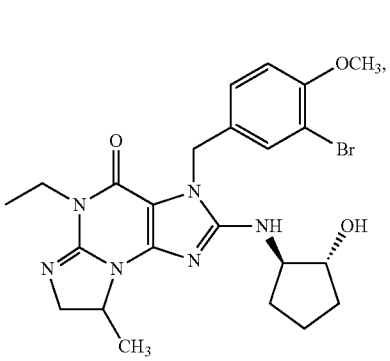

85

-continued

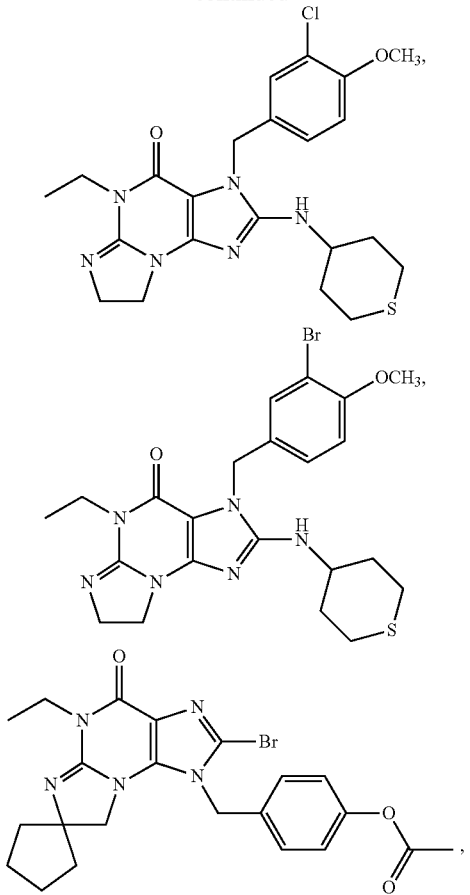

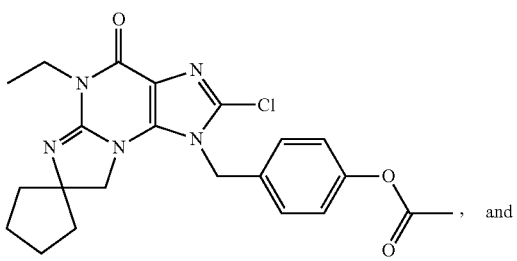

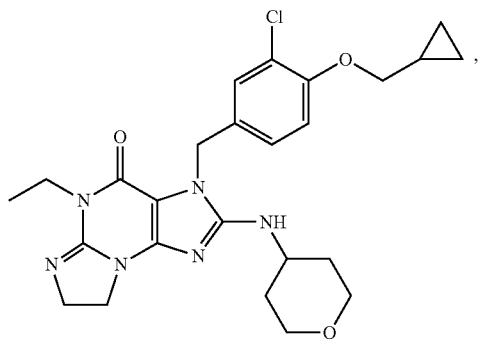

in free or salt form.

In another embodiment, the invention provides the use of PDE 1 Inhibitors of Formula X:

86

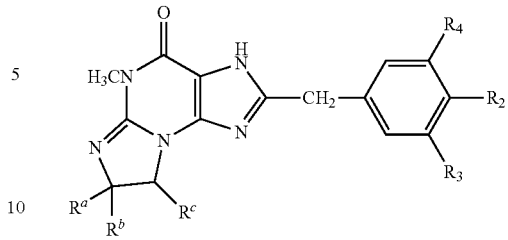

Formula X in free or a pharmaceutically acceptable salt thereof, wherein:

$R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring; and $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons.

In a further embodiment, the invention provides the use of PDE 1 Inhibitors of Formula X as follows:

7.1 Formula X, wherein $R_1$, $R_2$ and $R_3$ are independently selected from the group consisting of hydrogen, lower alkyl, lower alkoxy, halogeno, hydroxy, (di-lower alkyl)amino, 4-morpholinyl, 1-pyrrolidinyl, 1-pyrrolyl, —$CF_3$, —$OCF_3$, phenyl and methoxyphenyl; or $R_1$ and $R_2$ together are methylenedioxy; or $R_1$ and $R_2$ together with the carbon atoms to which they are attached form a benzene ring;

7.2 Formula X or 7.1, wherein $R_1$ is H, methoxy or trifluoromethyl;

7.3 Formula X or 7.1 or 7.2, wherein $R_1$ is H, 7.4 Formula X or any of 7.1-7.3, wherein $R_2$ is selected from a group consisting of H, halo (e.g., F, Cl), methoxy, methyl, trifluoromethyl, dimethylamino, phenyl, methoxyphenyl-, —$OCF_3$, 3,4-$OCH_2O$—, pyrrolidin-1-yl, pyrol-1-yl and morpholin-4-yl;

7.5 Formula X or any of 7.1-7.4, wherein $R_1$ and $R_2$ together with the carbon atoms to which they are attached form a a benzene ring;

7.6 Formula X or any of 7.1-7.5, wherein $R_3$ is H or methoxy;

7.7 Formula X or any of 7.1-7.6, wherein $R_3$ is H, 7.8 Formula X or any of 7.1-7.7, wherein $R^a$ is hydrogen and $R^b$ and $R^c$, together with the carbon atoms to which they are attached, form a saturated ring of 5 carbons; or $R^a$ is lower alkyl, $R^b$ is hydrogen or lower alkyl, and $R^c$ is hydrogen; or $R^a$, $R^b$ and the carbon atom to which they are attached form a saturated ring of 5-7 carbons, and $R^c$ is hydrogen; or $R^a$ is hydrogen, and $R^b$, $R^c$ and the carbon atoms to which they are attached form a tetrahydrofuran ring; or $R^a$ and $R^b$, together with the carbon atom to which they are attached, and $R^b$ and $R^c$, together with the carbon atoms to which they are attached, each form a saturated ring of 5-7 carbons;

7.9 Formula X or any of 7.1-7.8, wherein $R^a$ is hydrogen and $R^b$ and $R^c$ together with the carbon atoms to which they are attached, form a saturated ring of 5 carbons, and wherein $R_1$, $R_2$ and $R_3$ are as defined in the following table

| $R_1$ | $R_2$ | $R_3$ |
|---|---|---|
| H | H | H |
| —OCH₃ | H | H |
| H | F | H |
| H | —OCH₃ | H |
| H | OH | H |
| H | —CH₃ | H |
| H | (CH₃)₂N— | H |
| —OCH₃ | —OCH₃ | —OCH₃ |
| —OCH₃ | —OCH₃ | H |
| —CF₃ | H | H |
| H | C₆H₅— | H |
| H | —OCF₃ | H |
| H | —N(pyrrolidine) | H |
| H | —N(pyrrole) | H |
| | 3,4-OCH₂O— | H |
| H | —N(morpholine) | H |
| H | —C₆H₄—OCH₃ | H |
| $R_1$ and $R_2$, together with the carbon atoms to which they are attached for a benzene ring | | H |
| H | Cl | H. |

7.10 Formula X or any of 7.1-7.9, selected from a group consisting of

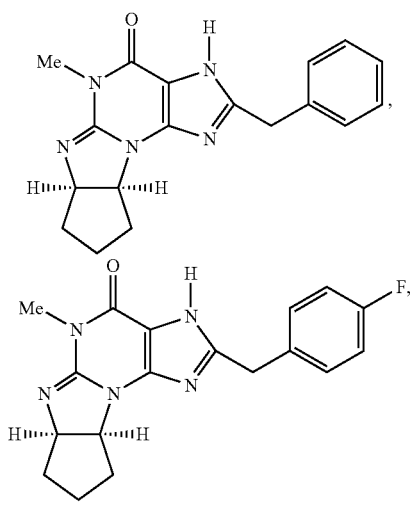

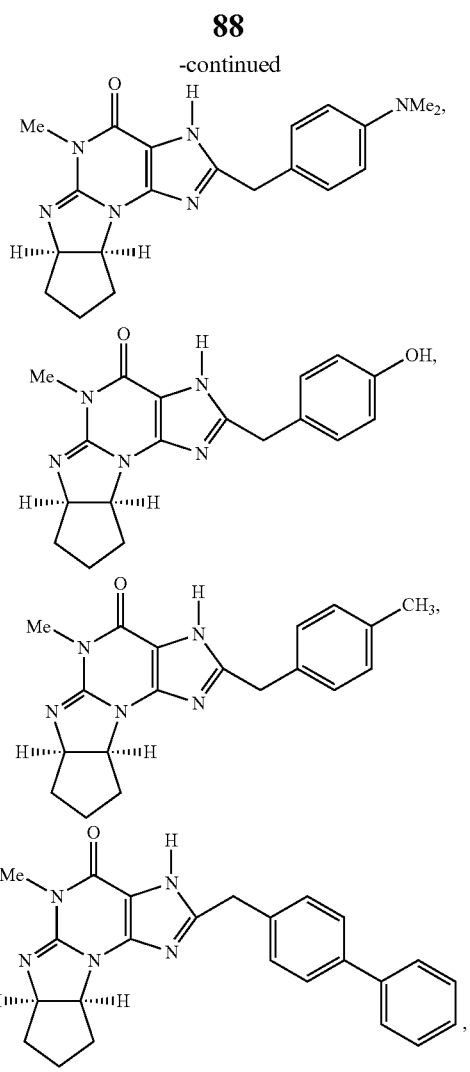

7.11 Formula X or any of 7.1-7.9, selected from a group consisting of:

2'-benzyl-5'-methyl-spiro[cyclopentane-1',7'(8'H)-[3'H]-imidazo[2,1-b]purin]-4'-(5'H)-one;

2'-benzyl-5,7,7-trimethyl-3H-imidazo[2,1-b]purin-4-(5H)-one;

(+)-2-benzyl-7,8-dihydro-5-methyl-7-(1-methylethyl)-1H-imidazo[2,1-b]-purin-4(5H)-one;

(+,−)-6a,7,8,9,9a, 10,11,11a-octahydro-5-methyl-2-(3,4-methylene-dioxyphenylmethyl)-3H-pentalen[6a, 1:4,5]imidazo[2,1-b]purin-4(5H)-one; and (+)-cis-6a,7,9,9a-tetrahydro-5-methyl-2-[4-(trifluoromethyl)-phenylmethyl]-3H-furo[3',4':4,5]imidazo[2,1-b]purin-4(5H)-one, in free or salt form.

7.12 Formulae X or 7.1-7.11, wherein the compounds inhibit phosphodiesterase-mediated (e.g., PDE1-mediated, especially PDE1B-mediated) hydrolysis of cGMP, e.g., with an IC$_{50}$ of less than 1 µM, preferably less than 25 nM in an immobilized-metal affinity particle reagent PDE assay, for example, as described in Example 1;

In another embodiment, the invention provides the use of PDE 1 Inhibitors selected from the following:

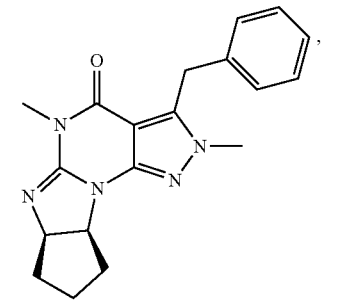

,

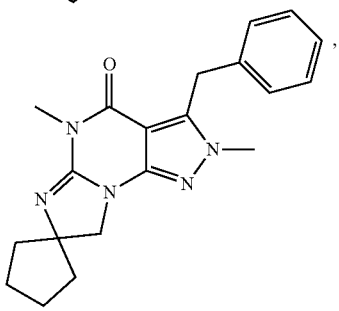

, and

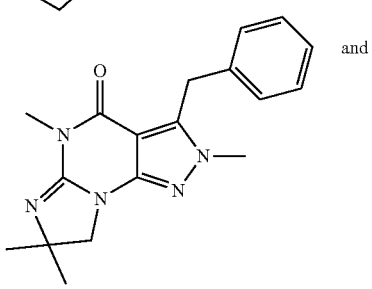

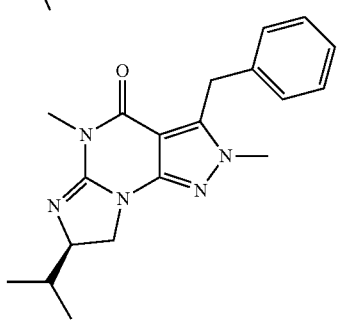

in free or salt form (Formula XI).

If not otherwise specified or clear from context, the following terms as used herein have the following meanings:

a. "Alkyl" as used herein is a saturated or unsaturated hydrocarbon moiety, preferably saturated, preferably one to seven carbon atoms in length, which may be linear or branched, and may be optionally substituted, e.g., mono-, di-, or tri-substituted, e.g., with halogen (e.g., chloro or fluoro), hydroxy, or carboxy.

b. "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.

c. "Heterocycloalkyl" as used herein is a saturated or unsaturated nonaromatic hydrocarbon moiety, preferably saturated, preferably comprising three to nine carbon atoms, at least one atom selected from a group consisting of N, O or S, at least some of which form a nonaromatic mono- or bicyclic, or bridged cyclic structure, and which may be optionally, substituted, e.g., with halogen (e.g., chloro or fluoro), hydroxy, or carboxy. Examples of heterocycloalkyl include pyrrolidinyl (e.g., pyrrolidin-1-yl), morpholinyl (e.g., morpholin-4-yl), d. "Aryl" as used herein is a mono or bicyclic aromatic hydrocarbon (e.g., phenyl, naphthyl), preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

e. "Heteroaryl" as used herein is an aromatic moiety wherein one or more of the atoms making up the aromatic ring is sulfur or nitrogen rather than carbon, e.g., pyridyl, thiadiazolyl, pyrrolyl (e.g., pyrrol-2-yl) or imidazolyl (e.g., 1H-imidazol-2-yl), which may be optionally substituted, e.g., with alkyl, halogen, haloalkyl, hydroxy or carboxy.

PDE 1 Inhibitors may exist in free or salt form, e.g., as acid addition salts. In this specification unless otherwise indicated language such as PDE 1 Inhibitors is to be understood as embracing the compounds in any form, for example free or acid addition salt form, or where the compounds contain acidic substituents, in base addition salt form. The PDE 1 Inhibitors are intended for use as pharmaceuticals, therefore pharmaceutically acceptable salts are preferred. Salts which are unsuitable for pharmaceutical uses may be useful, for example, for the isolation or purification of free PDE 1 Inhibitors or their pharmaceutically acceptable salts.

PDE 1 Inhibitors may in some cases also exist in prodrug form, for example when the compounds contain physiologically hydrolysable and acceptable esters. As used herein, "physiologically hydrolysable and acceptable ester" means esters of PDE 1 Inhibitors which are hydrolysable under physiological conditions to yield acids (in the case of PDE 1 Inhibitors which have hydroxy substituents) or alcohols (in the case of PDE 1 Inhibitors which have carboxy substituents) which are themselves physiologically tolerable at doses to be administered. As will be appreciated the term thus embraces conventional pharmaceutical prodrug forms.

Methods of making and formulating the PDE 1 Inhibitors, novel intermediates useful for making PDE 1 Inhibitors, and methods of using the PDE 1 Inhibitors for treatment of diseases are generally disclosed in EP 0201188 (or U.S. Pat. No. 4,666,908) and EP 0911333 (or U.S. Pat. No. 6,235,742); PCT/US2006/022066; PCT/US2006/033179; WO 03/042216 (U.S. Pat. No. 6,943,171); U.S. Pat. No. 6,969, 719; U.S. Pat. No. 5,939,419; EP 0 538 332 (U.S. Pat. No. 5,393,755); U.S. Pat. No. 5,393,755; U.S. Pat. No. 6,969, 719 B2, Xia et al., *J. Med. Chem.* (1997), 40, 4372-4377 and Ahn et al., *J. Med. Chem.* (1997), 40, 2196-2210, the contents of all of which are incorporated herein by reference.

Methods of Treatment

The invention provides methods of treatment of psychosis, e.g., any condition characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, or mania, such as in acute manic episodes and bipolar disorder, comprising administering an effective amount of a PDE 1 inhibitor, e.g., a PDE 1 Inhibitor as hereinbefore described, for example a Compound of any of Formulae I, Ia, II, III, IV, V, VI, VIIa, VIIb, VIIIa, VIIIb, IXa, IXb, X, XI. XII-XXI, or any of Formulae 1.2-1.17, 2.1-2.9, or 3.2-3.22, 4.1-4.17, 5.1-5.8, 6.1-6.1, 7.1-7.12, 15.1-15.95, 17.1-17.39, 19.1-19.39, 21.1-21.44 or 22.1-22.24, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously administering therapeutically effective amounts of (i) a PDE 1 Inhibitor, e.g., any of Formulae I, Ia, II, III, IV, V, VI, VIIa, VIIb, VIIIa, VIIIb, IXa, IXb, X, XI, XII-XXI, or any of Formulae 1.2-1.17, 2.1-2.9, 3.2-3.22, 4.1-4.17, 5.1-5.8, 6.1-6.2, 7.1-7.12, 15.1-15.95, 17.1-17.39, 19.1-19.39, 21.1-21.44 or 22.1-22.24; and (ii) an antipsychotic, e.g., Typical antipsychotics, e.g., Butyrophenones, e.g. Haloperidol (Haldol, Serenace), Droperidol (Droleptan);

Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap)

Thioxanthenes, e.g., Chlorprothixene, Flupenthixol (Depixol, Fluanxol), Thiothixene (Navane), Zuclopenthixol (Clopixol, Acuphase)

Atypical antipsychotics, e.g.,

Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine, to a patient in need thereof.

The present invention also provides (i) a PDE 1 Inhibitor for use in the treatment of any disease or condition as hereinbefore set forth, or in a method of treatment as hereinbefore set forth;

(ii) the use of a PDE 1 Inhibitor in the manufacture of a medicament for treating a disease or condition as hereinbefore set forth, or manufacture of a medicament for use in a method of treatment as hereinbefore set forth; and (iii) a pharmaceutical composition comprising a PDE 1 Inhibitor in combination or association with a pharmaceutically acceptable diluent or carrier for use in the treatment of a disease or condition as hereinbefore set forth, or for use in a method of treatment as hereinbefore set forth.

The words "treatment" and "treating" are to be understood accordingly as embracing prophylaxis and treatment or amelioration of any of the symptoms of disease as well as treatment of the cause of the disease.

Dosages employed in practicing the present invention will of course vary depending, e.g. on the particular disease or condition to be treated, the particular PDE 1 Inhibitor used, the mode of administration, and the therapy desired. PDE 1 Inhibitors may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a PDE 1 Inhibitor, together with a pharmaceutically acceptable diluent or carrier therefor.

Pharmaceutical compositions comprising PDE 1 Inhibitors may be prepared using conventional diluents or excipients and techniques known in the galenic art. Thus oral dosage forms may include tablets, capsules, solutions, suspensions and the like.

EXAMPLES

1. Measurement of PDE1B Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 mole of 3',5'-cAMP to 5'-AMP per min at pH 7.5 at 30° C. One part enzyme is added to 1999 parts reaction buffer (30 µM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.25 mU/ml. 99 µl of diluted enzyme solution is added into each well in a flat bottom 96-well polystyrene plate to which 1 µl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 µM) in a 384-well microtiter plate. The reaction is incubated in dark at room temperature for 15 min. The reaction is halted by addition of 60 µl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

What is claimed is:

1. A method of treatment for psychosis, schizoaffective disorder, schizophreniform disorder, psychotic disorder, delusional disorder, mania or bipolar disorder comprising administering an effective amount of a PDE 1 inhibitor to a patient in need thereof wherein the PDE 1 inhibitor is:

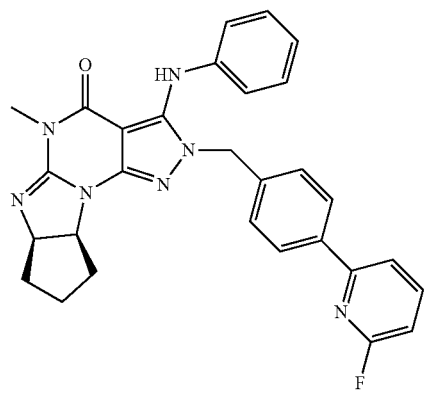 [SMILES: CN1C(=O)c2c(nn(Cc3ccc(-c4cccc(F)n4)cc3)c2Nc2ccccc2)N2C1=N[C@@H]1CCC[C@@H]12]

in free or salt form, including its enantiomers, diastereoisomers and racemates.

2. The method according to claim 1, wherein the compound inhibits phosphodiesterase-mediated hydrolysis of cGMP or cAMP.

3. The method according to claim 1, wherein the compound is a PDE1B inhibitor.

4. The method according to claim 1, wherein the method further comprises administering a compound or compounds selected from typical and atypical antipsychotics to a patient in need thereof.

5. The method according to claim 1, wherein the PDE1 inhibitor is in free or pharmaceutically acceptable salt form, in combination or association with a pharmaceutically acceptable diluent or carrier.

* * * * *